(12) United States Patent
Jakobi et al.

(10) Patent No.: US 7,084,158 B2
(45) Date of Patent: Aug. 1, 2006

(54) SUBSTITUTED PROPARGYLAMINES

(75) Inventors: Harald Jakobi, Frankfurt (DE); Susan Mary Cramp, Braintree (GB); Joachim Dickhaut, Heidelberg (DE); Stephen Lindell, Kelkheim-Fischbach (DE); Jörg Tiebes, Frankfurt (DE); Maria Asuncion Canales, Bad Soden (DE); Daniela Jans, Bad Homburg (DE); Waltraud Hempel, Liederbach (DE); Reed Nathan Royalty, Königstein (DE); Susan Marie McComb, Bad Soden (DE); Maria-Theresia Thönessen, Heidesheim (DE); Jutta Maria Waibel, Frankfurt (DE); Vincent Lee Salgado, Oberursel (DE)

(73) Assignee: Bayer Cropscience S.A., Lyons (FR)

( * ) Notice: Subject to any disclaimer, the term of this patent is extended or adjusted under 35 U.S.C. 154(b) by 344 days.

(21) Appl. No.: 10/225,354

(22) Filed: Aug. 22, 2002

(65) Prior Publication Data

US 2004/0014784 A1    Jan. 22, 2004

(30) Foreign Application Priority Data

Aug. 23, 2001 (DE) ................................ 101 41 339
Apr. 20, 2002 (DE) ................................ 102 17 697

(51) Int. Cl.
*A01N 40/43* (2006.01)
*C07D 211/14* (2006.01)

(52) U.S. Cl. ...................... 514/315; 546/192; 424/405; 514/317

(58) Field of Classification Search ................ 546/192; 424/405; 514/315, 317
See application file for complete search history.

(56) References Cited

U.S. PATENT DOCUMENTS

| 4,347,252 | A | * | 8/1982 | Leftwick et al. ............ 514/317 |
| 4,871,748 | A | | 10/1989 | Hatton |
| 5,023,073 | A | * | 6/1991 | Nicholson ................ 514/224.8 |
| 5,380,883 | A | | 1/1995 | Benoit et al. |
| 5,622,954 | A | | 4/1997 | Henrie, II et al. |
| 5,677,307 | A | | 10/1997 | Gesing et al. |

FOREIGN PATENT DOCUMENTS

| DE | 3504412 A1 | | 8/1985 |
| DE | 195 44 393 A1 | | 5/1997 |
| EP | 0041324 A1 | | 12/1981 |
| EP | 0758652 A | | 2/1997 |
| FR | 2576021 A | | 7/1986 |
| WO | WO93/01712 | * | 2/1993 |
| WO | 93/20804 | | 10/1993 |

OTHER PUBLICATIONS

1987 BCPC Mono. No. 37 Stored Products Pest Control, p. 125, published by The British Crop Protection Council, Farnham, Surrey, UK.

*Chemical Abstracts*, Published by American Chemical Society, Columbus, Ohio, Database Accession No. 124:105597 CA, XP002220181, abstract of Gayral et al, "In vitro and in vivo antifilarial activity of ethynesulfonamides, epoxyethanesulfonamides and carboxamide analogs", *Arzneimittel-Forschung*, 45(10), pp. 1122-1127 (1995).

*Chemical Abstracts*, published by American Chemical Society, Columbus, Ohio, Database accession No. 67:88434 CA, XP002220182, abstract of Reisch et al, "Microbiological activity of simple acetylene comounds", *Arzneim.-Forschung*, 17(7), pp. 816-825 (1967).

*Chemical Abstracts*, published by American Chemical Society, Columbus, Ohio, Database accession No. 74:99954 CA, XP002220183, abstract of Pershin et al, "Bacteriological properties of some aromatic mono- and diacetylenic amines", *Izv. Akad. Nauk SSSR, Ser. Khim.*, No. 8, pp. 1904-1906 (1970).

*Chemical Abstracts*, published by American Chemical Society, Columbus, Ohio, Database accession No. 82:111174 CA, XP002220184, abstract of Kinoyan et al, "Intensity of the acetylnic band in some tertiary amines and their quaternary ammonium salts", *Arm. Khim. Zh.*, 27(11), pp. 923-925 (1974).

(Continued)

*Primary Examiner*—Sabiha Qazi
(74) *Attorney, Agent, or Firm*—Buchanan Ingersoll PC

(57) ABSTRACT

The present invention relates to the use of substituted aryl- and heteroarylpropargylamines of the formula (I)

$$R^1\text{---}\!\!\equiv\!\!\text{---}A\text{---}N\begin{matrix}R^2\\R^3\end{matrix},\qquad(I)$$

where
a) $R^1$ is heteroaryl or aryl, unsubstituted or mono- or polysubstituted by identical or different radicals,
b) A is a group $CR^4R^5$ or $C=O$, where
$R^4$ is hydrogen, halogen or alkyl;
$R^5$ is hydrogen, halogen or a substituted or unsubstituted hydrocarbon radical;
c) $R^2$ and $R^3$ together with the nitrogen atom to which they are attached form N-heteroaryl or N-heterocyclyl, unsubstituted or mono- or polysubstituted by identical or different radicals,
if appropriate also as N-oxide or salt, as pesticide against arthropods and helminths for protecting plants and animals.

39 Claims, No Drawings

OTHER PUBLICATIONS

*Chemical Abstracts*, published by American Chemical Society, Columbus, Ohio, Database accession No. 80:108293 CA, XP002220185, abstract of Chukhadzhyan et al, "Amines and ammonium compounds. XCIV. Base-catalyzed cyclization of dialkylpropargyl(allyl)(3-arylpropargyl)ammonium salts", *Zh. Org. Khim.*, 10(1), pp. 46-50 (1974).

*Chemical Abstracts*, published by American Chemical Society, Columbus, Ohio, Database accession No. 78:58212 CA, XP002220186, abstract Kotlyarevskii et al, "Piperidol derivatives of some aromatic acetylenes", *Izv. Akad. Nauk SSSR, Ser. Khim.*, No. 10, pp. 2254-2257 (1972).
AN 20000:208835 CAPPLUS Abstract.
AN 2000:460789 CAPPLUS Abstract.

* cited by examiner

SUBSTITUTED PROPARGYLAMINES

This application claims priority under 35 U.S.C. §§ 119 and/or 365 to Patent Application No. 101 41 339.4 filed in Germany on Aug. 23, 2001 and Patent Application No. 102 17 697.3 filed in Germany on Apr. 20, 2002; the entire contents of which are hereby incorporated by reference.

The invention relates to the use of substituted aryl- and heteroarylpropargylamines as pesticides, in particular against harmful arthropods and helminths.

In EP-A-0 041 324, 1-[3-(3,5-bistrifluoromethylphenyl)-2-propynyl]-4-tert-butylpiperidine is described as rodenticide. Similar compounds in which the tertiary butyl radical is substituted are described in DE-A-3 504 412. Further compounds of this type in which the butyl radical is replaced by other alkyl radicals are described in 1987 BCPC mono. No. 37 Stored Products Pest Control, p. 125. In addition, there are further publications in which compounds are mentioned in which aryl radicals are attached via propargyl to nitrogen-containing heterocycles.

Surprisingly, it has now been found that compounds of this type have insecticidal, acaricidal and helminticidal action. Some of the compounds are novel.

The invention provides a method for controlling harmful arthropods, such as insects and Acarina, and helminths, such as parasites of animals and plant-damaging nematodes, which comprises applying to these pests or to the plants or animals, areas or substrates infected by them an effective amount of a compound of the formula (I)

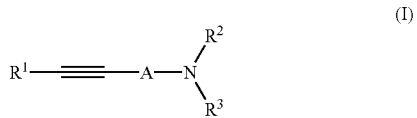

where
a) $R^1$ is heteroaryl or aryl, unsubstituted or mono- or polysubstituted by identical or different radicals,
b) A is a group $CR^4R^5$ or $C=O$, where
   $R^4$ is hydrogen, halogen or alkyl;
   $R^5$ is hydrogen, halogen or a substituted or unsubstituted hydrocarbon radical;
c) $R^2$ and $R^3$ together with the nitrogen atom to which they are attached form N-heteroaryl or N-heterocyclyl, unsubstituted or mono- or polysubstituted by identical or different radicals, if appropriate also as N-oxide and/or salt.

The invention also provides the use of compounds of the formula (I) for controlling arthropods, such as insects and Acarina, and helminths, such as parasites of animals and plant-damaging nematodes.

Many of the compounds of the formula (I) are novel, and the invention embraces all novel compounds of the formula (I), in particular those in which
a) $R^1$ is heteroaryl which is unsubstituted or mono- or polysubstituted by identical or different radicals or is aryl which is mono- or polysubstituted by identical or different radicals,
b) A is as defined above;
c) $R^2$ and $R^3$ together with the nitrogen atom to which they are attached form a piperidine which is unsubstituted or mono- or polysubstituted by identical or different radicals, with the proviso that, if $R^2$ and $R^3$ together with the nitrogen atom to which they are attached form a piperidine radical which is unsubstituted or substituted in the 4-position by unsubstituted or substituted alkyl, $R^1$ is not 3,5-bistrifluoromethylphenyl.

In the above formula, a hydrocarbon radical is a straight-chain, branched or cyclic saturated, partially saturated, unsaturated or aromatic organic radical having preferably 1 to 20 carbon atoms, for example alkyl, alkenyl, alkynyl, cycloalkyl, cycloalkenyl, cycloalkynyl, aryl or benzyl. This definition also applies to composite terms, such as cycloalkylalkenyl, cycloalkynylalkyl and arylalkynyl. If a hydrocarbon radical contains additional heteroatoms, these can in principle, i.e. the chemical structure permitting, be located in any position of the hydrocarbon radical.

In formula (I) and all subsequent formulae, carbon-containing radicals in the form of a chain, such as alkyl, alkoxy, haloalkyl, haloalkoxy, alkylamino and alkylthio, and the corresponding radicals which are unsaturated and/or substituted in the carbon skeleton, such as alkenyl and alkynyl, can in each case be straight-chain or branched. Unless indicated otherwise, in these radicals the lower carbon skeletons, preferably those having 1 to 6 carbon atoms or, in the case of unsaturated groups, 2 to 4 carbon atoms, are preferred.

Alkyl radicals, also in composite groups such as alkoxy, haloalkyl, etc., are, for example, methyl, ethyl, n- or iso-propyl, n-, iso-, t- or 2-butyl, pentyl radicals, hexyl radicals, such as n-hexyl, isohexyl and 1,3-dimethylbutyl, heptyl radicals, such as n-heptyl, 1-methylhexyl, 1,4-dimethylpentyl, and benzyl; alkenyl and alkynyl radicals, also in the composite groups, have the meaning of the unsaturated radicals which are possible and correspond to the alkyl radicals; alkenyl is, for example, allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl; alkynyl is, for example, propargyl, but-2-yn-1-yl, but-3-yn-1-yl, 1-methyl-but-3-yn-1-yl. The multiple bond can be located in any position of the unsaturated radical.

Cycloalkyl is a carbocyclic saturated ring system having preferably three to eight carbon atoms, for example cyclopropyl, cyclobutyl, cyclopentyl or cyclohexyl. Analogously, cycloalkenyl is a monocyclic alkenyl group having three to eight carbon ring members, for example cyclopropenyl, cyclobutenyl, cyclopentenyl and cyclohexenyl, where the double bond can be located in any position.

In the case of composite radicals, such as cycloalkylalkenyl, the first-mentioned radical can be located in any position of the second-mentioned radical.

In the case of an amino group which is doubly substituted, such as dialkylamino, these two substituents can be identical or different.

Halogen is fluorine, chlorine, bromine or iodine. Haloalkyl, -alkenyl and -alkynyl, etc., is alkyl, alkenyl and alkynyl, respectively, which is partially or fully substituted by halogen, preferably by fluorine, chlorine and/or bromine, in particular by fluorine or chlorine, for example $CF_3$, $CHF_2$, $CH_2F$, $CF_2CF_3$, $CHClCH_2F$, $CCl_3$, $CCl_2F$, $CClF_2$, $CHCl_2$, $CH_2CH_2Cl$; haloalkoxy is, for example, $OCF_3$, $OCHF_2$, $OCH_2F$, $OCF_2CF_3$, $OCH_2CF_3$ and $OCH_2CH_2Cl$; this applies correspondingly to other halogen-substituted radicals.

The term "heterocyclyl" is to be understood as meaning a saturated or partially unsaturated mono- or polycyclic ring system having preferably 3 to 14 ring members which contains one or more, preferably one to three, heteroatoms, preferably from a group consisting of oxygen, nitrogen ("N-heterocyclyl") and sulfur. If chemically possible, the point of attachment can be in any position of the heterocycle.

Examples are oxiranyl, aziridinyl, tetrahydrofuranyl, tetrahydrothienyl, pyrrolidinyl, isoxazolidinyl, isothioazolidinyl, pyrazolidinyl, oxazolidinyl, thiazolidinyl, imidazolidinyl, 1,2,4-oxadiazolidinyl, 1,2,4-thiadiazolidinyl, 1,2,4-triazolidin-3-yl, 1,3,4-thiadiazolidin-2-yl, 1,3,4-triazolidin-1-yl, 1,3,4-triazolidin-2-yl, 2,3-dihydrofuryl, 2,5-dihydrofuryl, 2,3-dihydrothienyl, 2,5-dihydrothienyl, 2,3-dihydropyrrolyl, 2,5-dihydropyrrolyl, 2,3-dihydroisoxazolyl, 4,5-dihydroisoxazolyl, 2,5-dihydroisothiazolyl, 2,3-dihydropyrazolyl, 4,5-dihydropyrazolyl, 2,5-dihydropyrazolyl, 2,3-dihydrooxazolyl, 4,5-dihydrooxazolyl, 2,5-dihydrooxazolyl, 2,3-dihydrothiazolyl, 4,5-dihydrothiazolyl, 2,5-dihydrothiazolyl, 2,3-dihydroimidazolyl, 4,5-dihydroimidazolyl, 2,5-dihydroimidazolyl, morpholinyl, piperidinyl, piperazinyl, tetrahydropyridazinyl, tetrahydropyrimidinyl, tetrahydropyrazinyl, 1,3,5-tetrahydrotriazinyl, 1,2,4-tetrahydrotriazin-1-yl, 1,2,4-tetrahydrotriazin-3-yl, 1,3-dihydrooxazinyl, 1,3-dithian-2-yl, tetrahydropyranyl, 1,3-dioxolan-2-yl, 3,4,5,6-tetrahydropyridin-2-yl, 1,2,5,6-tetrahydropyridin-1-yl, 1,2,3,4-tetrahydropyridin-1-yl, 1,2-dihydropyridin-1-yl, 1,4-dihydropyridin-1-yl, 4H-1,3-thiazinyl, 4H-3,1-benzothiazin-2-yl, 1,3-dithian-2-yl, 1,1-dioxo-2,3,4,5-tetrahydrothien-2-yl, 2H-1,4-benzothiazinyl, 1,3-dihydrooxazin-2-yl, hexahydroazepin-1-yl, homopiperazin-1-yl, 1,2,3,4-tetrahydroquinolin-1-yl, decahydroquinolin-1-yl, 1,2,3,4-tetrahydroisoquinolin-1-yl, decahydroisoquinolin-1-yl, 1,3,3-trimethyl-6-azabicyclo[3.2.1]octan-6-yl, 2,5-diazabicyclo[2.2.1]heptan-2-yl, 2-aza-5-oxabicyclo[2.2.1]heptan-2-yl, 2-aza-5-thiabicyclo[2.2.1]heptan-2-yl, 2-methyl-2,5-diazabicyclo[2.2.1]heptan-5-yl, 2-benzyl-2,5-diazabicyclo[2.2.1]heptan-5-yl, 4-azatricyclo[4.3.1.1(3,8)]undecan-5-on-4-yl.

Aryl is an aromatic mono- or polycyclic hydrocarbon radical having preferably 6 to 14, particularly preferably 6 to 12, carbon atoms, for example, phenyl, naphthyl, biphenyl and phenanthryl.

Heteroaryl is an aromatic mono-, bi- or tricyclic ring system having preferably 5 to 14 ring members which, in addition to carbon ring members, contains one to four nitrogen atoms or one to three nitrogen atoms ("N-heteroaryl") and one oxygen or one sulfur atom or one oxygen or one sulfur atom. Examples of 5-membered heteroaryl are 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 1,2,4-triazol-3-yl, 1,3,4-triazol-2-yl, 1,2,3-triazol-1-yl, 2-furyl, 3-furyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1-imidazolyl, 2-imidazolyl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl. Examples of 6-membered heteroaryl are 2-pyridinyl, 3-pyridinyl, 4-pyridinyl, 3-pyridazinyl, 4-pyridazinyl, 2-pyrimidinyl, 4-pyrimidinyl, 5-pyrimidinyl, 6-pyrimidinyl, 2-pyrazinyl, 1,3,5-triazin-2-yl, 1,2,4-triazin-3-yl and 1,2,4,5-tetrazin-3-yl. Examples of fused 5-membered heteroaryl are benzothiazol-2-yl and benzoxazol-2-yl. Examples of benzo-fused 6-membered heteroaryl are quinolinyl, isoquinolinyl, quinazolinyl and quinoxalinyl.

Depending on the nature and the attachment of the substituents, the compounds of the formula (I) can be present as stereoisomers. If, for example, one or more alkenyl groups are present, diastereomers may occur. If, for example, one or more asymmetrically substituted carbon atoms are present, enantiomers and diastereomers may occur. From the mixtures obtained in the preparation, stereoisomers can be obtained by customary separation methods, for example by chromatographic separation procedures. It is also possible to selectively prepare stereoisomers by using stereoselective reactions and employing optically active starting materials and/or auxiliaries. The invention also relates to all stereoisomers and mixtures thereof which are embraced by formula (I) but not specifically defined.

The term "partially or fully halogenated" is meant to express that in the groups thus characterized some or all of the hydrogen atoms may be replaced by identical or different halogen atoms as mentioned above.

If a group is polysubstituted, this is meant to be understood such that, when combining the different substituents, the general principles of the synthesis of chemical compounds are observed, i.e. that the formation of compounds is avoided of which the person skilled in the art knows that they are chemically unstable or impossible.

The symbols and indices of the formula (I) are preferably as defined below:

$R^1$ is an aryl or heteroaryl radical which is unsubstituted or mono- or polysubstituted by identical or different substituents from the group consisting of: alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, hydroxy, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, heteroaryloxy, heteroarylalkoxy, heteroarylalkenyloxy, heteroarylalkynyloxy, heterocyclyloxy, heterocyclylalkoxy, heterocyclylalkenyloxy, heterocyclylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenylthio, arylalkynylthio, heteroarylthio, heteroarylalkylthio, heteroarylalkenylthio, heteroarylalkynylthio, heterocyclylthio, heterocyclylalkylthio, heterocyclylalkenylthio, heterocyclylalkynylthio, amino, unsubstituted or substituted mono- or dialkylamino, unsubstituted or substituted mono- or diarylamino, unsubstituted or substituted mono- or diheteroarylamino, unsubstituted or substituted N-alkyl-N-arylamino, unsubstituted or substituted N-alkyl-N-heteroarylamino, alkenylamino, alkynylamino, cycloalkylamino, cycloalkenylamino, heterocyclylalkylamino, heterocyclylalkenylamino, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, heterocyclylsulfonyl, heterocyclylalkylsulfonyl, heterocyclylalkenylsulfonyl, heterocyclylalkynylsulfonyl, alkylsulfinyl, alkenylsulfinyl, alkynylsulfinyl, cycloalkylsulfinyl, cycloalkylalkylsulfinyl, cycloalkylalkenylsulfinyl, cycloalkylalkynylsulfinyl, arylsulfinyl, arylalkylsulfinyl, arylalkenylsulfinyl, arylalkynylsulfinyl, heteroarylsulfinyl, heteroarylalkylsulfinyl, heteroarylalkenylsulfinyl, heteroarylalkynylsulfinyl, heterocyclylsulfinyl, arylalkylsulfinyl, heterocyclylalkenylsulfinyl, heterocyclylalkynylsulfinyl, aminosulfonyl, unsubstituted or substituted mono- or dialkylaminosulfonyl, unsubstituted or substituted mono- or diarylaminosulfonyl, unsubstituted or substituted mono- or diheteroarylaminosulfonyl, unsubstituted or substituted N-alkyl-N-arylaminosulfonyl, unsubstituted or substituted N-alkyl-N-heteroarylaminosulfonyl, alkylsulfonyloxy, alkenylsulfonyloxy, alkynylsulfonyloxy, cycloalkylsulfonyloxy, cycloalkylalkylsulfonyloxy, cycloalkylalkenylsulfonyloxy, cycloalkylalkynylsulfonyloxy, arylsulfonyloxy, arylalkylsulfonyloxy, arylalkenylsulfonyloxy, arylalkynylsulfonyloxy, heteroarylsulfonyloxy, heteroarylalkylsulfonyloxy, heteroarylalkenylsulfonyloxy, heteroarylalkynylsulfonyloxy, heterocyclylsulfonyloxy, heterocyclylalkylsulfonyloxy, heterocyclylalkenylsulfonyloxy, heterocyclylalkynylsulfonyloxy, alkylsulfonylamino, alkenylsulfonylamino, alkynylsulfonylamino, cycloalkylsulfonylamino, cycloalkylalkylsulfoamino, cycloalkylalkenylsulfonylamino, cycloalkylalkynylsulfonylamino, arylsulfonylamino, arylalkylsulfonylamino, arylalkenylsulfonoamino, arylalkynylsulfonylamino, heteroaryisulfonylamino, heteroarylalkylsulfonylamino, heteroarylalkenylsulfonoamino, heteroarylalkynylsulfonylamino, alkylsulfonyl-N-alkylamino, alkenylsulfonyl-N-alkylamino, N-alkylalkynylsulfonyl-N-alkylamino, cycloalkylsulfonyl-N-alkylamino, cycloalkylalkylsulfonyl-N-alkylamino, cycloalkylalkenylsulfonyl-N-alkylamino, cycloalkylalkynylsulfonyl-N-alkylamino, arylsulfonyl-N-alkylamino, heteroarylsulfonyl-N-alkylamino, arylalkylsulfonyl-N-alkylamino, heteroarylalkylsulfonyl-N-alkylamino, arylalkenylsulfonyl-N-alkylamino, heteroarylalkenylsulfonyl-N-alkylamino, arylalkynylsulfonyl-N-alkylamino, heteroarylalkynylsulfonyl-N-alkylamino, heterocyclylsulfonyl-N-alkylamino, heterocyclylalkylsulfonyl-N-alkylamino, heterocyclylalkenylsulfonyl-N-alkylamino, heterocyclylalkynylsulfonyl-N-alkylamino, formyl, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, heterocyclylcarbonyl, heterocyclylalkylcarbonyl, heterocyclylalkenyl, heterocyclylalkynylcarbonyl, formyloxy, alkylcarbonyloxy, alkenylcarbonyloxy, alkynylcarbonyloxy, cycloalkylcarbonyloxy, cycloalkylalkylcarbonyloxy, cycloalkylalkenylcarbonyloxy, cycloalkylalkynylcarbonyloxy, arylcarbonyloxy, arylalkylcarbonyloxy, arylalkenylcarbonyloxy, arylalkynylcarbonyloxy, heteroarylcarbonyloxy, heteroarylalkylcarbonyloxy, heteroarylalkenylcarbonyloxy, heteroarylalkynylcarbonyloxy, heterocyclylcarbonyloxy, heterocyclylalkylcarbonyloxy, heterocyclylalkenyloxy, heterocyclylalkynylcarbonyloxy, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, heteroaryloxycarbonyl, heteroarylalkoxycarbonyl, heteroarylalkenyloxycarbonyl, heteroarylalkynyloxycarbonyl, heterocyclyloxycarbonyl, heterocyclylalkoxycarbonyl, heterocyclylalkenyloxycarbonyl, heterocyclylalkynyloxycarbonyl, aminocarbonyl, unsubstituted or substituted mono- or dialkylaminocarbonyl, unsubstituted or substituted mono- or diarylaminocarbonyl, unsubstituted or substituted mono- or diheteroarylaminocarbonyl, unsubstituted or substituted N-alkyl-N-arylaminocarbonyl, unsubstituted or substituted N-alkyl-N-heteroarylaminocarbonyl, unsubstituted or substituted alkylcarbonylamino, unsubstituted or substituted alkylcarbonyl-N-alkylamino, unsubstituted or substituted arylcarbonylamino, unsubstituted or substituted arylcarbonyl-N-alkylamino, unsubstituted or substituted heteroarylcarbonylamino, unsubstituted or substituted heteroarylcarbonyl-N-heteroarylamino, unsubstituted or substituted alkylcarbonyl-N-arylamino, unsubstituted or substituted arylcarbonyl-N-alkylamino, unsubstituted or substituted alkylcarbonyl-N-heteroarylamino, unsubstituted or substituted heteroarylcarbonyl-N-alkylamino, alkoxycarbonylamino, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, heteroaryloxycarbonylamino, heteroarylalkoxycarbonylamino, heteroarylalkenyloxycarbonylamino, heteroarylalkynyloxycarbonylamino, heterocyclyloxycarbonylamino, heterocyclylalkoxycarbonylamino, heterocyclylalkenyloxycarbonylamino, heterocyclylalkynyloxycarbonylamino, alkoxycarbonyl-N-alkylamino, alkenyloxycarbonyl-N-alkylamino, alkynyloxycarbonyl-N-alkylamino, cycloalkoxycarbonyl-N-alkylamino, cycloalkylalkoxycarbonyl-N-alkylamino, cycloalkylalkenyloxycarbonyl-N-alkylamino, cycloalkylalkynyloxycarbonyl-N-alkylamino, aryloxycarbonyl-N-alkylamino, arylalkoxycarbonyl-N-alkylamino, arylalkenyloxycarbonyl-N-alkylamino, arylalkynyloxycarbonyl-N-alkylamino, heteroarylalkoxycarbonyl-N-alkylamino, heteroarylalkenyloxycarbonyl-N-alkylamino, heteroarylalkynyloxycarbonyl-N-alkylamino, heterocyclylalkoxycarbonyl-N-alkylamino, heterocyclylalkenyloxycarbonyl-N-alkylamino, heterocyclylalkynyloxycarbonyl-N-alkylamino, formyl, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkylcarbonyloxy, haloalkenylcarbonyloxy, haloalkynylcarbonyloxy, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino, alkoxyalkoxy, arylalkoxyalkoxy, cyano, nitro, or a radical from the group consisting of alkyl—NH—N=CH—, aryl-$(CH_2)_n$—NH—N=CH—, alkoxy-N=CH—, aryl-$(CH_2)_n$—O—N=CH—, alkyl-NH—NH—CO— and arylalkyl-NH—NH—CO—.

$R^1$ is particularly preferably aryl or heteroaryl, unsubstituted or mono- or polysubstituted by identical or different substituents from the group consisting of halogen, nitro, cyano, alkyl, cycloalkyl, alkenyl, alkynyl, alkoxy, alkylcarbonyl, alkoxycarbonyl, alkylcarbonyloxy, alkylthio, alkylsulfinyl, alkylsulfonyl, alkylsulfonyloxy, aryl, aryloxy, heteroaryl, heterocyclyl, heterocyclylalkyl, benzyl—where the seventeen last-mentioned groups may be unsubstituted or substituted by one or more identical or different radicals from the group consisting of halogen, nitro, cyano, alkyl, haloalkyl, cycloalkyl, alkenyl, alkynyl, alkoxy, haloalkoxy and alkylthio.

Very particularly preferred substituents with which the aryl or heteroaryl radical of group $R^1$ may be substituted are halogen, nitro, cyano, $(C_1–C_4)$-alkyl, $(C_1–C_4)$-haloalkyl, $(C_2–C_4)$-haloalkenyl, $(C_2–C_4)$-haloalkynyl, $(C_1–C_4)$-haloalkoxy, $(C_2–C_4)$-haloalkenyloxy, $(C_2–C_4)$-haloalkynyloxy, unsubstituted or substituted aryl, heteroaryl, $(C_1–C_4)$-alkoxycarbonyl, $(C_1–C_4)$-alkoxy, $(C_1–C_4)$-alkylthio, $(C_1–C_4)$-alkylcarbonyloxy, $(C_1–C_4)$-alkylsulfonyl, aryloxy, $(C_1–C_4)$-alkylcarbonyl, heterocyclyl, heterocyclylalkyl, where aryl, heteroaryl and/or heterocyclyl systems may be unsubstituted or substituted by one or more radicals from the group consisting of halogen, $(C_1–C_4)$-alkyl, $(C_1–C_4)$-haloalkyl and $(C_1–C_4)$-alkoxy, or two substituents together form a group —O—CH$_2$—O— or —O—(CH$_2$)$_2$—O—.

Especially preferred are halogen, $(C_1–C_4)$-alkyl, $(C_1–C_4)$-haloalkyl, nitro, cyano, $(C_1–C_4)$-alkoxycarbonyl, $(C_1–C_4)$-alkoxy, $(C_1–C_4)$-alkylthio, phenyl, $(C_1–C_4)$-alkylcarbonyloxy, $(C_1–C_4)$-alkylsulfonyl, phenoxy, $(C_1–C_4)$-alkylcarbonyl, $(C_1–C_4)$-alkyl-piperidin-1-yl, where phenyl and piperidyl radicals may be unsubstituted or substituted by one or more radicals from the group consisting of halogen, $(C_1–C_4)$-alkyl, $(C_1–C_4)$-alkoxy and $(C_1–C_4)$-haloalkyl, or that two substituents together form a group —O—CH$_2$—O— or —O—(CH$_2$)$_2$—O—.

From among the last-mentioned group of substituents, the following are preferred: F, Cl, CF$_3$, methyl, ethyl, isopropyl, n-propyl, nitro, cyano, —COOCH$_3$, —OCH$_3$, —OC$_2$H$_5$, —SCH$_3$, phenyl, o-phenyl, —O—C(O)-isopropyl, —SO$_2$CH$_3$, —C(O)CH$_3$, —O—CH$_2$—O— and —CH$_3$—(4-methylpiperidin-1-yl).

In group $R^1$, the aryl or heteroaryl radical is preferably from the group consisting of 2-thienyl, 3-thienyl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 6-pyrimidinyl, 2-pyrazinyl, 1,3,5-triazin-2-yl, 1,2,4-triazin-3-yl, quinolinyl, isoquinolinyl, quinazolinyl, quinoxalinyl, naphthyl or phenyl, in particular from the group consisting of phenyl, 2-pyridyl, 3-pyridyl, 4-pyridyl, 2-pyrimidinyl, 4-pyrimidinyl, 5-pyrimidinyl, 2-thienyl, 3-thienyl and quinolin-4-yl.

A is a group CR$^4$R$^5$ or C=O, where $R^4$ is preferably hydrogen, fluorine or methyl, particularly preferably hydrogen or fluorine and very particularly preferably hydrogen;

$R^5$ is preferably hydrogen, fluorine, $(C_1–C_4)$-alkyl, $(C_2–C_4)$-alkenyl, $(C_2–C_4)$-alkynyl, $(C_3–C_6)$-cycloalkyl, $(C_3–C_8)$-cycloalkenyl, $(C_3–C_6)$-cycloalkyl-$(C_1–C_4)$-alkyl, aryl, aryl-$(C_1–C_4)$-alkyl, heteroaryl, heteroaryl-$(C_1–C_4)$-alkyl, particularly preferably hydrogen, fluorine or methyl and very particularly preferably hydrogen.

$R^2$ and $R^3$ together with the nitrogen atom to which they are attached form a N-heterocyclyl- or N-heteroaryl group which is unsubstituted or mono- or polysubstituted by identical or different substituents from the group consisting of alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, hydroxy, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, heteroaryloxy, heteroarylalkoxy, heteroarylalkenyloxy, heteroarylalkynyloxy, heterocyclyloxy, heterocyclylalkoxy, heterocyclylalkenyloxy, heterocyclylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenylthio, arylalkynylthio, heteroarylthio, heteroarylalkylthio, heteroarylalkenylthio, heteroarylalkynylthio, heterocyclylthio, heterocyclylalkylthio, heterocyclylalkenylthio, heterocyclylalkynylthio, amino, unsubstituted or substituted mono- or dialkylamino, unsubstituted or substituted mono- or diarylamino, unsubstituted or substituted mono- or diheteroarylamino, unsubstituted or substituted N-alkyl-N-arylamino, unsubstituted or substituted N-alkyl-N-heteroarylamino, alkenylamino, alkynylamino, cycloalkylamino, cycloalkenylamino, heterocyclylalkylamino, heterocyclylalkenylamino, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, heterocyclylsulfonyl, heterocyclylalkylsulfonyl, heterocyclylalkenylsulfonyl, heterocyclylalkynylsulfonyl, alkylsulfinyl, alkenylsulfinyl, alkynylsulfinyl, cycloalkylsulfinyl, cycloalkylalkylsulfinyl, cycloalkylalkenylsulfinyl, cycloalkylalkynylsulfinyl, arylsulfinyl, arylalkylsulfinyl, arylalkenylsulfinyl, arylalkynylsulfinyl, heteroarylsulfinyl, heteroarylalkylsulfinyl, heteroarylalkenylsulfinyl, heteroarylalkynylsulfinyl, heterocyclylsulfinyl, arylalkylsulfinyl, heterocyclylalkenylsulfinyl, heterocyclylalkynylsulfinyl, aminosulfonyl, unsubstituted or substituted mono- or dialkylaminosulfonyl, unsubstituted or substituted mono- or diarylaminosulfonyl, unsubstituted or substituted mono- or diheteroarylaminosulfonyl, unsubstituted or substituted N-alkyl-N-arylaminosulfonyl, unsubstituted or substituted N-alkyl-N-heteroarylaminosulfonyl, alkylsulfonyloxy, alkenylsulfonyloxy, alkynylsulfonyloxy, cycloalkylsulfonyloxy, cycloalkylalkylsulfonyloxy, cycloalkylalkenylsulfonyloxy, cycloalkylalkynylsulfonyloxy, arylsulfonyloxy, arylalkylsulfonyloxy, arylalkenylsulfonyloxy, arylalkynylsulfonyloxy, heteroarylsulfonyloxy, heteroarylalkylsulfonyloxy, heteroarylalkenylsulfonyloxy, heteroarylalkynylsulfonyloxy, heterocyclylsulfonyloxy, heterocyclylalkylsulfonyloxy, heterocyclylalkenylsulfonyloxy, heterocyclylalkynylsulfonyloxy, alkylsulfonylamino, alkenylsulfonylamino, alkynylsulfonylamino, cycloalkylsulfonylamino, cycloalkylalkylsulfoamino, cycloalkylalkenylsulfonylamino, cycloalkylalkynylsulfonylamino, arylsulfonylamino, arylalkylsulfonylamino, arylalkenylsulfonoamino, arylalkynylsulfonylamino, heteroarylsulfonylamino, heteroarylalkylsulfonylamino, heteroarylalkenylsulfonoamino, heteroarylalkynylsulfonylamino, alkylsulfonyl-N-alkylamino, alkenylsulfonyl-N-alkylamino, N-alkyl-alkynylsulfonyl-N-alkylamino, cycloalkylsulfonyl-N-alkylamino, cycloalkylalkylsulfonyl-N-alkylamino, cycloalkylalkenylsulfonyl-N-alkylamino, cycloalkylalkynylsulfonyl-N-alkylamino, arylsulfonyl-N-alkylamino, heteroarylsulfonyl-N-alkylamino, arylalkylsulfonyl-N-alkylamino, heteroarylalkylsulfonyl-N-alkylamino, arylalkenylsulfonyl-N-alkylamino, heteroarylalkenylsulfonyl-N-alkylamino, arylalkynylsulfonyl-N-alkylamino, heteroarylalkynylsulfonyl-N-alkylamino, heterocyclylsulfonyl-N-alkylamino, heterocyclylalkylsulfonyl-N-alkylamino, heterocyclylalkenylsulfonyl-N-alkylamino, heterocyclylalkynylsulfonyl-N-alkylamino, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenyl, heteroarylalkynylcarbonyl, heterocyclylcarbonyl, heterocyclylalkylcarbonyl, heterocyclylalkenyl, heterocyclylalkynylcarbonyl, formyloxy, alkylcarbonyloxy, alkenylcarbonyloxy, alkynylcarbonyloxy, cycloalkylcarbonyloxy, cycloalkylalkylcarbonyloxy, cycloalkylalkenylcarbonyloxy, cycloalkylalkynylcarbonyloxy, arylcarbonyloxy, arylalkylcarbonyloxy, arylalkenylcarbonyloxy, arylalkynylcarbonyloxy, heteroarylcarbonyloxy, heteroarylalkylcarbonyloxy, heteroarylalkenylcarbonyloxy, heteroarylalkynylcarbonyloxy, heterocyclylcarbonyloxy, heterocyclylalkylcarbonyloxy, heterocyclylalkenyloxy, heterocyclylalkynylcarbonyloxy, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, heteroaryloxycarbonyl, heteroarylalkoxycarbonyl, heteroarylalkenyloxycarbonyl, heteroarylalkynyloxycarbonyl, heterocyclyloxycarbonyl, heterocyclylalkoxycarbonyl, heterocyclylalkenyloxycarbonyl, heterocyclylalkynyloxycarbonyl, aminocarbonyl, unsubstituted or substituted mono- or dialkylaminocarbonyl, unsubstituted or substituted mono- or diarylaminocarbonyl, unsubstituted or substituted mono- or diheteroarylaminocarbonyl, unsubstituted or substituted N-alkyl-N-arylaminocarbonyl, unsubstituted or substituted N-alkyl-N-heteroarylaminocarbonyl, unsubstituted or substituted alkylcarbonylamino, unsubstituted or substituted alkylcarbonyl-N-alkylamino, unsubstituted or substituted arylcarbonylamino, unsubstituted or substituted arylcarbonyl-N-arylamino, unsubstituted or substituted heteroarylcarbonylamino, unsubstituted or substituted heteroarylcarbonyl-N-heteroarylamino, unsubstituted or substituted alkylcarbonyl-N-arylamino, unsubstituted or substituted arylcarbonyl-N-alkylamino, unsubstituted or substituted alkylcarbonyl-N-heteroarylamino, unsubstituted or substituted heteroarylcarbonyl-N-alkylamino, alkoxycarbonylamino, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, heteroaryloxycarbonylamino, heteroarylalkoxycarbonylamino, heteroarylalkenyloxycarbonylamino, heteroarylalkynyloxycarbonylamino, heterocyclyloxycarbonylamino, heterocyclylalkoxycarbonylamino, heterocyclylalkenyloxycarbonylamino, heterocyclylalkynyloxycarbonylamino, alkoxycarbonyl-N-alkylamino, alkenyloxycarbonyl-N-alkylamino, alkynyloxycarbonyl-N-alkylamino, cycloalkoxycarbonyl-N-alkylamino, cycloalkylalkoxycarbonyl-N-alkylamino, cycloalkylalkenyloxycarbonyl-N-alkylamino, cycloalkylalkynyloxycarbonyl-N-alkylamino, aryloxycarbonyl-N-alkylamino, arylalkoxycarbonyl-N-alkylamino, arylalkenyloxycarbonyl-N-alkylamino, arylalkynyloxycarbonyl-N-alkylamino, heteroaryloxycarbonyl-N-alkylamino, heteroarylalkoxycarbonyl-N-alkylamino, heteroarylalkenyloxycarbonyl-N-alkylamino, heteroarylalkynyloxycarbonyl-N-alkylamino, heterocyclylalkoxycarbonyl-N-alkylamino, heterocyclylalkenyloxycarbonyl-N-alkylamino, heterocyclylalkynyloxycarbonyl-N-alkylamino, formyl, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkylcarbonyloxy, haloalkenylcarbonyloxy, haloalkynylcarbonyloxy, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino, alkoxyalkoxy, arylalkoxyalkoxy, cyano, nitro, or a radical from the group consisting of alkyl-NH—N═CH—, aryl-$(CH_2)_n$—NH—N═CH—, alkoxy-N═CH—, aryl-$(CH_2)_n$—O—N═CH—, alkyl-NH—NH—CO— and arylalkyl-NH—NH—CO—.

Particularly preferably, $R^2$ and $R^3$ together with the nitrogen atom to which they are attached form N-heteroaryl or N-heterocyclyl, unsubstituted or mono- or polysubstituted by identical or different substituents from the group consisting of $(C_1-C_4)$-alkyl, $(C_2-C_4)$-alkenyl, $(C_2-C_4)$-alkynyl, $(C_3-C_6)$-cycloalkyl, $(C_3-C_6)$-heterocyclyl, $(C_3-C_8)$-cycloalkenyl, $(C_3-C_6)$-cycloalkyl-$(C_1-C_4)$-alkyl, aryl-$(C_1-C_4)$-alkyl, heteroaryl-$(C_1-C_4)$-alkyl, $(C_1-C_4)$-alkylcarbonyl, $(C_1-C_4)$-alkylcarbonyloxy, $(C_1-C_4)$-alkylsulfonyl, $(C_1-C_4)$-alkylsulfonyloxy, $(C_1-C_4)$-alkoxycarbonyl, SCN, $(C_1-C_4)$-dialkylamino, formyl—where the groups mentioned are unsubstituted or substituted by one or more identical or different radicals from the group consisting of halogen, nitro, cyano, alkyl, haloalkyl, cycloalkyl, alkenyl, alkynyl, phenyl, alkoxy, haloalkoxy and alkylthio. Two substituents together may form a group —O—CH$_2$—O— or —O—(CH$_2$)$_2$—O— or, at the same carbon atom, ═O.

Very particularly preferably, $R^2$ and $R^3$ together with the nitrogen atom to which they are attached form N-heteroaryl or N-heterocyclyl, unsubstituted or mono- or polysubstituted by identical or different substituents from the group consisting of $(C_1-C_4)$-alkyl, $(C_2-C_4)$-alkenyl, $(C_2-C_4)$-alkynyl, $(C_3-C_6)$-cycloalkyl, $(C_3-C_6)$-heterocyclyl, $(C_3-C_8)$-cycloalkenyl, $(C_3-C_6)$-cycloalkyl-$(C_1-C_4)$-alkyl, aryl-$(C_1-C_4)$-alkyl, heteroaryl-$(C_1-C_4)$-alkyl, $(C_1-C_4)$-alkylcarbonyl, $(C_1-C_4)$-alkylcarbonyloxy, $(C_1-C_4)$-alkoxycarbonyl, $(C_1-C_4)$-alkylsulfonyl, $(C_1-C_4)$-alkylsulfonyloxy—where the groups mentioned are unsubstituted or substituted by one or more identical or different radicals from the group consisting of halogen, nitro, cyano, alkyl, haloalkyl, cycloalkyl, alkenyl, alkynyl, alkoxy, haloalkoxy and alkylthio —SCN, $(C_1-C_4)$-dialkylamino, formyl, ═O, —O—CH$_2$—O—, —O—(CH$_2$)$_2$—O—.

Preferably, $R^2$ and $R^3$ together with the nitrogen atom to which they are attached form a 6-azabicyclo[3.2.1]octane, 1,2,5,6-tetrahydropyridine, decahydroquinoline, azepam, morpholine, piperazine, piperidine, unsubstituted or mono- or polysubstituted by identical or different substituents mentioned above, particularly preferably a piperidine.

Depending on the nature of the substituents defined above, the compounds of the formula (I) have acidic or basic properties and are able to form salts. Here, preference is given to the salts which are tolerable and customary in the field of pest control. If, for example, the compounds of the formula (I) carry groups such as hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore those of ammonia, of primary, secondary and tertiary amines having $(C_1-C_4)$-alkyl radicals and of mono-, di- and trialkanolamines of $(C_1-C_4)$-alkanols. If, for example, the compounds of the formula (I) carry groups such as amino, alkylamino and other groups which induce basic properties, these compounds can be reacted with acids to give salts. Suitable acids are, for example, mineral acids, such as hydrochloric acid, sulfuric acid and phosphoric acid, organic acids, such as acetic acid or oxalic acid, and acidic salts, such as NaHSO$_4$ and KHSO$_4$. The salts obtainable in this manner have insecticidal, acaricidal and/or helminthicidal/nematicidal properties, too.

The compounds of the formula (I) may have one or more asymmetrically substituted carbon atoms or stereoisomers on double bonds. Accordingly, enantiomers or diastereomers may occur. The invention embraces both the pure isomers and their mixtures. The mixtures of diastereomers can be separated into the isomers by customary methods, for example by selective crystallization from suitable solvents or by chromatography. Racemates can be separated by customary methods into the enantiomers.

The compounds according to the invention are prepared by methods known per se from the literature, as described in standard works on organic synthesis, for example Houben-Weyl, Methoden der Organischen Chemie [Methods of organic chemistry], Georg-Thieme-Verlag, Stuttgart.

The preparation is carried out under reaction conditions which are suitable and known for the reactions mentioned. It is also possible to employ variants known per se which are not mentioned in more detail here.

If desired, the starting materials can also be formed in situ, such that they are not isolated from the reaction mixture but immediately converted further into the compounds of the formula (I).

In all of the formulae mentioned below, the substituents and symbols have the same meaning as described under formula (I) unless defined otherwise.

Depending on the meaning of the substituents, the compounds of the formula (I) can be prepared, for example, by one or more of the processes shown in the schemes below.

Scheme 1:

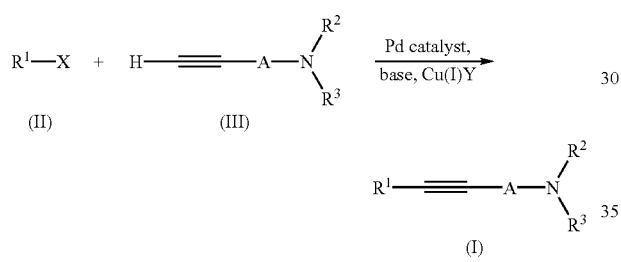

The palladium-catalyzed crosscoupling (Sonogashira coupling) shown in scheme 1 of a compound of the formula (II) in which X is —OSO$_2$CF$_3$ or halogen, preferably iodine, with a compound of the formula (III) gives the compounds of the formula (I) according to the invention. This reaction is preferably carried out in the presence of an amine base, for example diethylamine, triethylamine, piperidine, pyrrolidine or DBU, which, in addition to other solvents such as benzene, toluene, DMF, THF or diethyl ether, may also serve as solvent, or in the presence of another suitable base, for example an alkali metal alkoxide, such as potassium tert-butoxide in an inert organic solvent, such as DMSO, acetonitrile; and in the presence of a solvent and a palladium catalyst and also a copper(I) salt (Y is preferably I, Cl, Br, cyano or SCN), preferably copper(I) iodide (Y=I). Suitable palladium catalyst systems are, for example, Pd(PPh$_3$)$_4$, PdCl$_2$(PPh$_3$)$_2$ and Pd(OAc)$_2$(PPh$_3$)$_2$ or Pd(OAc)$_2$ and a tri-arylphosphine, preferably triphenylphosphine or tri-(o-tolyl)phosphine. These methods are described, for example, in Tetrahedron Lett. 4467 (1975), Comprehensive Organic Synthesis (B. M. Trost, I. Flemming, Eds), Pergamon Press, Oxford, Vol 3, 521–549 (1991), Org. Prep. Proct. Int. 129 (1995), J. Med. Chem. 40, 3542 (1997), J. Org. Chem. 63, 1109 (1998).

Compounds of the formula (II) are either commercially available or can be prepared according to generally known methods, for example Houben-Weyl, Methoden der Organischen Chemie, Georg-Thieme-Verlag, Stuttgart or Chem. Pharm. Bull. 27, 270 (1979).

Compounds of the formula (III) can be prepared, for example, according to scheme 2 from compounds of the formula (IV), in which X' is a leaving group, for example a chlorine, bromine or iodine atom or an alkylsulfonyloxy or arylsulfonyloxy radical, for example a tosyloxy radical.

Scheme 2:

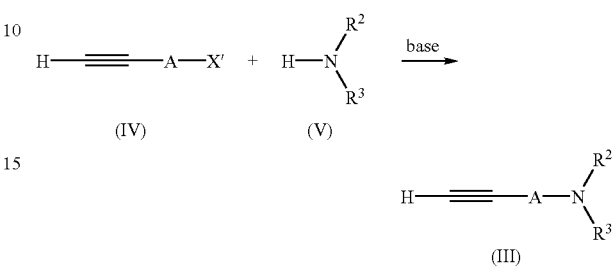

The compounds of the formula (III) are obtained in the presence of an inorganic or organic base, such as potassium carbonate or excess amine of the formula (V), in an inert organic solvent, such as methanol, acetone or DMF. Such methods are known, for example, from Org. Magn. Reson. 14, 161 (1980), Tetrahedron 41, 5685 (1985), J. Med. Chem. 34, 746 (1991), J. Org. Chem. 56, 3707 (1991), J. Org. Chem. 57, 3000 (1992), J. Med. Chem. 37, 2735 (1994).

Compounds of the formula (I) in which A is CR$^4$R$^5$, where R$^5$ is hydrogen, in particular those in which A is CH$_2$, are also obtainable, for example, according to scheme 3.

Scheme 3:

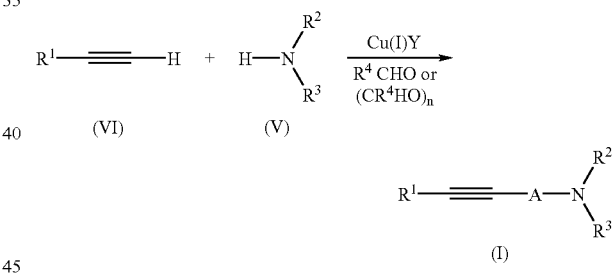

Compounds of the formula (I) are obtained according to scheme 3 by reacting compounds of the formula (V) with compounds of the formula (VI) and an aldehyde, such as, for example, benzaldehyde, acetaldehyde or formaldehyde, or an aldehyde source, such as paraformaldehyde or formalin, in the presence of a copper(I) salt, preferably copper(I) chloride (Y=Cl), in an inert organic solvent, such as, for example, dioxan. Such methods are known, for example, from Chem. Ber. 66, 418 (1933), J. Prakt. Chem. 331, 187 (1989), Tetrahedron Lett. 39, 967 (1998).

Compounds of the formula (VI) are either commercially available, or they can be obtained by Sonogashira coupling and subsequent removal of the protective group from R$^1$ X and a protected acetylene equivalent, such as, for example, trimethylsilylacetylene or 2-methylbut-3-yn-2-ol, according to known methods. Such methods are described, for example, in Comprehensive Organic Synthesis (B. M. Trost, I. Flemming, Eds), Pergamon Press, Oxford, Vol 3, 521–549 (1991), Synthesis. (1980), 627, J. Org. Chem. 50, 1763 (1985), Tetrahedron Lett. 34, 2071 (1993), Angew. Chem. Int. Ed. Engl. 18, 406 (1993), Synthesis (1996), 589.

In particular compounds of the formula (I), in which A is $CR^4R^5$ can also be obtained, for example, according to scheme 4.

Scheme 4:

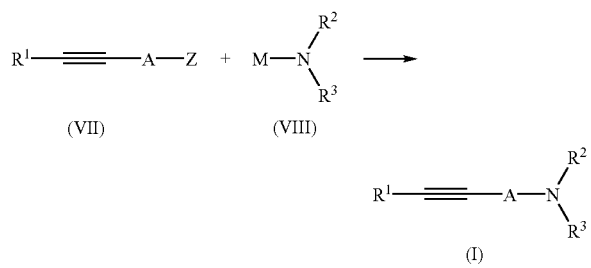

According to scheme 4, the compounds of the formula (I) are obtained by reacting compounds of the formula (VII) in which Z is a chlorine, bromine or iodine atom or an alkylsulfonyloxy or arylsulfonyloxy radical, for example a tosyloxy radical, with compounds of the formula (VIII), in which M is an alkali metal atom, preferably a lithium atom. If Z in the formula (VII) is chlorine, bromine or iodine, M in the formula (VIII) may furthermore be a hydrogen atom. If M in the formula (VIII) is a hydrogen atom, the reaction is carried out in the presence of an inorganic base, such as potassium carbonate, and in an inert organic solvent, such as acetone or DMF. If M in the formula (VIII) is not hydrogen, preference is given to inert organic solvents, such as diethyl ether or THF.

Compounds of the formula (VII) can be prepared by or analogously to known methods. These methods are known, for example, from *Chem. Phys. Lipids* 13, 159 (1974), *Synthesis* (1975), 255, *J. Am. Chem. Soc.* 60, 2662 (1938), *Bull. Chem. Soc. Jpn.* 46, 954 (1973), *J. Med. Chem.* 21, 253 (1978), *Bull. Soc. Chim. Fr.* (1969), 4514, *J. Org. Chem.* 49, 4344 (1984), *J. Med. Chem.* 41, 1084 (1998), *J. Org. Chem.* 63, 7472 (1998).

Collections of compounds of the formula (I) which can be synthesized by the abovementioned schemes may also be prepared in a parallel manner and this may be effected manually or in a semiautomated or fully automated manner. In this case, it is possible, for example, to automate the procedure of the reaction, the work-up or the purification of the products or of the intermediates. In total, this is to be understood as meaning a procedure as is described, for example, by S. H. DeWitt in "Annual Reports in Combinatorial Chemistry and Molecular Diversity: Automated Synthesis", Volume 1, Verlag Escom 1997, pages 69 to 77.

A number of commercially available apparatuses as are offered by, for example, Stem Corporation, Woodrolfe Road, Tollesbury, Essex, CM9 8SE, England or H+P Labortechnik GmbH, Bruckmannring 28, 85764 Oberschleißheim, Germany or Radleys, Shirehill, Saffron Walden, Essex, England may be used for the parallel procedure of the reaction and work-up. For the parallel purification of compounds of the formula (I), or of intermediates obtained during the preparation, use may be made, inter alia, of chromatography apparatuses, for example those from ISCO, Inc., 4700 Superior Street, Lincoln, Nebr. 68504, USA.

The apparatuses mentioned lead to a modular procedure in which the individual process steps are automated, but manual operations have to be performed between the process steps. This can be avoided by employing semiintegrated or fully integrated automation systems where the automation modules in question are operated by, for example, robots. Such automation systems can be obtained, for example, from Zymark Corporation, Zymark Center, Hopkinton, Mass. 01748, USA.

In addition to the method described here, compounds of the formula (I) may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Verlag Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131–5135), in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation according to the processes described herein yields compounds of the formula (I) in the form of substance collections which are referred to as libraries. The present invention also relates to libraries which comprise at least two compounds of the formula (I).

The compounds of the formula (I) are suitable for controlling animal pests, in particular arthropods such as insects, Acarina and helminths, such as parasites of animals and plant-damaging nematodes, very especially preferably for controlling insects and arachnids, which are encountered in agriculture, in animal husbandry, in livestock breeding, in horticulture, in forests, in the protection of stored goods and materials and in the domestic sector and in the hygiene sector, and have good plant tolerance and favorable toxicity to warm-blooded species. They are active against normally sensitive and resistant species and against all or individual development stages. The above mentioned pests include:

From the order of the Isopoda, for example, *Armadillidium* spp., *Oniscus* spp., *Porcellio* spp.

From the order of the Diplopoda, for example, *Blaniulus* spp.

From the order of the Chilopoda, for example, *Geophilus* spp., *Scutigera* spp.

From the order of the Symphyla, for example, *Scutigerella* spp.

From the order of the Thysanura, for example, *Lepisma* spp.

From the order of the Collembola, for example, *Onychiurus* spp.

From the order of the Orthoptera, for example, *Blattella* spp., *Blattella germanica*, *Blatta orientalis*, *Periplaneta* spp., *Periplaneta americana*, *Periplaneta australasiae*, *Leucophaea* spp., *Acheta* spp., *Acheta domesticus*, *Gryllotalpa* spp., *Gryllus* spp., *Gryllus bimaculatus*, *Locusta* spp., *Locusta migratoria migratorioides*, *Melanoplus* spp., *Schistocerca* spp.

From the order of the Dermaptera, for example, *Forficula* spp., *Forficula auricularia*.

From the order of Isoptera, for example, *Reticulitermes* spp., *Reticulitermes speratus*, *Coptotermes* spp., *Coptotermes formosanus*.

From the order of the Anoplura, for example, *Pediculus* spp., *Pediculus humanus humanus*, *Pediculus humanus capitis*, *Haematopinus* spp., *Linognathus* spp.

From the order of the Mallophaga, for example, *Trichodectes* spp., *Damalinea* spp.

From the order of the Thysanoptera, for example, *Frankliniella* spp., *Frankliniella fusca*, *Frankliniella occidentalis*, *Frankliniella tritici*, *Kakothrips* spp., *Hercinothrips* spp., *Scirtothrips* spp., *Scirtothrips citri*, *Scirtothrips aurantii*, *Taeniothrips* spp., *Thrips* spp., *Thrips oryzae*, *Thrips palmi*, *Thrips tabaci*.

From the order of the heteroptera, for example, *Eurygaster* spp., *Stephanitis* spp., *Lygus* spp., *Aelia* spp., *Eurydema* spp., *Dysdercus* spp., *Piesma* spp., *Piesma quadrata*, *Rhodnius prolixus*, *Triatoma* spp., *Cimex lectularius*.

From the order of the Homoptera, for example, *Aleurodes* spp., *Aleurodes brassicae*, *Aleurodes proletella*, *Bemisia* spp., *Bemisia tabaci*, *Trialeurodes* spp., *Trialeurodes vaporariorum*, *Brevicoryne* spp., *Brevicoryne brassicae*, *Cryptomyzus* spp., *Aphis* spp., *Aphis fabae*, *Aphis gossypii*, *Aphis pomi*, *Eriosoma* spp., *Hyalopterus* spp., *Phylloxera* spp., *Pemphigus* spp., *Macrosiphum* spp., *Macrosiphum avenae*, *Myzus* spp., *Myzus persicae*, *Phorodon* spp., *Phorodon humuli*, *Rhopalosiphum* spp., *Rhopalosiphum padi*, *Empoasca* spp., *Euscelis* spp., *Eulecanium* spp., *Saissetia* spp., *Aonidiella* spp., *Aonidiella aurantii*, *Aspidiotus* spp., *Nephotettix* spp., *Nephotettix cincticeps*, *Laodelphax* spp., *Laodelphax striatellus*, *Nilaparvata* spp., *Nilaparvata lugens*, *Sogatella* spp., *Pseudococcus* spp., *Psylla* spp., *Psylla mali*, *Aphrophora* spp., *Aeneolamia* spp.

From the order of the Lepidoptera, for example, *Pectinophora* spp., *Pectinophora gossypiella*, *Bupalus* spp., *Cheimatobia* spp., *Cnephasia* spp., *Hydraecia* spp., *Lithocolletis* spp., *Hyponomeuta* spp., *Plutella* spp., *Plutella xylostella*, *Malacosoma* spp., *Euproctis* spp., *Lymantria* spp., *Bucculatrix* spp., *Phytometra* spp., *Scrobipalpa* spp., *Phthorimaea* spp., *Gnorimoschema* spp., *Autographa* spp., *Evergestis* spp., *Lacanobia* spp., *Cydia* spp., *Cydia pomonella*, *Pseudociaphila* spp., *Phyllocnistis* spp., *Agrotis* spp., *Agrotis segetum*, *Agrotis ipsilon*, *Euxoa* spp., *Feltia* spp., *Earias* spp., *Heliothis* spp., *Heliothis virescens*, *Heliothis armigera*, *Heliothis zea*, *Helicoverpa* spp., *Helicoverpa armigera*, *Helicoverpa zea*, *Bombyx* spp., *Bombyx mori*, *Laphygma* spp., *Mamestra* spp., *Mamestra brassicae*, *Panolis* spp., *Prodenia* spp., *Prodenia litura*, *Spodoptera* spp., *Spodoptera littoralis*, *Spodoptera litura*, *Spodoptera exigua*, *Trichoplusia* spp., *Trichoplusia ni*, *Carpocapsa* spp., *Carpocapsa pomonella*, *Pieris* spp., *Pieris brassicae*, *Chilo* spp., *Chilo suppressalis*, *Ostrinia* spp., *Ostrinia nubilalis*, *Pyrausta* spp., *Pyrausta nubilalis*, *Ephestia* spp., *Ephestia kuehniella*, *Galleria* spp., *Galleria mellonella*, *Cacoecia* spp., *Capua* spp., *Choristoneura* spp., *Clysia* spp., *Hofmannophila* spp., *Homona* spp., *Tineola* spp., *Tinea* spp., *Tinea pellionella*, *Tortrix* spp. *Tortrix vitisana*, *Lobesia* spp., *Lobesia botrana*.

From the order of the Coleoptera, for example, *Anobium* spp., *Rhizopertha* spp., *Rhizopertha dominica*, *Bruchidius* spp., *Bruchidius obtectus*, *Acanthoscelides* spp., *Acanthoscelides obtectus*, *Hylotrupes* spp., *Aclypea* spp., *Agelastica* spp., *Leptinotarsa* spp., *Leptinotarsa decemlineata*, *Psylliodes* spp., *Chaetocnema* spp., *Cassida* spp., *Bothynoderes* spp., *Clivina* spp., *Ceutorhynchus* spp., *Ceutorhynchus assimilis*, *Phyllotreta* spp., *Apion* spp., *Sitona* spp., *Bruchus* spp., *Phaedon* spp., *Phaedon cochleariae*, *Diabrotica* spp., *Diabrotica undecimpunctata*, *Diabrotica virgifera*, *Psylloides* spp., *Epilachna* spp., *Epilachna varivestis*, *Atomaria* spp., *Atomaria linearis*, *Oryzaephilus* spp., *Anthonomus* spp., *Anthonomus grandis*, *Sitophilus* spp., *Sitophilus granarius*, *Sitophilus oryzae*, *Otiorhynchus* spp., *Otiorrhynchus sulcatus*, *Cosmopolites* spp., *Ceuthorrynchus* spp., *Hypera* spp., *Dermestes* spp., *Trogoderma* spp., *Anthrenus* spp., *Attagenus* spp., *Lyctus* spp., *Meligethes* spp., *Meligethes aeneus*, *Ptinus* spp., *Niptus* spp., *Gibbium* spp., *Tribolium* spp., *Tenebrio* spp., *Tenebrio molitor*, *Agriotes* spp., *Agriotes lineatus*, *Conoderus* spp., *Melolontha* spp., *Melolontha melolontha*, *Amphimallon* spp., *Costelytra* spp., *Costelytra zealandica*.

From the order of the Hymenoptera, for example, *Diprion* spp., *Diprion pini*, *Hoplocampa* spp., *Lasius* spp., *Monomorium* spp., *Vespa* spp.

From the order of the Diptera, for example, *Drosophila* spp., *Drosophila melanogaster*, *Chrysomyxa* spp., *Hypoderma* spp., *Tannia* spp., *Bibio* spp., *Bibio hortulanus*, *Oscinella* spp., *Oscinella frit*, *Phorbia* spp., *Pegomyia* spp., *Anastrepha* spp., *Ceratitis* spp., *Dacus* spp., *Rhagoletis* spp., *Bactrocera* spp., *Toxotrypana* spp., *Tipula* spp., *Tipula paludosa*, *Tipula oleracea*, *Dermatobia* spp., *Dermatobia hominis*, *Cordylobia* spp., *Cordylobia anthropophaga*, *Gasterophilus* spp., *Hypoderma* spp., *Cuterebra* spp., *Cochliomyia* spp., *Wohlfahrtia* spp., *Stomoxys* spp., *Calliphora* spp., *Calliphora erythrocephala*, *Gastrophilus* spp., *Hyppobosca* spp., *Lucilia* spp., *Lucilia sericata*, *Musca* spp., *Musca domestica*, *Fannia* spp., *Fannia canicularis*, *Oestrus* spp., *Tabanus* spp., *Aedes* spp., *Aedes aegypti*, *Culex* spp., *Culex quinquefasciatus*, *Anopheles* spp., *Anopheles arabiensis*.

From the order of the Siphonaptera, for example, *Xenopsylla* spp., *Xenopsylla cheopsis*, *Ctenocephalides* spp., *Ctenocephalides felis*, *Ctenocephalides canis*, *Ceratophyllus* spp., *Pulex* spp., *Pulex irritans*.

From the order of the Acarina, for example, *Acarus* spp., *Acarus siro*, *Bryobia* spp., *Bryobia praetiosa*, *Panonychus* spp., *Panonychus ulmi*, *Panonychus citri*, *Tetranychus* spp., *Tetranychus urticae*, *Eotetranychus* spp., *Oligonychus* spp., *Eutetranychus* spp., *Eriophyes* spp., *Eriophyes ribis*, *Phyllocoptruta* spp., *Phyllocoptruta oleivora*, *Tarsonemus* spp., *Argas* spp., *Argas reflexus*, *Argas persicus*, *Ornithodoros* spp., *Ornithodoros moubata*, *Dermacentor* spp., *Dermacentor marginatus*, *Hyalomma* spp., *Dermanyssus* spp., *Dermanyssus gallinae*, *Boophilus* spp., *Boophilus microplus*, *Haemaphysalis* spp., *Psoroptes* spp., *Chorioptes* spp., *Sarcoptes* spp., *Rhipicephalus* spp., *Rhipicephalus sanguineus*, *Ixodes* spp., *Ixodes ricinus*, *Amblyomma* spp.

From the class of the helminths, for example, *Schistosomen* spp., *Fasciola* spp., *Dicrocoelium* spp., *Opisthorchis* spp., *Clonorchis* spp., *Paragonimus* spp., *Taenia saginata*, *Taenia solium*, *Echinococcus granulosus*, *Echinococcus multilocularis*, *Hymenolepis nana*, *Diphyllobothrium latum*, *Onchocerca volvulus*, *Wuchereria bancrofti*, *Brugia malayi*, *Brugia timori*, *Loa Loa*, *Dracunculus medinensis*, *Enterobius vermicularis*, *Trichinella spiralis*, *Trichinella nativa*, *Trichinella britovi*, *Trichinella nelsoni*, *Trichinella pseudopsiralis*, *Ascaris* spp., *Ascaris lumbricoides*, *Trichuris trichuria*, *Ancylostoma duodenale*, *Ancylostoma ceylanicum*, *Ancylostoma braziliensis*, *Strongyloides stercoralis*, *Strongyloides fuelleborni*, *Haemonchus* spp., *Ostertagia* spp., *Trichostrongulus* spp., *Cooperia* spp., *Bunostomum* spp., *Nematodirus* spp., *Chabertia* spp., *Strongyloides* spp., *Oesophagostomum* spp., *Hyostrongulus* spp., *Ancylostoma* spp., *Dictyocaulus filaria*, *Heter-*

*akis* spp; and from the sub-group of the phytoparasitic nematodes, for example, *Meloidogyne* spp., *Meloidogyne incognita, Meloidogyne hapla, Meloidogyne javanica, Heterodera* spp., *Heterodera trifolii, Heterodera avenae, Heterodera schachtii, Heterodera glycines, Globodera* spp., *Globodera rostochiensis, Globodera pallida, Radopholus* spp., *Radopholus similis, Pratylenchus* spp., *Pratylenchus neglectus, Pratylenchus penetrans, Pratylenchus curvitatus; Tylenchulus* spp., *Tylenchulus semipenetrans, Tylenchorhynchus* spp., *Tylenchorhynchus dubius, Tylenchorhynchus claytoni, Rotylenchus* spp., *Rotylenchus robustus, Heliocotylenchus* spp., *Haliocotylenchus multicinctus, Belonoaimus* spp., *Belonoaimus longicaudatus, Longidorus* spp., *Longidorus elongatus, Trichodorus* spp., *Trichodorus primitivus, Xiphinema* spp., *Xiphinema index, Ditylenchus* spp., *Ditylenchus dipsaci, Ditylenchus destructor, Aphelenchoides* spp., *Aphelenchoides ritzemabosi, Anguina* spp., *Anguina tritici.*

The compounds of the formula (I) are also suitable for controlling animal pests, in particular arthropods, such as insects and Acarina, in rooms, specifically for controlling flies, such as, for example, from the family Muscidae (for example common house-flies, domestic flies), Calliphoridae (for example greenbottles, "death flies" (*Cynomyia mortuorum*), bluebottles) and Sarcophagidae (for example flesh-flies), mosquitoes, such as, for example, *Aedes aegypti, Anopheles arabiensis* and *Culex quinquefasciatus,* and cockroaches, such as, for example *Blattella germanica* and *Periplaneta americana.*

The invention relates to compositions, for example pesticidal compositions, preferably insecticidal, acaricidal, ixodicidal, or helminthicidal/nematicidal, particularly preferably insecticidal, acaricidal and helminthicidal/nematicidal compositions which comprise one or more compounds of the formula (I) in addition to suitable formulation auxiliaries.

In general, the compositions according to the invention comprise from 1 to 95% by weight of the active compounds of the formula (I).

For preparing the compositions according to the invention, the active compound and the other additives are combined and formulated as a suitable use form.

They can be formulated in various ways, depending on how this is predetermined by the biological and/or chemicophysical parameters. Suitable formulation possibilities are therefore:

Wettable powders (WP), emulsifiable concentrates (EC), aqueous solutions (SL), emulsions, sprayable solutions, oil- or water-based dispersions (SC), suspoemulsions (SE), dusting powders (DP), seed dressings, granules in the form of microgranules, sprayed granules, absorption granules and adsorption granules, water-dispersible granules (WG), ULV formulations, microcapsules, waxes or baits. In addition, the compositions can be employed as dips or mist applications, in the form of foams, pastes, gels, ointments, lotions, shampoos, hair-setting compositions, active-compound-containing mats (for example flat or in the form of a cushion), impregnated articles, aerosols, pressurized and non-pressurized sprays, additives to color lacques and foodstuff, and also for use as fumigants and evaporator compositions, as combustible solids (for example in the form of a cone or coil) or as combustible oils (distributed, for example, via a heated wick) and in further formulations familiar to the person skilled in the art.

These individual types of formulation are known in principle and are described, for example, in: Winnacker-Küchler, "Chemische Technologie" [Chemical Technology], Volume 7, C. Hanser Verlag Munich, 4th Edition 1986; van Falkenberg, "Pesticides Formulations", Marcel Dekker N.Y., 2nd Edition 1972–73; K. Martens, "Spray Drying Handbook", 3rd Edition 1979, G. Goodwin Ltd. London.

The necessary formulation auxiliaries, i.e. carrier and/or surface-active substances such as inert materials, surfactants, solvents and further additives, are likewise known and are described, for example, in: Watkins, "Handbook of Insecticide Dust Diluents and Carriers", 2nd Edition, Darland Books, Caldwell N.J.; H. v. Olphen, "Introduction to Clay Colloid Chemistry", 2nd Edition, J. Wiley –Sons, N.Y.; Marsden, "Solvents Guide", 2nd Edition, Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1967; Winnacker-Küchler, "Chemische Technologie" [Chemical Technology], Volume 7, C. Hanser Verlag Munich, 4th Edition 1986.

Combinations with other substances having a pesticidal action, fertilizers and/or growth regulators can be prepared on the basis of these formulations, for example in the form of a ready-to-use formulation or as a tank mix. Wettable powders are preparations which are uniformly dispersible in water and which, alongside the active compound, and in addition to a diluent or inert substance, also comprise wetting agents, for example polyethoxylated alkylphenols, polyethoxylated fatty alcohols or alkyl- or alkylphenolsulfonates, and dispersing agents, for example sodium lignosulfonate or sodium 2,2'-dinaphthylmethane-6,6'-disulfonate.

Emulsifiable concentrates are prepared by dissolving the active compound in an organic solvent, for example butanol, cyclohexanone, dimethylformamide, xylene or also higher-boiling aromatics or hydrocarbons, with the addition of one or more emulsifiers. Emulsifiers which can be used are, for example: calcium alkylaryl-sulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting powders are obtained by, for example, grinding the active compound with finely divided solid substances, for example talc, naturally occurring clays, such as kaolin, bentonite and pyrophyllite, or diatomaceous earth. Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Aerosols, sold, for example, in cans, are prepared by dissolving the active compound in water and/or organic solvents, such as, for example, acetone, deodorized petroleum, saturated $C_8$–$C_{13}$-hydrocarbons, vegetable oils, with addition of further suitable substances, such as, for example, emulsifiers, piperonyl butoxide, sorbitan monooleate, polyoxyethylene glycerol monooleate, fragrances and suitable propellents, such as, for example, carbon dioxide or butane. Ready-to-use sprays, for example for use in rooms, are obtained, for example, by mixing the active compound with odorless kerosine and antioxidants, it being possible to admix further additives, such as, for example, emulsifiers, synergists (for example piperonyl butoxide) or fragrances. Baits can be prepared, for example, by mixing the active compound with attractants and/or foodstuffs, such as, for example, sugar, and also carrier materials, such as, for example, paraffin wax.

A further advantageous embodiment for use in rooms is the use as a fumigant and an evaporator composition, which can be employed by various methods. In one of these methods, combustible solids, such as, for example, sawdust (for example pine sawdust), starch and coconut shell powder and also powdered leaves and stalks of further plants (for example pyrethrum, cedar) are, with addition of colorants and, if appropriate, fungicides, solidifed in specific forms, such as, for example, a meander, a coil or a cone, using suitable binders, and the active compound is then applied. The active compound is then distributed in the room by slow and controlled burning. In another method, mats or cushions of non-combustible fibers are used as carriers into which the active compound and, if appropriate, further substances are incorporated. These carriers are placed onto a heating plate which is heated under controlled conditions, thus releasing the active compound. In a further method, an oil is used to which the active compound is added and into which a wick consisting, for example, of cotton and/or cellulose in compressed form, is dipped, which wick releases the active compound from the oil into the room on burning. In a variant of this method, a wick of non-combustible fibers is used which is heated by an electric device, thus effecting the distribution of the active compound contained in the oil throughout the room. In the above-mentioned methods, the active compound is applied either directly or in already formulated form. Frequently, for example, colorants and fragrances are added, and also suitable fungicides for protecting the carriers made of natural products against natural decomposition.

In wettable powders, the active compound concentration is usually about 10 to 90% by weight, the remainder to make up 100% by weight comprising customary formulation constituents. In emulsifiable concentrates, the active compound concentration can be about 5 to 80% by weight. Dust-like formulations usually comprise 5 to 20% by weight of active compound, and sprayable solutions about 2 to 20% by weight. In granules, the content of active compound partly depends on whether the active compound is present in liquid or solid form and what granulating auxiliaries, fillers and the like are used. Baits generally comprise from 0.01 to 60% by weight of active compound, preferably from 0.1 to 5% by weight; aerosols generally comprise from 0.01 to 50% by weight, preferably from 0.1 to 5% by weight; ready-to-use sprays generally comprise from 0.01 to 50% by weight, preferably from 0.05 to 10% by weight. The active compound contents in fumigants and evaporator compositions are, in the case of combustible solids, generally in the range from 0.01 to 60% by weight, in the case of active-compound-comprising mats and cushions in the range from 0.01 to 60% by weight and in the case of active-compound-comprising oils in the range from 0.01 to 90% by weight.

In addition, the active compound formulations mentioned comprise, if appropriate, the particular customary tackifiers, wetting agents, dispersing agents, emulsifiers, penetration agents, solvents, fillers or carrier substances.

For use, the concentrates in the commercially available form are diluted in the customary manner, if appropriate, for example by means of water in the case of wettable powders, emulsifiable concentrates, dispersions and in some cases also microgranules. Dust-like and granular formulations as well as sprayable solutions are usually not diluted further with additional inert substances before use.

The required amount applied varies with the external conditions, such as temperature or humidity. It can vary within wide limits, for example between 0.0005 and 10.0 kg/ha or more of active substance, but is preferably between 0.001 and 5 kg/ha.

The active compounds according to the invention can be present in their commercially available formulations and in the use forms prepared from these formulations in mixtures with other active compounds, for example pesticides such as insecticides, attractants, sterilizing agents, acaricides, nematicides, fungicides, molluscides, growth-regulating substances or herbicides.

The pesticides include, for example, phosphoric acid esters, carbamates, carboxylic acid esters, formamidines, tin compounds and substances produced by microorganisms.

Preferred partners for the mixtures are:

1. from the group of phosphorus compounds acephate, azamethiphos, azinphos-ethyl, azinphos-methyl, bromophos, bromophos-ethyl, cadusafos (F-67825), chlorethoxyphos, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, dimethoate, disulfoton, EPN, ethion, ethoprophos, etrimfos, famphur, fenamiphos, fenitriothion, fensulfothion, fenthion, fonofos, formothion, fosthiazate (ASC-66824), heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosphocarb (BAS-301), phosmet, phosphamidon, phoxim, pirimiphos, primiphos-ethyl, pirimiphos-methyl, profenofos, propaphos, proetamphos, prothiofos, pyraclofos, pyridapenthion, quinalphos, sulprofos, temephos, terbufos, tebupirimfos, tetrachlorvinphos, thiometon, triazophos, trichlorphon, vamidothion;

2. from the group of carbamates alanycarb (OK-135), aldicarb, 2-sec-butylphenyl methylcarbamate (BPMC), carbaryl, carbofuran, carbosulfan, cloethocarb, benfuracarb, ethiofencarb, furathiocarb, HCN-801, isoprocarb, methomyl, 5-methyl-m-cumenyl butyryl (methyl)carbamate, oxamyl, pirimicarb, propoxur, thiodicarb, thiofanox, 1-methylthio(ethylideneamino) N-methyl-N-(morpholinothio)carbamate (UC 51717), triazamate;

3. from the group of carboxylic acid esters acrinathrin, allethrin, alphametrin, 5-benzyl-3-furylmethyl (E)-(1R)-cis-2,2-di-methyl-3-(2-oxothiolan-3-ylidenemethyl)cyclopropanecarboxylate, beta-cyfluthrin, beta-cypermethrin, bioallethrin, bioallethrin ((S)-cyclopentyl isomer), bioresmethrin, bifenthrin, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyfluthrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), imiprothrin (S-41311), lambda-cyhalothrin, permethrin, pheothrin ((R) isomer), prallethrin, pyrethrins (natural products), resmethrin, tefluthrin, tetramethrin, theta-cypermethrin (TD-2344), tralomethrin, transfluthrin and zeta-cypermethrin (F-56701);

4. from the group of amidines amitraz, chlordimeform;

5. from the group of tin compounds cyhexatin, fenbutatin oxide;

6. others abamectin, ABG-9008, acetamiprid, *Anagrapha falcitera*, AKD-1022, AKD-3059, ANS-118, *Bacillus thuringiensis, Beauveria bassianea*, bensultap, bifenazate (D-2341), binapacryl, BJL-932, bromopropylate, BTG-504, BTG-505, buprofezin, camphechlor, cartap, chlorobenzilate, chlorfenapyr, chlorfluazuron, 2-(4-chlorophenyl)-4,5-diphenylthiophene (UBI-T 930), chlorfentezine, chromafenozide (ANS-118), CG-216, CG-217, CG-234, A-184699, 2-naphthylmethyl cyclopropanecarboxylate (Ro12-0470), cyromazin, diacloden (thiamethoxam), diafenthiuron, N-(3,5-dichloro-4-(1,1,2,3,3,3-hexafluoro-1-propyloxy)phenyl)carbamoyl)-2-chlorobenzocarboxamide acid ethyl ester, DDT, dicofol, diflubenzuron, N-(2, 3-dihydro-3-methyl-1,3-thiazol-2-ylidene)-2,4-xylidine, dinobuton, dinocap, diofenolan, DPX-062, emamectinbenzoate (MK-244), endosulfan, ethiprole (sulfethiprole), ethofenprox, etoxazole (YI-5301), fenazaquin, fenoxycarb, fipronil, fluazuron, flumite (flufenzine, SZI-121), 2-fluoro-5-(4-(4-ethoxyphenyl)-4-methyl-1-pentyl) diphenyl ether (MTI 800), granulosis and nuclear polyhedrosis viruses, fenpyroximate, fenthiocarb, flubenzimine, flucycloxuron, flufenoxuron, flufenprox (ICI-A5683), fluproxyfen, gamma-HCH, halofenozide (RH-0345), halofenprox (MTI-732), hexaflumuron (DE__473), hexythiazox, HOI-9004, hydramethylnon (AC 217300), lufenuron, imidacloprid, indoxacarb (DPX-MP062), kanemite (AKD-2023), M-020, MTI-446, ivermectin, M-020, methoxyfenozide (Intrepid, RH-2485), milbemectin, NC-196, neemgard, nitenpyram (TI-304), 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), pyriproxyfen (S-71639), NC-196, NC-1111, NNI-9768, novaluron (MCW-275), OK-9701, OK-9601, OK-9602, propargite, pymetrozine, pyridaben, pyrimidifen (SU-8801), RH-0345, RH-2485, RYI-210, S-1283, S-1833, SB7242, SI-8601, silafluofen, silomadine (CG-177), spinosad, SU-9118, tebufenozide, tebufenpyrad (MK-239), teflubenzuron, tetradifon, tetrasul, thiacloprid, thiocyclam, TI-435, tolfenpyrad (OMI-88), triazamate (RH-7988), triflumuron, verbutin, vertalec (Mykotal), YI-5301.

The abovementioned components are known active substances, many of which are described in C D S Tomlin (Editor), The Pesticide Manual, 12th edition, The British Crop Protection Council, Farnham, UK, 2000.

The active compound content of the use forms prepared from the commercially available formulations can be from 0.00000001 to 95% by weight of active compound, preferably between 0.00001 and 1% by weight. The active compounds are used in a customary manner appropriate for the use forms.

The compounds of the formula (I) can be employed in their commercially available formulations, also in combination with fungicides. These fungicides are generally active compounds which are described in C D S Tomlin (Editor), The Pesticide Manual, 12th edition, The British Crop Protection Council, Farnham, UK, 2000. Appiication is carried out in a customary manner adapted to suit the use forms, for example in the control of pathogenic fungi by applying a fungicidally effective amount of a compound according to the invention or a composition according to the invention to these fungi or to the plants, areas or substrates infected with them, or to seed.

The compounds of the formula (I) can also be employed for controlling harmful organisms in crops of known or yet to be developed genetically engineered plants. As a rule, the transgenic plants are distinguished by particular advantageous properties, for example by resistances to certain crop protection agents, resistances to plant diseases or pathogens of plant diseases such as certain insects or microorganisms such as fungi, bacteria or viruses. Other particular properties relate, for example, to the harvested material with regard to quantity, quality, storage properties, composition and specific constituents. Thus, transgenic plants with an elevated starch content or altered starch quality, or those with a different fatty acid spectrum of the harvested material, are known.

The use in economically important transgenic crops of useful plants and ornamentals, for example, cereals such as wheat, barley, rye, oats, millet, rice, manioc and corn or else crops of sugar beet, cotton, soya, oilseed rape, potatoes, tomatoes, peas and other types of vegetables is preferred.

When being used in transgenic crops, in particular those in which the plants express an insecticide, effects are frequently found (in addition to the pesticidal effects which can be observed in other crops) which are specific to application in the transgenic crop in question, for example an altered or specifically widened spectrum of pests which can be controlled, or altered application rates which can be used for application.

The compounds of the formula (I) according to the invention or the compositions comprising them are used, for example, in agriculture, in horticulture, in forests and in the protection of materials and food. They are preferably used in economically important crops of useful plants and ornamentals, for example of cereals, such as wheat, barley, rye, oats, millet, rice, manioc and corn, or else crops of sugar beet, cotton, soya, oilseed rape, potatoes, tomatoes, peas and other types of vegetables.

The use of the compounds according to the invention embraces, in addition to direct application onto the harmful organisms, any other application in which compounds of the formula (I) act on the harmful organisms. Such indirect applications can, for example, be the use of compounds which, for example in the soil, the plant or the harmful organism, decompose into compounds of the formula (I) or are degraded into compounds of the formula (I).

The use according to the invention of compounds of the formula (I) or compositions comprising them, for example as insecticide, acaricide or helminthicide/nematicide, also includes the case where the compound of the formula (I) or its salt is formed from a precursor only after application, for example in the harmful organism, in a plant or in the soil.

In addition to the above mentioned and customary application methods, the active compounds of the formula (I) according to the invention have excellent systemic action. Accordingly, the active compounds can also be introduced into the plants via parts of the plant, both below ground and above ground (for example root, stolons, stem, trunk, leaf), if the active compounds are applied, in liquid or solid form, on or into the plant or into the direct vicinity of the plant (for example granules in soil application, application in flooded rice paddies, trunk injection in the case of trees, stem bandages in the case of perennial plants).

In addition, the active compounds according to the invention are particularly suitable for the treatment of vegetative and generative plant propagation material, such as, for example, of seeds, for example of cereals, vegetables, cotton, rice, sugar beet and other crops and ornamental plants, of bulbs, seedlings and tubers of other crops and ornamental plants which are propagated vegetatively. The treatment can be carried out before sowing or before planting (for example by special seed coating techniques, by dressing in liquid or solid form or as a seed-box treatment), during sowing or planting or after sowing or planting by special application techniques (for example furrow treatment). The amount of active compound used can vary within a relatively large range, depending on the application. In general, the application rates are between 1 g and 10 kg of active compound per hectare of soil surface. The treatment methods for plant propagation material and the plant propagation material treated in this manner are also provided by the invention.

The active compounds according to the invention are also suitable for use in the veterinary field, preferably for controlling endoparasites and ectoparasites, and in the field of animal husbandry. The active compounds according to the invention can be applied in a known manner, such as by oral administration in the form of, for example, tablets, capsules, drinks or granules, by dermal application in the form of, for example, dipping, spraying, pouring on and spotting on, and dusting, and by parenteral administration in the form of, for example, an injection.

Accordingly, the compounds of the formula (I) according to the invention can also be employed particularly advantageously in livestock keeping (for example cattle, sheep, pigs and poultry such as chicken, geese and the like). In a preferred embodiment of the invention, the compounds, if appropriate in suitable formulations, are administered orally to the animals, if appropriate together with the drinking water or feed. Since excretion in the feces is efficient, the development of insects in the animals' feces can be prevented very easily in this manner. The dosages and formulations which are suitable in each case depend, in particular on the species and the developmental stage of the productive livestock and also on the risk of infestation and can be established and determined readily by customary methods. In cattle the compounds can be employed at dosages of, for example, from 0.01 to 1 mg/kg of body weight.

In addition, the compounds according to the invention are also suitable for use in technical fields, for example as wood preservatives, as preservatives in paints, in cooling lubricants for metal working, or as preservatives in drilling and cutting oils.

Further preferred areas of use are the protection of stored products and materials, the hygiene sector and the domestic sector where, in a preferred embodiment of the invention, the composition according to the invention is used in the buildings in question and, if appropriate, combined with further measures, such as, for example, sticky boards or traps. Here, too, suitable dosages and formulations depend in particular on the type and the intensity of the risk of infestation and can be established and determined readily by customary methods.

The invention is illustrated by the examples below. The Preparation Examples may also comprise prior-art compounds which serve to illustrate the preparation process for the compounds according to the invention. Prior-art compounds, listed in the tables below in addition to compounds according to the invention, are also used in the process according to the invention.

A. CHEMICAL EXAMPLES

Example 1

1-(3-o-Tolyl-2-propynyl)piperidine

A mixture of 2-iodotoluene (6.54 g), N-(2-propynyl)piperidine (3.69 g), dichlorobis(triphenylphosphino)palladium(II) (0.05 g) and copper(I) iodide (0.1 g) in dry diethylamine (50 ml) was heated under reflux for 5 hours. The solvent was removed under reduced pressure and the residue was taken up in diethyl ether and washed with water. The organic phase was dried over magnesium sulfate and concentrated completely under reduced pressure. Distillation of the residue under reduced pressure gave 3.98 g of an oil of boiling point 96–98° C./0.08 mm Hg.

Preparation of the starting material 1-(2-propynyl)piperidine:

With stirring, a solution of 2-propynyl chloride (40.31 g) in dry methanol (50 ml) was added dropwise to a solution of piperidine (92.14 g) in dry methanol (100 ml). The mixture was stirred at 25° C. for 3 hours and then filtered. The filtrate was concentrated under reduced pressure and the residue was distilled (boiling point: 163–165° C./atmospheric pressure).

Example 2

1-(4-Methoxyphenyl-2-propynyl)piperidine hydrochloride

When 2-iodotoluene was replaced by 4-iodoanisole, the process of Example 1 gave a crude product to which excess hydrochloric acid in methanol was added. Removal of the solvent gave, after crystallization from isopropanol, colorless needles of melting point 223–225° C.

Example 3

1-[3-(4-Methoxyphenyl)-2-propynyl]piperidine

The product from Example 2 was dissolved in water and the solution was made alkaline using 2N aqueous sodium hydroxide solution and extracted with diethyl ether. The ether extracts were dried using magnesium sulfate, and the solvent was then removed and the residue was distilled under reduced pressure. This gave an oil of boiling point 126–128° C./0.1 mm Hg.

Example 4

1-[3-(3-Fluorophenyl)-2-propynyl]-4-methylpiperidine

A mixture of 3-fluoroiodobenzene (8.88 g), 4-methyl-1-(2-propynyl)piperidine (6.80 g), palladium acetate (0.045 g), tri-o-toloylphosphine (0.24 g) and copper(I) iodide (0.1 g) in dry diethylamine (50 ml) was heated under reflux for 5 hours. The solvent was removed under reduced pressure and the residue was taken up in diethyl ether and washed with water. The organic phase was dried over magnesium sulfate and the solvent was removed under reduced pressure. Distillation of the residue under reduced pressure gave an oil (5.20 g) of boiling point 105° C./0.07 mm Hg.

Preparation of the starting material 4-methyl-1-(2-propynyl)piperidine: At 0–5° C., propargyl bromide (12.01 g) was added dropwise with stirring to a suspension of 4-methylpiperidine (10.0 g) and potassium carbonate (13.96 g) in dry acetone (80 ml). The mixture was stirred at 50° C. for 6 hours and then filtered. The filtrate was concentrated under reduced pressure and the residue was taken up in dichloromethane. The organic phase was washed with water (3×15 ml), dried with sodium sulfate and concentrated under reduced pressure. Distillation of the residue under reduced pressure gave 12.73 g of an oil of boiling point 60° C./16 mm Hg.

Example 5

1-(3-phenyl-2-propynyl)piperidine

With stirring, a solution of phenylacetylene (10.2 g) in dioxane (10 ml), a solution of piperidine (13.3 g) in dioxane (10 ml) and copper(I) chloride (0.1 g) were added successively to a suspension of paraformaldehyde (3.6 g) in dioxane (10 ml). The mixture was heated under reflux for 6 hours, allowed to cool to 25° C. and acidified using 20% strength hydrochloric acid. The solution was washed with diethyl ether and the aqueous phase was made alkaline using 50% strength aqueous sodium hydroxide solution and extracted with diethyl ether (3×100 ml). The organic phase was dried with magnesium sulfate and concentrated completely. Distillation of the residue under reduced pressure gave an oil (13.0 g) of boiling point 95° C./0.045 mm Hg.

Example 6

1-[3-(3,5-Bistrifluoromethylphenyl)-2-propynyl]piperidine

A mixture of 1-(3,5-bistrifluoromethylphenyl)-3-bromoprop-1-yne (2.53 g), piperidine (5 ml) and anhydrous potassium carbonate (5 g) in dry acetone (50 ml) was heated at reflux with stirring for 18 h. Removal of the solvent under reduced pressure and distillation of the residue under reduced pressure gave 2.26 g of an oil of boiling point 95° C./0.025 mm Hg.

Example 7

1-[3-(3,5-Bistrifluoromethylphenyl)-2-propynyl]piperidine hydrochloride

An excess of dry HCl gas was passed through a solution of 1-(3,5-bistrifluoromethylphenyl)-3-piperidinoprop-1-yne (2.26 g) in dry diethyl ether (200 ml). Filtration, washing (diethyl ether) and drying of the resulting white precipitate gave 2.16 g of a fine white powder of melting point 214.5° C.

The compounds of the tables below were obtained analogously to Examples 1 to 7.

In the tables, the following abbreviations are used

L¹ 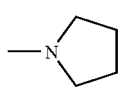

L² 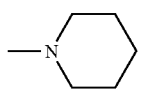

-continued
| | |
|---|---|
| L³ | 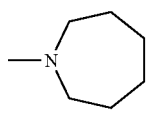 |
| L⁴ | 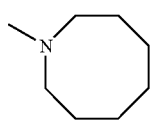 |
| L⁵ | 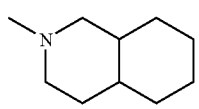 |
| L⁶ | 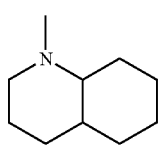 |
| L⁷ | 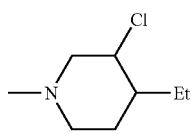 |
| L⁸ | 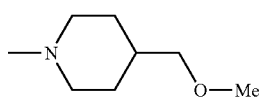 |
| L⁹ | 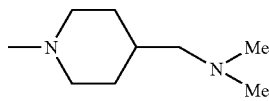 |
| L¹⁰ | 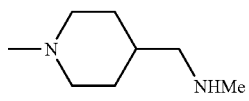 |
| L¹¹ | 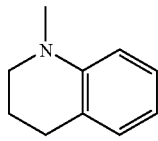 |
| L¹² | 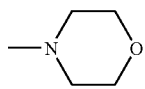 |
| L¹³ | 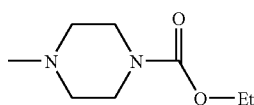 |
| L¹⁴ | 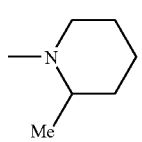 |
| L¹⁵ | 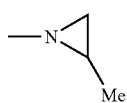 |

-continued
| | |
|---|---|
| L[16] | 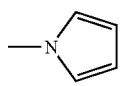 |
| L[17] | 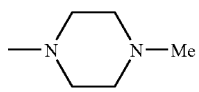 |
| L[18] | 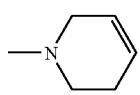 |
| L[19] | 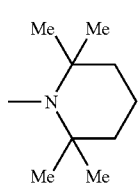 |
| L[20] | 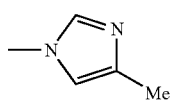 |
| L[21] | 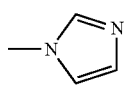 |
| L[22] | 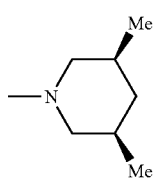 |
| L[23] | 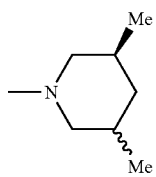 |
| L[24] | 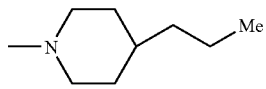 |
| L[25] | 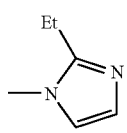 |
| L[26] | 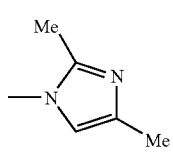 |
| L[27] | 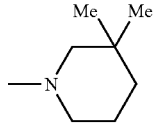 |

-continued
L²⁸ 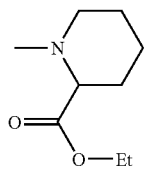
L²⁹ 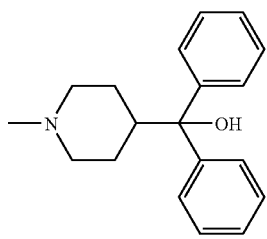
L³⁰ 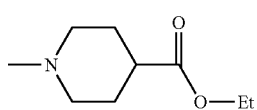
L³¹ 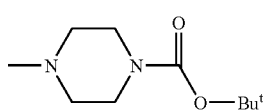
L³² 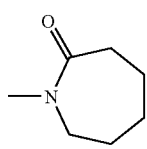
L³³ 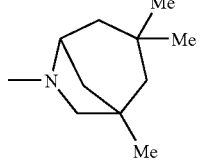
L³⁴ 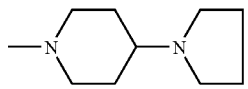
L³⁵ 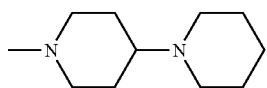
L³⁶ 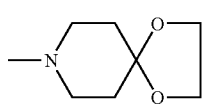
L³⁷ 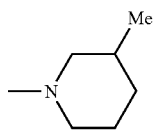
L³⁸ 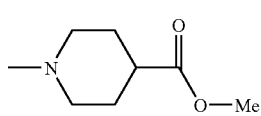

-continued
L39 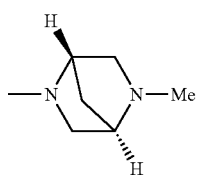
L40 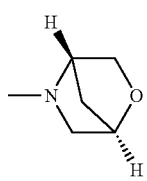
L41 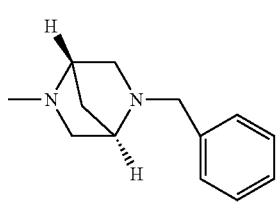
L42 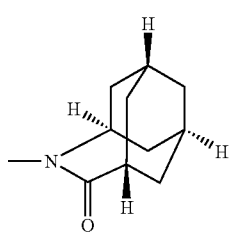
L43 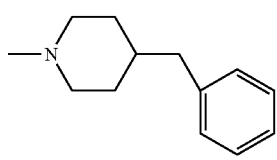
L44 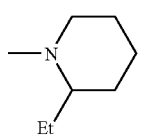
L45 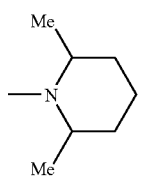
L46 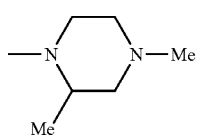
L47 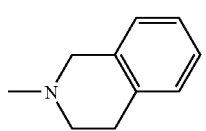

-continued
| | |
|---|---|
| $L^{48}$ | 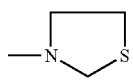 |
| $L^{49}$ | 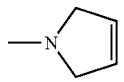 |
| $L^{50}$ |  |
| $L^{51}$ | 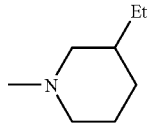 |
| $L^{52}$ |  |
| $L^{53}$ | 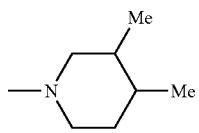 |
| $L^{54}$ | 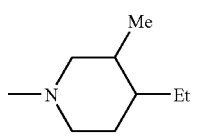 |
| $L^{55}$ | 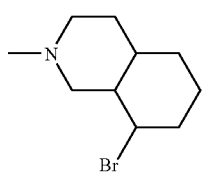 |
| $L^{56}$ | 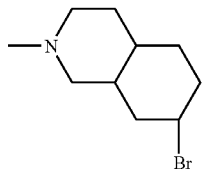 |
| $L^{57}$ | 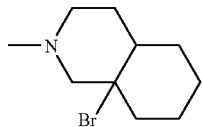 |
| $L^{58}$ | 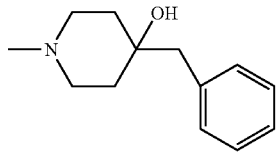 |

-continued
L59 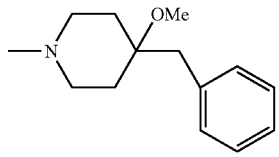
L60 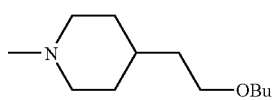
L61 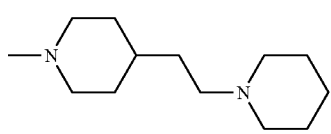
L62 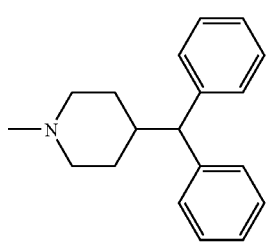
L63 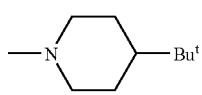
L64 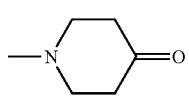
L65 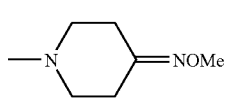
L66 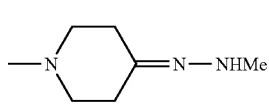
L67 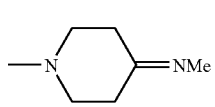
L68 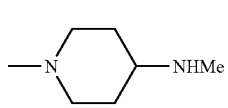
L69 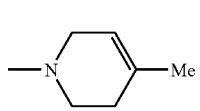
L70 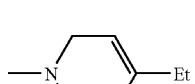
L71 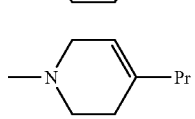

-continued
| | |
|---|---|
| L⁷² | 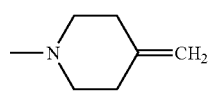 |
| L⁷³ | 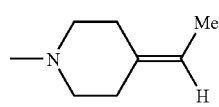 |
| L⁷⁴ | 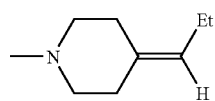 |
| L⁷⁵ | 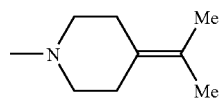 |
| L⁷⁶ | 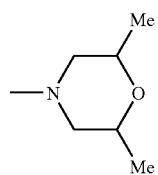 |
| L⁷⁷ | 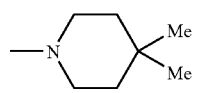 |
| L⁷⁸ | 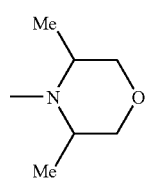 |
| L⁷⁹ | 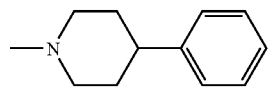 |
| L⁸⁰ | 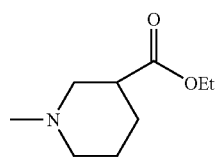 |
| L⁸¹ | 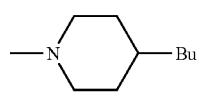 |
| L⁸² | 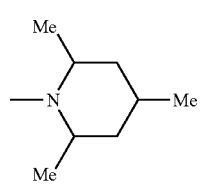 |

-continued
| | |
|---|---|
| L83 | 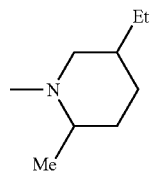 |
| L84 | 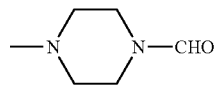 |
| L85 | 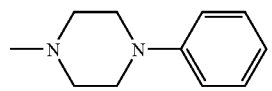 |
| L86 | 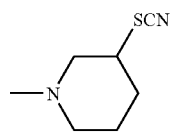 |
| L87 | 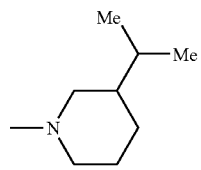 |
| L88 | 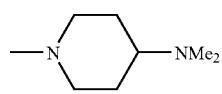 |
| L89 | 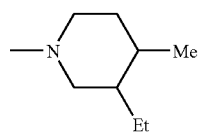 |
| L90 |  |
| L91 | 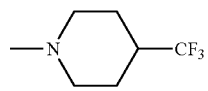 |
| L92 |  |
| L93 | 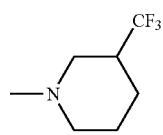 |
$T^i =$ 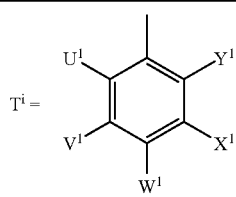

-continued

| $T^i$ | $U^1$ | $V^1$ | $W^1$ | $X^1$ | $Y^1$ |
|---|---|---|---|---|---|
| $T^1$ | H | H | H | H | H |
| $T^2$ | Cl | H | H | H | H |
| $T^3$ | H | Cl | H | H | H |
| $T^4$ | H | H | Cl | H | H |
| $T^5$ | Cl | Cl | H | H | H |
| $T^6$ | Cl | H | Cl | H | H |
| $T^7$ | Cl | H | H | Cl | H |
| $T^8$ | Cl | H | H | H | Cl |
| $T^9$ | H | Cl | Cl | H | H |
| $T^{10}$ | H | Cl | H | Cl | H |
| $T^{11}$ | H | Cl | H | H | Cl |
| $T^{12}$ | Cl | Cl | Cl | H | H |
| $T^{13}$ | Cl | Cl | H | Cl | H |
| $T^{14}$ | Cl | Cl | H | H | Cl |
| $T^{15}$ | Cl | H | Cl | Cl | H |
| $T^{16}$ | Cl | H | Cl | H | Cl |
| $T^{17}$ | Cl | Cl | Cl | Cl | H |
| $T^{18}$ | Cl | Cl | Cl | H | Cl |
| $T^{19}$ | Cl | Cl | H | Cl | Cl |
| $T^{20}$ | Cl | Cl | Cl | Cl | Cl |
| $T^{21}$ | F | H | H | H | H |
| $T^{22}$ | H | F | H | H | H |
| $T^{23}$ | H | H | F | H | H |
| $T^{24}$ | F | F | H | H | H |
| $T^{25}$ | F | H | F | H | H |
| $T^{26}$ | F | H | H | F | H |
| $T^{27}$ | F | H | H | H | F |
| $T^{28}$ | H | F | F | H | H |
| $T^{29}$ | H | F | H | F | H |
| $T^{30}$ | H | F | H | H | F |
| $T^{31}$ | $CF_3$ | H | H | H | H |
| $T^{32}$ | H | $CF_3$ | H | H | H |
| $T^{33}$ | H | H | $CF_3$ | H | H |
| $T^{34}$ | $CF_3$ | $CF_3$ | H | H | H |
| $T^{35}$ | $CF_3$ | H | $CF_3$ | H | H |
| $T^{36}$ | $CF_3$ | H | H | $CF_3$ | H |
| $T^{37}$ | $CF_3$ | H | H | H | $CF_3$ |
| $T^{38}$ | H | $CF_3$ | $CF_3$ | H | H |
| $T^{39}$ | H | $CF_3$ | H | $CF_3$ | H |
| $T^{40}$ | H | $CF_3$ | H | H | $CF_3$ |
| $T^{41}$ | H | $CF_3$ | $CF_3$ | $CF_3$ | H |
| $T^{42}$ | Cl | $CF_3$ | H | H | H |
| $T^{43}$ | Cl | H | $CF_3$ | H | H |
| $T^{44}$ | Cl | H | H | $CF_3$ | H |
| $T^{45}$ | Cl | H | H | H | $CF_3$ |
| $T^{46}$ | H | Cl | $CF_3$ | H | H |
| $T^{47}$ | H | Cl | H | $CF_3$ | H |
| $T^{48}$ | H | Cl | H | H | $CF_3$ |
| $T^{49}$ | H | H | Cl | $CF_3$ | H |
| $T^{50}$ | H | H | Cl | H | $CF_3$ |
| $T^{51}$ | H | H | H | Cl | $CF_3$ |
| $T^{52}$ | Me | Cl | H | H | H |
| $T^{53}$ | H | Cl | Me | H | H |
| $T^{54}$ | H | Cl | H | Me | H |
| $T^{55}$ | H | Me | Cl | H | H |
| $T^{56}$ | Me | H | Cl | H | H |
| $T^{51}$ | H | F | Cl | H | H |
| $T^{58}$ | H | F | H | Cl | H |
| $T^{59}$ | H | Cl | F | H | H |
| $T^{60}$ | H | $NO_2$ | H | H | H |
| $T^{61}$ | H | H | $NO_2$ | H | H |
| $T^{62}$ | H | CN | H | H | H |
| $T^{63}$ | H | H | CN | H | H |
| $T^{64}$ | H | $NO_2$ | Cl | H | H |
| $T^{65}$ | H | $NO_2$ | H | Cl | H |
| $T^{66}$ | H | Cl | $NO_2$ | H | H |
| $T^{67}$ | H | CN | Cl | H | H |
| $T^{68}$ | H | CN | H | Cl | H |
| $T^{69}$ | H | Cl | CN | H | H |
| $T^{70}$ | H | $NO_2$ | $CF_3$ | H | H |
| $T^{71}$ | H | $NO_2$ | H | $CF_3$ | H |
| $T^{72}$ | H | $CF_3$ | $NO_2$ | H | H |
| $T^{73}$ | H | CN | $CF_3$ | H | H |
| $T^{74}$ | H | CN | H | $CF_3$ | H |
| $T^{75}$ | H | $CF_3$ | CN | H | H |
| $T^{76}$ | H | Me | H | H | H |
| $T^{77}$ | H | H | Me | H | H |

-continued

| | | | | | |
|---|---|---|---|---|---|
| T78 | COOMe | H | H | H | H |
| T79 | H | COOMe | H | H | H |
| T80 | H | H | COOMe | H | H |
| T81 | H | Cl | Cl | OMe | H |
| T82 | H | Cl | OMe | Cl | H |
| T83 | H | CF3 | OMe | CF3 | H |
| T84 | H | CF3 | OMe | Cl | H |
| T85 | OMe | H | H | H | H |
| T86 | H | OMe | H | H | H |
| T87 | H | H | OMe | H | H |
| T88 | Me | H | H | H | H |
| T89 | H | SMe | H | H | H |
| T90 | H | H | SMe | H | H |
| T91 | H | Ph | H | H | H |
| T92 | H | Ph | Cl | H | H |
| T93 | H | Ph | CF3 | H | H |
| T94 | H | H | Ph | H | H |
| T95 | H | Cl | Ph | H | H |
| T96 | H | CF3 | Ph | H | H |
| T97 | H | Cl | Ph | Cl | H |
| T98 | H | CF3 | Ph | CF3 | H |
| T99 | H | H | HC=CH—CF3 | H | H |
| T100 | H | Cl | HC=CH—CF3 | H | H |
| T101 | H | HC=CH—CF3 | H | H | H |
| T102 | H | HC=CH—CF3 | Cl | H | H |
| T103 | H | H | OEt | H | H |
| T104 | H | H | Et | H | H |
| T105 | H | Me | F | H | H |
| T106 | Me | H | F | H | H |
| T107 | Cl | H | H | Me | H |
| T108 | Me | H | H | F | H |
| T109 | H | OC(O)Pr | H | H | H |
| T110 | Me | H | H | Cl | H |
| T111 | Me | H | Me | H | H |
| T112 | Cl | H | H | H | Me |
| T113 | Me | Me | H | H | H |
| T114 | Me | H | H | H | Me |
| T115 | Et | H | H | H | H |
| T116 | H | Me | Me | H | H |
| T111 | H | SO2Me | H | H | H |
| T118 | Pr$^i$ | H | H | H | H |
| T119 | F | H | F | H | F |
| T120 | EtO | H | H | H | H |
| T121 | F | H | H | F | H |
| T122 | F | H | F | H | H |
| T123 | H | Cl | Cl | Me | H |
| T124 | H | H | Pr$^i$ | H | H |
| T125 | F | F | F | F | F |
| T126 | Me | H | H | Me | H |
| T127 | H | H | OPh | H | H |
| T128 | H | H | C(O)Me | H | H |
| T129 | H | | OCH2O | H | H |
| T130 | H | Me | H | Me | H |
| T131 | H | CF3 | H | OMe | H |
| T132 | H | F | Me | H | H |
| T133 | H | H | 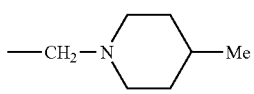 | H | H |
| T134 | H | Cl | F | Cl | H |
| T135 | H | CF3 | COOMe | H | H |
| T136 | H | OMe | OMe | H | H |
| T137 | H | Cl | Cl | Cl | H |
| T138 | H | NO2 | H | NO2 | H |
| T139 | H | CF3 | H | NO2 | H |
| T140 | Cl | H | CF3 | H | Cl |
| T141 | H | C(O)Me | H | H | H |
| T142 | H | H | (2-Cl,5-CF3)Ph | H | H |
| T143 | H | H | (4-CF3)Ph | H | H |
| T144 | H | H | (3-Cl)Ph | H | H |
| T145 | H | H | (2-Cl)Ph | H | H |
| T146 | H | H | (3-Me,5-Me)Ph | H | H |
| T147 | H | H | (4-OMe)Ph | H | H |
| T148 | H | H | (2-Cl,4-Cl)Ph | H | H |
| T149 | H | H | (3-F,5-NO2)Ph | H | H |
| T150 | H | H | (3-CO2Et)Ph | H | H |

-continued
| | | | | | |
|---|---|---|---|---|---|
| T¹⁵¹ | H | H | (2-Me,5-NO₂)Ph | H | H |
| T¹⁵² | H | H | (2-Cl,3-Cl)Ph | H | H |
| T¹⁵³ | H | H | (3-CF₃)Ph | H | H |
| T¹⁵⁴ | H | H | (2-Me)Ph | H | H |
| T¹⁵⁵ | H | H | 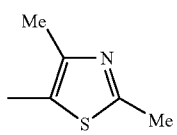 | H | H |
| T¹⁵⁶ | H | H | 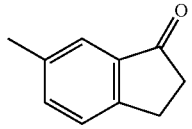 | H | H |
| T¹⁵⁷ | H | H | 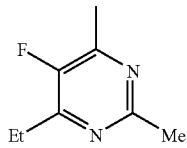 | H | H |
| T¹⁵⁸ | H | H | 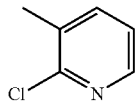 | H | H |
| T¹⁵⁹ | H | H | 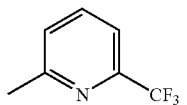 | H | H |
| T¹⁶⁰ | H | H | 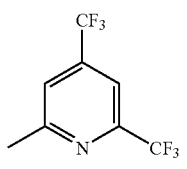 | H | H |
| T¹⁶¹ | H | H | (4-CN)Ph | H | H |
| T¹⁶² | H | H | 2-thienyl | H | H |
| T¹⁶³ | H | H | (2-F,6-F)Ph | H | H |
| T¹⁶⁴ | H | H | 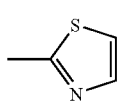 | H | H |
| T¹⁶⁵ | H | H | 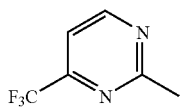 | H | H |
| T¹⁶⁶ | H | H | (4-OCH₂CF₃)Ph | H | H |
| T¹⁶⁷ | H | H | (4-Me)Ph | H | H |
| T¹⁶⁸ | H | F | Br | H | H |
| T¹⁶⁹ | H | CF₃ | Br | H | H |
| T¹⁷⁰ | H | (4-CF₃)Ph | H | H | H |
| T¹⁷¹ | H | (3-CF₃,5-CF₃)Ph | H | H | H |
| T¹⁷² | H | (3-Cl)Ph | H | H | H |
| T¹⁷³ | H | (4-NO₂)Ph | H | H | H |
| T¹⁷⁴ | H | 1-Naphthyl | H | H | H |
| T¹⁷⁵ | H | (4-Cl)Ph | H | H | H |

-continued

| | | | | | |
|---|---|---|---|---|---|
| T¹⁷⁶ | H | ![pyrimidine with Et, Me] | H | H | H |
| T¹⁷⁷ | H | ![2,3-dichloro-5-methylpyridinyl] | H | H | H |
| T¹⁷⁸ | H | ![5-chlorothienyl] | H | H | H |
| T¹⁷⁹ | H | (4-CN)Ph | H | H | H |
| T¹⁸⁰ | H | ![thiazolyl] | H | H | H |
| T¹⁸¹ | H | F | (4-F)Ph | H | H |
| T¹⁸² | H | F | Et | H | H |
| T¹⁸³ | H | CF₃ | Et | H | H |
| T¹⁸⁴ | H | CF₃ | H | Me | H |
| T¹⁸⁵ | H | Cl | OCF₂CHFCl | Cl | H |
| T¹⁸⁶ | H | CF₃ | Me | H | H |
| T¹⁸⁷ | H | CF₃ | F | H | H |
| T¹⁸⁸ | F | Cl | F | H | H |
| T¹⁸⁹ | H | F | (4-OMe)Ph | H | H |
| T¹⁹⁰ | H | F | (4-Me)Ph | H | H |
| T¹⁹¹ | H | F | (3-Cl,4-F)Ph | H | H |
| T¹⁹² | H | F | (4-CF₃)Ph | H | H |
| T¹⁹³ | H | F | (3,4-OCH₂CH₂O)Ph | H | H |
| T¹⁹⁴ | H | F | [4-C(O)Me]Ph | H | H |
| T¹⁹⁵ | H | F | (4-OCF₃)Ph | H | H |
| T¹⁹⁶ | H | F | (4-tBu)Ph | H | H |
| T¹⁹⁷ | H | F | (4-Cl)Ph | H | H |
| T¹⁹⁸ | H | F | (3-Me)Ph | H | H |
| T¹⁹⁹ | H | F | (3-Cl)Ph | H | H |
| T⁶⁰⁰ | H | CF₃ | (4-SMe)Ph | H | H |
| T⁶⁰¹ | H | CF₃ | 3-thienyl | H | H |
| T⁶⁰² | H | CF₃ | (4-CF₃)Ph | H | H |
| T⁶⁰³ | H | CF₃ | (4-OCF₃)Ph | H | H |
| T⁶⁰⁴ | H | CF₃ | [4-C(O)Me]Ph | H | H |
| T⁶⁰⁵ | H | CF₃ | (4-Cl)Ph | H | H |
| T⁶⁰⁶ | H | CF₃ | 1-Naphthyl | H | H |
| T⁶⁰⁷ | H | CF₃ | (2-F)Ph | H | H |
| T⁶⁰⁸ | H | CF₃ | (2-Cl)Ph | H | H |
| T⁶⁰⁹ | H | F | 3-thienyl | H | H |

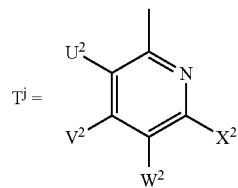

$T^j =$

| $T^j$ | $U^2$ | $V^2$ | $W^2$ | $X^2$ |
|---|---|---|---|---|
| T²⁰⁰ | Cl | H | CF₃ | H |
| T²⁰¹ | H | Cl | CF₃ | H |
| T²⁰² | H | H | CF₃ | Cl |
| T²⁰³ | H | CF₃ | H | Cl |
| T²⁰⁴ | CF₃ | H | H | Cl |
| T²⁰⁵ | Cl | CF₃ | H | H |
| T²⁰⁶ | Cl | H | H | CF₃ |
| T²⁰⁷ | H | Cl | H | CF₃ |
| T²⁰⁸ | H | H | Cl | CF₃ |
| T²⁰⁹ | CF₃ | Cl | H | H |

-continued

| | | | | |
|---|---|---|---|---|
| $T^{210}$ | H | $CF_3$ | Cl | H |
| $T^{211}$ | $CF_3$ | H | Cl | H |
| $T^{212}$ | Br | H | H | H |
| $T^{213}$ | H | Br | H | H |
| $T^{214}$ | H | H | Br | H |
| $T^{215}$ | H | H | H | Br |
| $T^{216}$ | $CF_3$ | H | H | H |
| $T^{217}$ | H | $CF_3$ | H | H |
| $T^{218}$ | H | H | $CF_3$ | H |
| $T^{219}$ | H | H | H | $CF_3$ |
| $T^{220}$ | H | H | H | H |
| $T^{221}$ | CN | H | H | H |
| $T^{222}$ | H | CN | H | H |
| $T^{223}$ | H | H | CN | H |
| $T^{224}$ | H | H | H | CN |
| $T^{225}$ | $NO_2$ | H | H | H |
| $T^{226}$ | H | $NO_2$ | H | H |
| $T^{227}$ | H | H | $NO_2$ | H |
| $T^{228}$ | H | H | H | $NO_2$ |
| $T^{229}$ | $CF_3$ | $CF_3$ | H | H |
| $T^{230}$ | $CF_3$ | H | $CF_3$ | H |
| $T^{231}$ | $CF_3$ | H | H | $CF_3$ |
| $T^{232}$ | H | $CF_3$ | $CF_3$ | H |
| $T^{233}$ | H | $CF_3$ | H | $CF_3$ |
| $T^{234}$ | H | H | $CF_3$ | $CF_3$ |
| $T^{235}$ | Cl | H | $OCF_2CF_2H$ | H |
| $T^{236}$ | H | $CF_3$ | H | Me |
| $T^{237}$ | H | Me | H | Me |
| $T^{238}$ | H | $CF_3$ | CN | Cl |

$T^k =$ 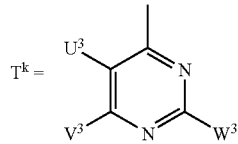

| $T^k$ | $U^3$ | $V^3$ | $W^3$ |
|---|---|---|---|
| $T^{300}$ | H | Me | Me |
| $T^{301}$ | H | Me | SMe |
| $T^{302}$ | H | Me | Cl |
| $T^{303}$ | Cl | Me | Cl |
| $T^{304}$ | H | Me | $CF_3$ |
| $T^{305}$ | Cl | Me | $CF_3$ |
| $T^{306}$ | Br | Me | $CF_3$ |
| $T^{307}$ | Br | Me | Cl |
| $T^{308}$ | F | Me | Cl |
| $T^{309}$ | F | Me | $CF_3$ |
| $T^{310}$ | H | Et | Me |
| $T^{311}$ | F | Et | Me |
| $T^{312}$ | Cl | Et | Me |
| $T^{313}$ | Cl | Et | H |
| $T^{314}$ | Cl | Et | $CF_3$ |
| $T^{315}$ | F | Et | $CF_3$ |
| $T^{316}$ | H | Et | $CF_3$ |
| $T^{317}$ | H | $CF_3$ | H |
| $T^{318}$ | F | $CF_3$ | H |
| $T^{319}$ | Cl | $CF_3$ | H |
| $T^{320}$ | Br | $CF_3$ | H |
| $T^{321}$ | H | $CF_3$ | Me |
| $T^{322}$ | F | $CF_3$ | Me |
| $T^{323}$ | Cl | $CF_3$ | Me |
| $T^{324}$ | Br | $CF_3$ | Me |
| $T^{325}$ | H | $CF_3$ | SMe |
| $T^{326}$ | F | $CF_3$ | SMe |
| $T^{327}$ | Cl | $CF_3$ | SMe |
| $T^{328}$ | Br | $CF_3$ | SMe |
| $T^{329}$ | H | $CF_3$ | Cl |
| $T^{330}$ | F | $CF_3$ | Cl |
| $T^{331}$ | Cl | $CF_3$ | Cl |
| $T^{332}$ | Br | $CF_3$ | Cl |
| $T^{333}$ | H | $CF_3$ | $CF_3$ |
| $T^{334}$ | F | $CF_3$ | $CF_3$ |
| $T^{335}$ | Cl | $CF_3$ | $CF_3$ |
| $T^{336}$ | Br | $CF_3$ | $CF_3$ |
| $T^{337}$ | H | $CF_3$ | $CF_3$ |
| $T^{338}$ | F | $CF_3$ | $CCl_3$ |

-continued

| | | | |
|---|---|---|---|
| T³³⁹ | Cl | CF₃ | CCl₃ |
| T³⁴⁰ | Br | CF₃ | CCl₃ |
| T³⁴¹ | H | Me | CCl₃ |
| T³⁴² | F | Me | CCl₃ |
| T³⁴³ | Cl | Me | CCl₃ |
| T³⁴⁴ | Br | Me | CCl₃ |
| T³⁴⁵ | Br | H | CCl₃ |
| T³⁴⁶ | Cl | H | CF₂CF₂CF₃ |
| T³⁴⁷ | CF₃ | H | CF₂CF₂CF₃ |
| T³⁴⁸ | COOEt | H | CF₃ |
| T³⁴⁹ | Me | Me | CF₃ |
| T³⁵⁰ | H | H | CF₃ |

T¹ = 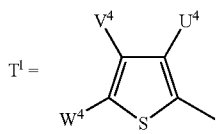

| T¹ | U⁴ | V⁴ | W⁴ |
|---|---|---|---|
| T⁴⁰⁰ | H | H | H |
| T⁴⁰¹ | Cl | H | H |
| T⁴⁰² | H | Cl | H |
| T⁴⁰³ | H | H | Cl |
| T⁴⁰⁴ | CF₃ | H | H |
| T⁴⁰⁵ | H | CF₃ | H |
| T⁴⁰⁶ | H | H | CF₃ |
| T⁴⁰⁷ | H | H | COMe |
| T⁴⁰⁸ | H | CF₃ | Cl |
| T⁴⁰⁹ | H | Cl | CF₃ |
| T⁴¹⁰ | H | Cl | Cl |
| T⁴¹¹ | H | NO₂ | Br |
| T⁴¹² | H | H | CHO |
| T⁴¹³ | H | H | 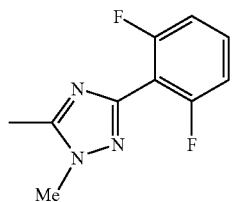 |
| T⁴¹⁴ | H | H | 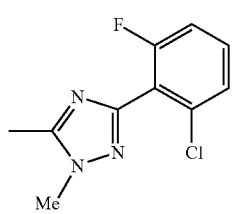 |
| T⁴¹⁵ | H | H | NO₂ |
| T⁴¹⁶ | H | Me | Br |
| T⁴¹⁷ | H | H | Br |
| T⁴¹⁸ | H | H | (3-CF₃)Ph |
| T⁴¹⁹ | H | H | (4-F)Ph |
| T⁴²⁰ | H | Me | (4-F)Ph |
| T⁴²¹ | H | Me | (4-Me)Ph |
| T⁴²² | H | Me | (4-Ph)Ph |
| T⁴²³ | H | Me | 3-thienyl |
| T⁴²⁴ | H | Me | (4-Cl)Ph |
| T⁴²⁵ | H | H | Ph |
| T⁴²⁶ | H | H | (4-Me)Ph |
| T⁴²⁷ | H | H | (4-CF₃)Ph |
| T⁴²⁸ | H | H | (2-Cl)Ph |
| T⁴²⁹ | H | H | (4-OCF₃)Ph |
| T⁴³⁰ | H | H | (4-Cl)Ph |
| T⁴³¹ | H | H | (3-Cl)Ph |
| T⁴³² | H | H | (3-Me)Ph |
| T⁴³³ | H | H | (3-CF₃, 5-CF₃)Ph |
| T⁴³⁴ | H | H | (2-Cl,4-Cl)Ph |
| T⁴³⁵ | H | H | (3-Cl,5-Cl)Ph |
| T⁴³⁶ | H | H | (2-Cl,4-Cl)Ph |

-continued
| | | | |
|---|---|---|---|
| T437 | H | H | —HC=NOCH2Ph |
| T438 | H | H | Me |
| T439 | H | H | —HC=NOCH2[(2-Cl, 4-Cl)Ph] |
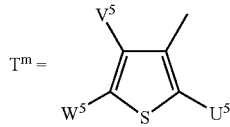
Tm =
| Tm | U5 | V5 | W5 |
|---|---|---|---|
| T450 | H | H | H |
| T451 | H | CF3 | H |
| T452 | H | H | CF3 |
| T453 | H | Cl | H |
| T454 | H | H | Cl |
| T455 | Cl | H | H |
T500
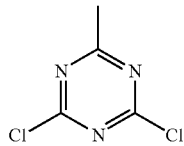
T501
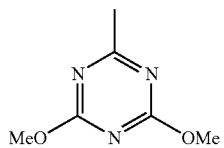
T502
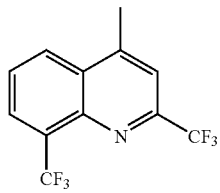
T503
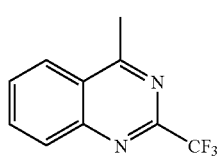
T504
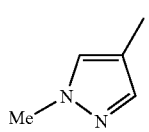
T505
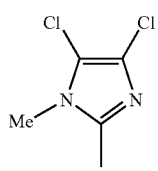
T506
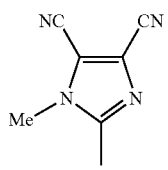

-continued
| | | |
|---|---|---|
| T507 | 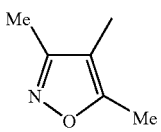 | |
| T508 | 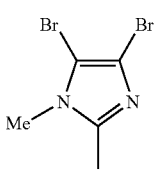 | |
| T509 | 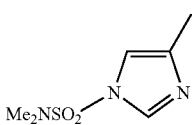 | |
| T510 | 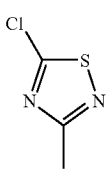 | |
| T511 | 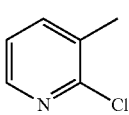 | |
| T512 | 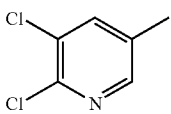 | |
| T513 | 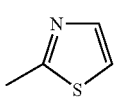 | |
| T514 | 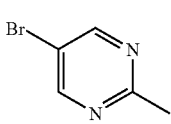 | |
| T515 | 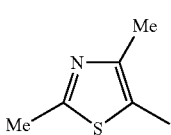 | |
| T516 | 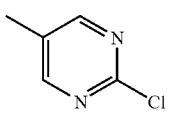 | |
| T517 | 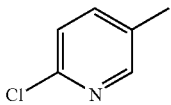 | |
| T518 | 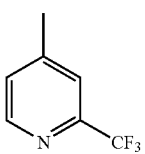 | |

-continued
T519 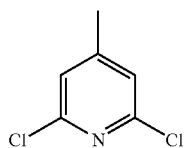
T520 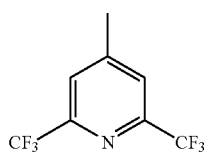
T521 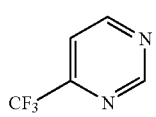
T522 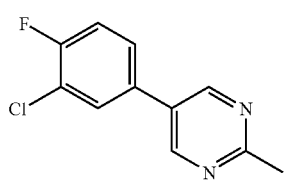
T523 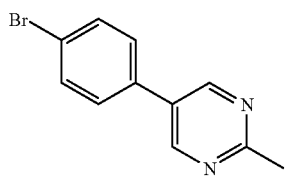
T524 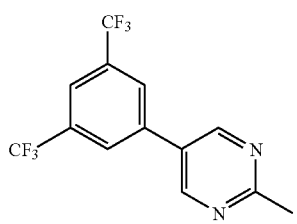
T525 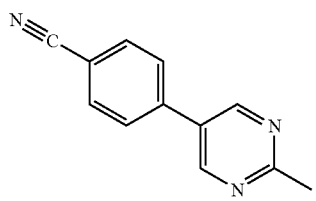
T526 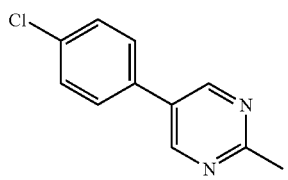

-continued

T⁵²⁷ 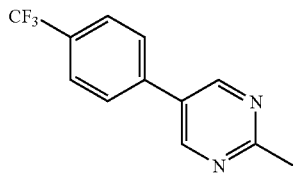

T⁵²⁸ 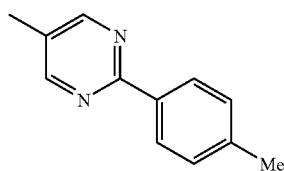

T⁵²⁹ 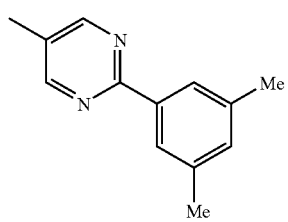

T⁵³⁰ 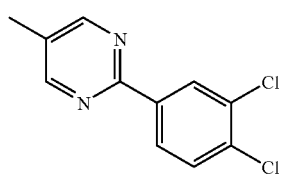

T⁵³¹ 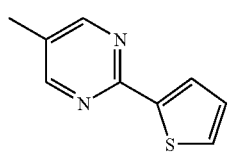

Me = methyl
Et = ethyl
Pr = n-propyl
Pr$^i$ = isopropyl
Bu = n-butyl
Bu$^t$ = tert-butyl
Ph = phenyl
b.p. = boiling point
m.p. = melting point

TABLE 1

$$R^1\!-\!\!\equiv\!\!-A-N\begin{smallmatrix}R^2\\R^3\end{smallmatrix}$$

| Comp. No. | R$^1$ | A | $-N\begin{smallmatrix}R^2\\R^3\end{smallmatrix}$ | Physico-chemical data |
|---|---|---|---|---|
| 8 | T$^{76}$ | CH$_2$ | L$^2$ | b.p. 92° C./0.1 mm Hg |
| 9 | T$^{78}$ | CH$_2$ | L$^2$ | b.p. 120–124° C./0.015 mm Hg |
| 10 | T$^{60}$ | CH$_2$ | L$^2$ | b.p. 155° C./0.03 mm Hg |
| 11 | T$^{26}$ | CH$_2$ | L$^{50}$ | b.p. 110° C./0.04 mm Hg |
| 12 | T$^{27}$ | CH$_2$ | L$^{50}$ | b.p. 98° C./0.05 mm Hg |
| 13 | T$^8$ | CH$_2$ | L$^{50}$ | m.p. 37–38° C. |
| 14 | T$^{49}$ | CH$_2$ | L$^{50}$ | b.p. 123–125° C./0.06 mm Hg |
| 15 | T$^{12}$ | CH$_2$ | L$^{50}$ | m.p. 67–68° C. |
| 16 | T$^{15}$ | CH$_2$ | L$^{50}$ | m.p. 79–79.5° C. |

TABLE 1-continued

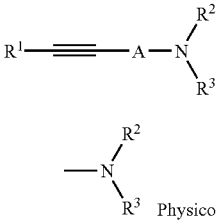

| Comp. No. | R¹ | A | NR²R³ | Physico-chemical data |
|---|---|---|---|---|
| 17 | $T^{82}$ | $CH_2$ | $L^{50}$ | m.p. 52–53° C. |
| 18 | $T^{49}$ | $CH_2$ | $L^{51}$ | b.p. 135° C./0.05 mm Hg |
| 19 | $T^{12}$ | $CH_2$ | $L^{51}$ | b.p. 142–144° C./0.2 mm Hg |
| 20 | $T^{77}$ | $CH_2$ | $L^{50}$ | b.p. 118° C./0.05 mm Hg |
| 21 | $T^{85}$ | $CH_2$ | $L^{50}$ | b.p. 145° C./0.1 mm Hg |
| 22 | $T^{63}$ | $CH_2$ | $L^{50}$ | m.p. 64–65° C. |
| 23 | $T^{61}$ | $CH_2$ | $L^{50}$ | m.p. 90–91° C. |
| 24 | $T^{32}$ | $CH_2$ | $L^{50}$ | b.p. 92–93° C./0.06 mm Hg |
| 25 | $T^{88}$ | $CH_2$ | $L^{50}$ | b.p. 106–108° C./0.015 mm Hg |
| 26 | $T^{31}$ | $CH_2$ | $L^{50}$ | b.p. 87–89° C./0.04 mm Hg |
| 27 | $T^{76}$ | $CH_2$ | $L^{50}$ | b.p. 121° C./0.05 mm Hg |
| 28 | $T^{23}$ | $CH_2$ | $L^{50}$ | b.p. 91–93° C./0.03 mm Hg |
| 29 | $T^{33}$ | $CH_2$ | $L^{50}$ | b.p. 96–98° C./0.02 mm Hg |
| 30 | $T^{44}$ | $CH_2$ | $L^{50}$ | b.p. 97–98° C./0.01 mm Hg |
| 31 | $T^{39}$ | $CH_2$ | $L^{37}$ | b.p. 90–96° C./0.1 mm Hg |
| 32 | $T^{39}$ | $CH_2$ | $L^{51}$ | pale yellow oil |
| 33 | $T^{39}$ | $CH_2$ | $L^{52}$ | b.p. 88–90° C./1.0 mm Hg |
| 34 | $T^{39}$ | $CH_2$ | $L^{53}$ | b.p. 110–115° C./0.07 mm Hg |
| 35 | $T^{1}$ | $CH_2$ | $L^{52}$ | b.p. 98–99° C./0.085 mm Hg |
| 36 | $T^{311}$ | $CH_2$ | $L^{50}$ | $^1$H-NMR (CDCl$_3$): δ = 0.95 (d, 3H), 1.31 (t, 3H), 2.62 (s, 3H), 3.61 (s, 2H) |
| 37 | $T^{313}$ | $CH_2$ | $L^{50}$ | $^1$H-NMR (CDCl$_3$): δ = 0.95 (d, 3H), 1.30 (t, 3H), 2.95 (q, 2H), 3.68 (s, 2H) 8.92 (s, 1H) |
| 38 | $T^{310}$ | $CH_2$ | $L^{50}$ | $^1$H-NMR (CDCl$_3$): δ = 0.95 (d, 3H), 1.30 (t, 3H) 2.70 (s, 3H), 2.75 (q, 2H), 3.56 (s, 2H), 7.06 (s, 1H) |
| 39 | $T^{39}$ | $CH_2$ | $L^{14}$ | $^1$H-NMR (CDCl$_3$): δ = 1.17 (d, 3H), 3.57 (d, 1H) 3.85 (d, 1H), 7.77 (s, 1H) 7.83 (s, 2H) |
| 40 | $T^{39}$ | $CH_2$ | $L^{3}$ | $^1$H-NMR (CDCl$_3$): δ = 1.58–1.80 (m, 8H), 2.78 (m, 4H), 3.61 (s, 2H), 7.77 (s, 1H), 7.83 (s, 2H) |
| 41 | $T^{39}$ | $CH_2$ | $L^{18}$ | $^1$H-NMR (CDCl$_3$): δ = 2.24 (m, 2H), 2.76 (t, 2H), 3.18 (m, 2H), 3.62 (S, 2H), 5.75 (m, 2H) |
| 42 | $T^{39}$ | $CH_2$ | $L^{6}$ | $^1$H-NMR (CDCl$_3$): δ = 3.56 (d, 1H), 3.91 (d, 1H) |
| 43 | $T^{39}$ | $CH_2$ | $L^{22}$ | $^1$H-NMR (CDCl$_3$): δ = 1.00 (d, 6H), 1.30 (t, 2H) 1.98 (m, 2H), 2.22 (m, 2H) 2.58 (m, 2H), 3.50 (s, 2H) |
| 44 | $T^{39}$ | $CH_2$ | $L^{23}$ | $^1$H-NMR (CDCl$_3$): δ = 0.90 (d, 6H), 1.75 (m, 6H), 2.88 (m, 2H), 3.55 (s, 2H) |
| 45 | $T^{39}$ | $CH_2$ | $L^{24}$ | $^1$H-NMR (CDCl$_3$): δ = 0.90 (t, 3H), 3.52 (s, 2H) |
| 46 | $T^{39}$ | $CH_2$ | $L^{30}$ | $^1$H-NMR (CDCl$_3$): δ = 1.28 (t, 3H), 3.56 (s, 2H), 4.17 (q, 2H) |
| 47 | $T^{39}$ | $CH_2$ | $L^{31}$ | $^1$H-NMR (CDCl$_3$): δ = 1.43 (s, 9H), 2.58 (t, 4H), 3.50 (t, 4H), 3.58 (s, 2H) |
| 48 | $T^{39}$ | $CH_2$ | $L^{36}$ | $^1$H-NMR (CDCl$_3$): δ = 1.82 (t, 4H), 2.73 (t, 4H), 3.57 (s, 2H), 3.98 (s, 4H) |
| 49 | $T^{39}$ | $CH_2$ | $L^{44}$ | $^1$H-NMR (CDCl$_3$): δ = 0.95 (t, 3H), 3.56 (d, 1H), 3.87(d, 1H) |
| 50 | $T^{39}$ | $CH_2$ | $L^{47}$ | $^1$H-NMR (CDCl$_3$): δ = 2.96 (m, 4H), 3.77 (s, 2H), |

TABLE 1-continued $$R^1-\equiv-A-N{\overset{R^2}{\underset{R^3}{}}}$$

| Comp. No. | $R^1$ | A | $-N{\overset{R^2}{\underset{R^3}{}}}$ | Physico-chemical data |
|---|---|---|---|---|
| 51 | $T^{39}$ | $CH_2$ | $L^{17}$ | 3.83 (s, 2H), 7.0–7.2 (m, 4H) $^1$H-NMR (CDCl$_3$): δ = 2.45 (s, 3H), 3.59 (s, 2H) |
| 52 | $T^{33}$ | $CH_2$ | $L^{17}$ | $^1$H-NMR (CDCl$_3$): δ = 2.36 (s, 3H), 3.57 (s, 2H), 7.55 (m, 4H) |
| 53 | $T^{44}$ | $CH_2$ | $L^{17}$ | $^1$H-NMR (CDCl$_3$): δ = 2.33 (s, 3H), 3.60 (s, 2H) |
| 54 | $T^{33}$ | $CH_2$ | $L^{12}$ | $^1$H-NMR (CDCl$_3$): δ = 2.62 (t, 4H), 3.55 (s, 2H), 3.78 (t, 4H) |
| 55 | $T^{44}$ | $CH_2$ | $L^{12}$ | $^1$H-NMR (CDCl$_3$): δ = 2.68 (t, 4H), 3.60 (s, 2H), 3.78 (t, 4H), 7.5 (m, 2H), 7.76 (d, 1H) |
| 56 | $T^{200}$ | $CH_2$ | $L^{12}$ | $^1$H-NMR (CDCl$_3$): δ = 2.70 (t, 4H), 3.65 (s, 2H), 3.78 (t, 4H), 7.97 (d, 1H), 8.72 (d, 1H) |
| 57 | $T^{200}$ | $CH_2$ | $L^{50}$ | $^1$H-NMR (CDCl$_3$): δ = 0.96 (d, 3H), 1.20–1.43 (m, 3H), 1.7 (m, 2H), 2.39 (m, 2H), 2.95 (m, 2H), 3.65 (s, 2H), 7.97 (d, 1H), 8.71 (d, 1H) |
| 58 | $T^{218}$ | $CH_2$ | $L^{50}$ | $^1$H-NMR (CDCl$_3$): δ = 0.96 (d, 3H), 3.58 (s, 2H), 7.52 (d, 1H), 7.86 (dd, 1H), 8.81 (d, 1H) |
| 59 | $T^{214}$ | $CH_2$ | $L^{50}$ | $^1$H-NMR (CDCl$_3$): δ = 0.94 (d, 3H), 3.55 (s, 2H), 7.30 (d, 1H), 7.78 (dd, 1H), 8.61 (d, 1H) |
| 60 | $T^{233}$ | $CH_2$ | $L^{50}$ | $^1$H-NMR (CDCl$_3$): δ = 0.96 (d, 3H), 3.58 (s, 2H), 7.78 (d, 1H), 7.80 (d, 1H) |
| 61 | $T^{39}$ | $CH_2$ | $L^{33}$ | $^1$H-NMR (CDCl$_3$): δ = 0.95 (s, 3H), 1.06 (s, 3H), 1.24 (s, 3H), 3.57 (d, 1H), 3.65 (d, 1H) |
| 62 | $T^{200}$ | $CH_2$ | $L^{17}$ | $^1$H-NMR (CDCl$_3$): δ = 2.48 (s, 3H), 3.68 (s, 2H), 7.96 (d, 1H), 8.72 (d, 1H) |
| 63 | $T^{39}$ | $CH_2$ | $L^{34}$ | $^1$H-NMR (CDCl$_3$): δ = 1.6–2.1 (m, 8H), 2.75 (m, 3H), 2.97 (m, 2H), 3.46 (s, 2H) |
| 64 | $T^{44}$ | $CH_2$ | $L^{34}$ | $^1$H-NMR (CDCl$_3$): δ = 2.4 (m, 2H), 2.60 (m, 4H), 2.95 (m, 2H), 3.60 (s, 2H), 7.45 (dd, 1H), 7.51 (d, 1H), 7.73 (d, 1H) |
| 65 | $T^{33}$ | $CH_2$ | $L^{43}$ | $^1$H-NMR (CDCl$_3$): δ = 2.57 (d, 2H), 3.48 (s, 2H), 7.13 (m, 3H), 7.27 (m, 2H), 7.54 (m, 4H) |
| 66 | $T^{44}$ | $CH_2$ | $L^{43}$ | $^1$H-NMR (CDCl$_3$): δ = 2.57 (d, 2H), 3.58 (s, 2H), 7.13 (m, 3H), 7.27 (m, 2H), 7.48 (m, 2H), 7.70 (d, 1H) |
| 67 | $T^{39}$ | $CH_2$ | $L^{43}$ | $^1$H-NMR (CDCl$_3$): δ = 2.58 (d, 2H), 3.50 (s, 2H), 7.13 (m, 3H), 7.27 (m, 2H), 7.78 (s, 1H), 7.82 (s, 2H) |
| 68 | $T^{33}$ | $CH_2$ | $L^{34}$ | $^1$H-NMR (CDCl$_3$): δ = 1.82 (m, 4H), 2.32 (m, 2H), 2.62 (m, 4H), 2.97 (m, 2H), 3.53 (s, 2H), 7.55 (m, 4H) |
| 69 | $T^1$ | $CH_2$ | $L^{14}$ | |

TABLE 1-continued

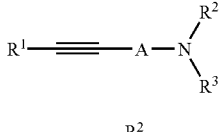

| Comp. No. | R¹ | A | NR²R³ | Physico-chemical data |
|---|---|---|---|---|
| 70 | $T^{46}$ | $CH_2$ | $L^{50}$ | $^1$H-NMR (CDCl$_3$): δ = 0.97 (d, 3H), 1.36 (m, 3H), 2.21 (m, 2H), 2.94 (m, 2H), 3.52 (s, 2H), 7.20 (dd, 1H), 7.57 (d, 1H), 7.60 (d, 1H) |
| 71 | $T^{400}$ | $CH_2$ | $L^{50}$ | $^1$H-NMR (CDCl$_3$): δ = 0.97 (d, 3H), 3.50 (s, 2H), 6.97 (dd, 1H), 7.18 (dd, 1H), 7.22 (dd, 1H) |
| 72 | $T^{450}$ | $CH_2$ | $L^{50}$ | $^1$H-NMR (CDCl$_3$): δ = 0.97 (d, 3H), 3.47 (s, 2H), 7.10 (d, 1H), 7.24 (dd, 1H), 7.40 (d, 1H) |
| 73 | $T^{39}$ | $CH(CH_3)$ | $L^{50}$ | |
| 74 | $T^{39}$ | $C(CH_3)_2$ | $L^{50}$ | |
| 75 | $T^{39}$ | CO | $L^{50}$ | |
| 76 | $T^{39}$ | $CF_2$ | $L^{50}$ | |
| 77 | $T^{39}$ | $CH(CH_2Ph)$ | $L^{50}$ | b.p. 140° C./0.01 mm Hg |
| 78 | $T^{46}$ | $CH(CH_3)$ | $L^{50}$ | |
| 79 | $T^{46}$ | $C(CH_3)_2$ | $L^{50}$ | |
| 80 | $T^{46}$ | CO | $L^{50}$ | |
| 81 | $T^{46}$ | $CF_2$ | $L^{50}$ | |
| 82 | $T^{46}$ | $CH(CH_2Ph)$ | $L^{50}$ | |
| 83 | $T^1$ | $CH_2$ | $L^{45}$ | |
| 84 | $T^1$ | $CH_2$ | $L^{19}$ | oil |
| 85 | $T^{39}$ | $CH_2$ | $L^{45}$ | |
| 86 | $T^{39}$ | $CH_2$ | $L^{19}$ | |
| 87 | $T^1$ | $CH_2$ | $L^{12}$ | |
| 88 | $T^{39}$ | $CH_2$ | $L^{14}$ | |
| 89 | $T^{21}$ | $CH_2$ | $L^{50}$ | b.p. 95° C./0.02 mm Hg |
| 90 | $T^{62}$ | $CH_2$ | $L^{50}$ | b.p. 144° C./0.03 mm Hg |
| 91 | $T^4$ | $CH_2$ | $L^{50}$ | m.p. 48–49° C. |
| 92 | $T^{103}$ | $CH_2$ | $L^{50}$ | m.p. 89.5–90° C. |
| 93 | $T^{86}$ | $CH_2$ | $L^{50}$ | b.p. 122–124° C./0.01 mm Hg |
| 94 | $T^3$ | $CH_2$ | $L^{50}$ | b.p. 110–114° C./0.015 mm Hg |
| 95 | $T^{104}$ | $CH_2$ | $L^{50}$ | b.p. 113° C./0.04 mm Hg |
| 96 | $T^{105}$ | $CH_2$ | $L^{50}$ | b.p. 108° C./0.03 mm Hg |
| 97 | $T^{52}$ | $CH_2$ | $L^{50}$ | b.p. 119–120° C./0.005 mm Hg |
| 98 | $T^{89}$ | $CH_2$ | $L^{50}$ | b.p. 144–146° C./0.015 mm Hg |
| 99 | $T^{106}$ | $CH_2$ | $L^{50}$ | b.p. 124° C./0.8 mm Hg |
| 100 | $T^{56}$ | $CH_2$ | $L^{50}$ | b.p. 126–128° C./0.05 mm Hg |
| 101 | $T^{107}$ | $CH_2$ | $L^{50}$ | b.p. 127° C./0.002 mm Hg |
| 102 | $T^{108}$ | $CH_2$ | $L^{50}$ | b.p. 110–112° C./0.05 mm Hg |
| 103 | $T^{53}$ | $CH_2$ | $L^{50}$ | b.p. 123–126° C./0.01 mm Hg |
| 104 | $T^{111}$ | $CH_2$ | $L^{50}$ | b.p. 135° C./0.05 mm Hg |
| 105 | $T^{112}$ | $CH_2$ | $L^{50}$ | b.p. 125° C./0.06 mm Hg |
| 106 | $T^5$ | $CH_2$ | $L^{50}$ | b.p. 140–142° C./0.05 mm Hg |
| 107 | $T^7$ | $CH_2$ | $L^{50}$ | b.p. 125° C./0.005 mm Hg |
| 108 | $T^{116}$ | $CH_2$ | $L^{50}$ | m.p. 36–37° C. |
| 109 | $T^{117}$ | $CH_2$ | $L^{50}$ | m.p. 57–58° C. |
| 110 | $T^{118}$ | $CH_2$ | $L^{50}$ | b.p. 119° C./0.005 mm Hg |
| 111 | $T^{39}$ | $CH_2$ | $L^{22}$ | b.p. 97–101° C./0.2 mm Hg |
| 112 | $T^{39}$ | $CH_2$ | $L^{90}$ | b.p. 120–125° C./0.07 mm Hg |
| 113 | $T^{39}$ | $CH_2$ | $L^{24}$ | b.p. 130° C./0.35 mm Hg |
| 114 | $T^{87}$ | $CH_2$ | $L^{50}$ | b.p. 126–129° C./0.11 mm Hg |
| 115 | $T^{119}$ | $CH_2$ | $L^{50}$ | m.p. 66–68° C. |
| 116 | $T^{120}$ | $CH_2$ | $L^{50}$ | b.p. 138–143° C./0.05 mm Hg |
| 117 | $T^{79}$ | $CH_2$ | $L^{50}$ | m.p. 62–63° C. |
| 118 | $T^{39}$ | $CH_2$ | $L^{76}$ | |
| 119 | $T^{94}$ | $CH_2$ | $L^{50}$ | m.p. 47–48° C. |
| 120 | $T^{78}$ | $CH_2$ | $L^{50}$ | b.p. 130° C./0.03 mm Hg |
| 121 | $T^{26}$ | $CH_2$ | $L^{50}$ | b.p. 110° C./0.04 mm Hg |
| 122 | $T^{25}$ | $CH_2$ | $L^{50}$ | b.p. 95° C./0.03 mm Hg |
| 123 | $T^{123}$ | $CH_2$ | $L^{50}$ | |
| 124 | $T^{59}$ | $CH_2$ | $L^{50}$ | |
| 125 | $T^{39}$ | $CH_2$ | $L^{28}$ | m.p. 47–48° C. |
| 126 | $T^{124}$ | $CH_2$ | $L^{50}$ | b.p. 118° C./0.05 mm Hg |

TABLE 1-continued $$R^1 — \equiv — A — N{\overset{R^2}{\underset{R^3}{}}}$$

$$—N{\overset{R^2}{\underset{R^3}{}}}$$

| Comp. No. | R¹ | A | —N(R²)(R³) | Physico-chemical data |
|---|---|---|---|---|
| 127 | T¹²⁶ | CH₂ | L⁵⁰ | b.p. 131° C./0.1 mm Hg |
| 128 | T³⁹ | CH₂ | L⁷⁸ | m.p. 86–87° C. |
| 129 | T³⁹ | CH₂ | L⁶⁴ | mp. 70–72° C. |
| 130 | T¹²⁸ | CH₂ | L⁵⁰ | b.p. 162° C./0.25 mm Hg |
| 131 | T¹²⁹ | CH₂ | L⁵⁰ | m.p. 58–59° C. |
| 132 | T³⁹ | CH₂ | L⁸⁰ | m.p. 45° C. |
| 133 | T¹³⁰ | CH₂ | L⁵⁰ | b.p. 132–134° C./0.2 mm Hg |
| 134 | T¹ | CH(Prⁱ) | L² | b.p. 130–130° C./0.2 mm Hg |
| 135 | T¹⁴¹ | CH₂ | L⁵⁰ | b.p. 126–132° C./0.1 mm Hg |
| 136 | T¹³¹ | CH₂ | L⁵⁰ | b.p. 112–116° C./0.1 mm Hg |
| 137 | T¹³² | CH₂ | L⁵⁰ | b.p. 105–110° C./0.1 mm Hg |
| 138 | T¹ | CH(Prⁱ) | L⁵⁰ | b.p. 156–158° C./1.75 mm Hg |
| 139 | T³⁹ | CH₂ | L⁸⁶ | wax |
| 140 | T¹ | CO | L⁵⁰ | m.p. 56–57° C. |
| 141 | T¹³⁴ | CH₂ | L⁵⁰ | b.p. 160° C./0.2 mm Hg |
| 142 | T⁶⁴ | CH₂ | L⁵⁰ | m.p. 58–59° C. |
| 143 | T¹³⁵ | CH₂ | L⁵⁰ | b.p. 145° C./0.1 mm Hg |
| 144 | T¹³³ | CH₂ | L⁵¹ |  |
| 145 | T¹³⁶ | CH₂ | L⁵⁰ | m.p. 46–47° C. |
| 146 | T¹³⁷ | CH₂ | L⁵⁰ |  |
| 147 | T³⁹ | CO | L⁵⁰ | m.p. 110–111° C. |
| 148 | T¹³⁸ | CH₂ | L⁵⁰ | m.p. 63–64° C. |
| 149 | T³⁹ | CH₂ | L⁷⁹ | b.p. 185–187° C./0.7 mm Hg |
| 150 | T¹⁴⁰ | CH₂ | L⁵⁰ | m.p. 50–51° C. |
| 151 | T⁶ | CH₂ | L⁶³ | oil |
| 152 | T³⁹ | CH₂ | L⁵⁰ | b.p. 92–95°C./0.04 mm Hg; m.p. 22° C. |
| 153 | T⁴⁴ | CH₂ | L³³ | ¹H-NMR (CDCl₃): δ = 0.92 (s, 3H), 1.06 (s, 3H), 1.23 (s, 3H), 3.60 (d, 1H), 3.75 (d, 1H), 7.70 (d, 1H) |
| 154 | T³³ | CH₂ | L³³ | ¹H-NMR (CDCl₃): δ = 0.86 (s, 3H), 1.06 (s, 3H), 1.25 (s, 3H), 3.53 (d, 1H), 3.65 (d, 1H), 7.50 (d, 2H), 7.58 (d, 2H) |
| 155 | T⁵¹¹ | CH₂ | L⁵⁰ | ¹H-NMR (CDCl₃): δ = 0.96 (d, 3H), 3.58 (s, 2H), 7.18 (dd, 1H), 7.68 (dd, 1H), 8.32 (dd,1H) |
| 156 | T⁵¹² | CH₂ | L⁵⁰ | ¹H-NMR (CDCl₃): δ = 0.95 (d, 3H), 3.48 (s, 2H), 7.78 (d, 1H), 8.36 (d, 1H) |
| 157 | T⁵⁰² | CH₂ | L⁵⁰ | ¹H-NMR (CDCl₃): δ = 0.97 (d, 3H), 3.70 (s, 2H), 7.75 (t, 1H), 7.83 (s, 1H), 8.19 (d, 1H), 8.55 (d, 1H) |
| 158 | T²¹⁹ | CH₂ | L⁵⁰ | m.p. 75–77° C. |
| 159 | T³²⁵ | CH₂ | L²² | ¹H-NMR (CDCl₃): δ = 0.98 (d, 6H), 1.30 (t, 3H), 3.56 (d, 2H), 7.25 (s, 1H) |
| 160 | T³²⁵ | CH₂ | L⁵⁰ | ¹H-NMR (CDCl₃): δ = 0.97 (d, 3H), 2.60 (s, 3H), 3.57 (s, 2H), 7.27 (s, 1 H) |
| 161 | 1321 | CH₂ | L⁵⁰ | ¹H-NMR (CDCl₃): δ = 0.97 (d, 3H), 2.80 (s, 3H), 3.59 (s, 2H), 7.49 (s, 1H) |
| 162 | T²³³ | CH₂ | L²² | ¹H-NMR (CDCl₃): δ = 0.98 (d, 6H), 1.30 (t, 3H), 3.55 (s, 2H), 7.77 (s, 1H), 7.79 (s, 1H) |
| 163 | T²³³ | CH₂ | L²³ | ¹H-NMR (CDCl₃): δ = 0.90 (d, 6H), 1.65–1.85 (m, 6H), 3.58 (s, 2H), 7.76 (s, 1H), 7.80 (s, 1H) |
| 164 | T³²⁵ | CH₂ | L³ | ¹H-NMR (CDCl₃): δ = 1.55–1.80 (m, 8H), 2.60 (s, 3H), 3.67 (s, 2H), 7.25 (s, 1H) |

TABLE 1-continued $$R^1-\!\!\!\equiv\!\!\!-A-N\genfrac{}{}{0pt}{}{R^2}{R^3}$$

$$-N\genfrac{}{}{0pt}{}{R^2}{R^3}$$

| Comp. No. | R¹ | A | | Physico-chemical data |
|---|---|---|---|---|
| 165 | T²³¹ | CH₂ | L⁵⁰ | ¹H-NMR (CDCl₃): δ = 0.95 (d, 3H), 3.65 (s, 2H), 7.70 (d, 1H), 8.16 (d, 1H) |
| 166 | T³²⁵ | CH₂ | L²³ | ¹H-NMR (CDCl₃): δ = 0.90 (d, 6H), 2.60 (t, 3H), 3.59 (s, 2H), 7.29 (s, 1H) |
| 167 | T³⁵⁰ | CH₂ | L⁵⁰ | oil |
| 168 | T⁵²¹ | CH₂ | L⁵⁰ | oil |
| 169 | T³⁹ | CH₂ | L⁶⁹ | oil |
| 170 | T²³³ | CH₂ | L⁶⁹ | oil |
| 171 | T¹⁴² | CH₂ | L⁵⁰ | oil |
| 172 | T¹⁴³ | CH₂ | L⁵⁰ | oil |
| 173 | T¹⁴⁴ | CH₂ | L⁵⁰ | oil |
| 174 | T¹⁴⁵ | CH₂ | L⁵⁰ | oil |
| 175 | T¹⁴⁶ | CH₂ | L⁵⁰ | oil |
| 176 | T¹⁴⁸ | CH₂ | L⁵⁰ | oil |
| 177 | T¹⁴⁹ | CH₂ | L⁵⁰ | oil |
| 178 | T¹⁵⁰ | CH₂ | L⁵⁰ | oil |
| 179 | T¹⁵¹ | CH₂ | L⁵⁰ | oil |
| 180 | T¹⁵² | CH₂ | L⁵⁰ | oil |
| 181 | T¹⁴⁷ | CH₂ | L⁵⁰ | oil |
| 182 | T¹⁵³ | CH₂ | L⁵⁰ | oil |
| 183 | T¹⁵⁴ | CH₂ | L⁵⁰ | oil |
| 184 | T¹⁵⁵ | CH₂ | L⁵⁰ | oil |
| 185 | T¹⁵⁶ | CH₂ | L⁵⁰ | oil |
| 186 | T¹⁵⁷ | CH₂ | L⁵⁰ | oil |
| 187 | T¹⁵⁸ | CH₂ | L⁵⁰ | oil |
| 188 | T¹⁵⁹ | CH₂ | L⁵⁰ | oil |
| 189 | T¹⁶⁰ | CH₂ | L⁵⁰ | oil |
| 190 | T¹⁶¹ | CH₂ | L⁵⁰ | oil |
| 191 | T¹⁶² | CH₂ | L⁵⁰ | oil |
| 192 | T¹⁶³ | CH₂ | L⁵⁰ | oil |
| 193 | T¹⁶⁴ | CH₂ | L⁵⁰ | oil |
| 194 | T¹⁶⁵ | CH₂ | L⁵⁰ | oil |
| 195 | T¹⁶⁶ | CH₂ | L⁵⁰ | oil |
| 196 | T¹⁶⁷ | CH₂ | L⁵⁰ | oil |
| 197 | T²³⁶ | CH₂ | L⁵⁰ | ¹H-NMR(CDCl₃) δ = 0.97 (d, 3H), 2.62 (s, 3H), 3.55 (s, 2H), 7.29 (s, 1H), 7.45 (s, 1H). |
| 198 | T²³³ | CH₂ | L⁷² | oil |
| 199 | T³⁹ | CH₂ | L⁷² | oil |
| 200 | T³²⁹ | CH₂ | L⁵⁰ | oil |
| 201 | T²³⁷ | CH₂ | L⁵⁰ | oil |
| 202 | T²³⁸ | CH₂ | L⁵⁰ | oil |
| 203 | T²¹⁷ | CH₂ | L⁵⁰ | oil |
| 204 | T²³³ | CH₂ | L⁹¹ | ¹H-NMR(CDCl₃): δ = 3.62 (d, 2H), 7.80 (s, 2H). |
| 205 | T³⁹ | CH₂ | L⁹¹ | oil |
| 206 | T⁵¹³ | CH₂ | L⁵⁰ | oil |
| 207 | T¹⁶⁸ | CH₂ | L⁵⁰ | oil |
| 208 | T⁴¹⁵ | CH₂ | L⁵⁰ | m.p. 54° C. |
| 209 | T¹⁶⁹ | CH₂ | L⁵⁰ | oil |
| 210 | T⁵¹⁴ | CH₂ | L⁵⁰ | oil |
| 211 | T⁵¹⁵ | CH₂ | L⁵⁰ | oil |
| 212 | T⁵¹⁶ | CH₂ | L⁵⁰ | m.p. 77–78° C. |
| 213 | T⁴¹⁶ | CH₂ | L⁵⁰ | m.p. 96–97° C. |
| 214 | T⁴⁰⁷ | CH₂ | L⁵⁰ | m.p. 73–74° C. |
| 215 | T⁴¹⁷ | CH₂ | L⁵⁰ | oil |
| 216 | T⁴⁰³ | CH₂ | L⁵⁰ | oil |
| 217 | T¹⁷⁰ | CH₂ | L⁵⁰ | oil |
| 218 | T¹⁷¹ | CH₂ | L⁵⁰ | oil |
| 219 | T¹⁷² | CH₂ | L⁵⁰ | oil |
| 220 | T¹⁷³ | CH₂ | L⁵⁰ | oil |
| 221 | T¹⁷⁴ | CH₂ | L⁵⁰ | oil |
| 222 | T¹⁷⁵ | CH₂ | L⁵⁰ | oil |
| 223 | T¹⁷⁶ | CH₂ | L⁵⁰ | oil |
| 224 | T¹⁷⁷ | CH₂ | L⁵⁰ | oil |

TABLE 1-continued

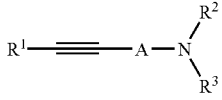

| Comp. No. | R$^1$ | A | —N(R$^2$)(R$^3$) | Physico-chemical data |
|---|---|---|---|---|
| 225 | T$^{178}$ | CH$_2$ | L$^{50}$ | oil |
| 226 | T$^{179}$ | CH$_2$ | L$^{50}$ | oil |
| 227 | T$^{180}$ | CH$_2$ | L$^{50}$ | oil |
| 228 | T$^{181}$ | CH$_2$ | L$^{50}$ | oil |
| 229 | T$^{418}$ | CH$_2$ | L$^{50}$ | oil |
| 230 | T$^{419}$ | CH$_2$ | L$^{50}$ | oil |
| 231 | T$^{189}$ | CH$_2$ | L$^{50}$ | oil |
| 232 | T$^{420}$ | CH$_2$ | L$^{50}$ | oil |
| 233 | T$^{517}$ | CH$_2$ | L$^{50}$ | oil |
| 234 | T$^{203}$ | CH$_2$ | L$^{50}$ | $^1$H-NMR(CDCl$_3$): δ 0.96 (d, 3H), 3.56 (s, 2H), 7.45 (s, 1H), 7.55 (s, 1H). |
| 235 | T$^{518}$ | CH$_2$ | L$^{50}$ | oil |
| 236 | T$^{421}$ | CH$_2$ | L$^{50}$ | oil |
| 237 | T$^{422}$ | CH$_2$ | L$^{50}$ | oil |
| 238 | T$^{423}$ | CH$_2$ | L$^{50}$ | oil |
| 239 | T$^{424}$ | CH$_2$ | L$^{50}$ | oil |
| 240 | T$^{425}$ | CH$_2$ | L$^{50}$ | oil |
| 241 | T$^{426}$ | CH$_2$ | L$^{50}$ | oil |
| 242 | T$^{427}$ | CH$_2$ | L$^{50}$ | oil |
| 243 | T$^{428}$ | CH$_2$ | L$^{50}$ | oil |
| 244 | T$^{429}$ | CH$_2$ | L$^{50}$ | oil |
| 245 | T$^{430}$ | CH$_2$ | L$^{50}$ | oil |
| 246 | T$^{432}$ | CH$_2$ | L$^{50}$ | oil |
| 247 | T$^{431}$ | CH$_2$ | L$^{50}$ | oil |
| 248 | T$^{190}$ | CH$_2$ | L$^{50}$ | oil |
| 249 | T$^{191}$ | CH$_2$ | L$^{50}$ | oil |
| 250 | T$^{192}$ | CH$_2$ | L$^{50}$ | oil |
| 251 | T$^{193}$ | CH$_2$ | L$^{50}$ | oil |
| 252 | T$^{195}$ | CH$_2$ | L$^{50}$ | oil |
| 253 | T$^{194}$ | CH$_2$ | L$^{50}$ | oil |
| 254 | T$^{182}$ | CH$_2$ | L$^{50}$ | oil |
| 255 | T$^{196}$ | CH$_2$ | L$^{50}$ | oil |
| 256 | T$^{197}$ | CH$_2$ | L$^{50}$ | oil |
| 257 | T$^{198}$ | CH$_2$ | L$^{50}$ | oil |
| 258 | T$^{199}$ | CH$_2$ | L$^{50}$ | oil |
| 259 | T$^{600}$ | CH$_2$ | L$^{50}$ | oil |
| 260 | T$^{601}$ | CH$_2$ | L$^{50}$ | oil |
| 261 | T$^{602}$ | CH$_2$ | L$^{50}$ | oil |
| 262 | T$^{603}$ | CH$_2$ | L$^{50}$ | oil |
| 263 | T$^{604}$ | CH$_2$ | L$^{50}$ | oil |
| 264 | T$^{183}$ | CH$_2$ | L$^{50}$ | oil |
| 265 | T$^{605}$ | CH$_2$ | L$^{50}$ | oil |
| 266 | T$^{606}$ | CH$_2$ | L$^{50}$ | oil |
| 267 | T$^{39}$ | CH$_2$ | L$^{53}$ | oil |
| 268 | T$^{607}$ | CH$_2$ | L$^{50}$ | oil |
| 269 | T$^{608}$ | CH$_2$ | L$^{50}$ | oil |
| 270 | T$^{609}$ | CH$_2$ | L$^{50}$ | oil |
| 271 | T$^{433}$ | CH$_2$ | L$^{50}$ | oil |
| 272 | T$^{424}$ | CH$_2$ | L$^{50}$ | oil |
| 273 | T$^{435}$ | CH$_2$ | L$^{50}$ | oil |
| 274 | T$^{436}$ | CH$_2$ | L$^{50}$ | oil |
| 275 | T$^{522}$ | CH$_2$ | L$^{50}$ | m.p. 132° C. |
| 276 | T$^{523}$ | CH$_2$ | L$^{50}$ | m.p. 141° C. |
| 277 | T$^{524}$ | CH$_2$ | L$^{50}$ | m.p. 146° C. |
| 278 | T$^{525}$ | CH$_2$ | L$^{50}$ | m.p. 169° C. |
| 279 | T$^{526}$ | CH$_2$ | L$^{50}$ | m.p. 143° C. |
| 280 | T$^{527}$ | CH$_2$ | L$^{50}$ | m.p. 149° C. |
| 281 | T$^{39}$ | CH$_2$ | L$^{93}$ | oil |
| 282 | T$^{233}$ | CH$_2$ | L$^{93}$ | oil |
| 283 | T$^{185}$ | CH$_2$ | L$^{50}$ | oil |
| 284 | T$^{186}$ | CH$_2$ | L$^{50}$ | oil |
| 285 | T$^{187}$ | CH$_2$ | L$^{50}$ | oil |
| 286 | T$^{188}$ | CH$_2$ | L$^{50}$ | oil |
| 287 | T$^{39}$ | CH$_2$ | L$^{92}$ | oil |
| 288 | T$^{233}$ | CH$_2$ | L$^{92}$ | oil |
| 289 | T$^{69}$ | CH$_2$ | L$^{50}$ | m.p. 61° C. |

TABLE 1-continued

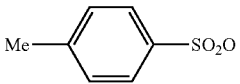

| Comp. No. | R¹ | A | —N(R²)(R³) | Physico-chemical data |
|---|---|---|---|---|
| 290 | $T^{75}$ | $CH_2$ | $L^{50}$ | m.p. 73° C. |
| 291 | $T^{519}$ | $CH_2$ | $L^{50}$ | 1H-NMR(CDCl₃): δ =0.96 (d, 3H), 3.5 (s, 2H), 7.23 (s, 2H). |
| 292 | $T^{437}$ | $CH_2$ | $L^{50}$ | oil |
| 293 | $T^{438}$ | $CH_2$ | $L^{50}$ | oil |
| 294 | $T^{237}$ | $CH_2$ | $L^{50}$ | oil |
| 295 | $T^{140}$ | $CH_2$ | $L^{50}$ | oil |
| 296 | $T^{439}$ | $CH_2$ | $L^{50}$ | oil |
| 297 | $T^{32}$ | $CH_2$ | $L^{93}$ | oil |
| 298 | $T^{412}$ | $CH_2$ | $L^{50}$ | oil |
| 299 | $T^{413}$ | $CH_2$ | $L^{50}$ | oil |
| 300 | $T^{528}$ | $CH_2$ | $L^{50}$ | oil |
| 301 | $T^{529}$ | $CH_2$ | $L^{50}$ | oil |
| 302 | $T^{530}$ | $CH_2$ | $L^{50}$ | oil |
| 303 | $T^{531}$ | $CH_2$ | $L^{50}$ | oil |
| 304 | $T^{520}$ | $CH_2$ | $L^{50}$ | 1H-NMR(CDCl₃): δ =0.97 (d, 3H), 3.57 (s, 2H), 7.82 (s, 2H). |
| 305 | $T^{414}$ | $CH_2$ | $L^{50}$ | oil |

Further compounds not shown in this table can obtained using further combinations of the groups T, A and L defined.

TABLE 2

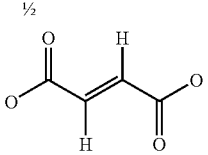

| Comp. No | R¹ | A | —N(R²)(R³) | X | Physico-chemical data |
|---|---|---|---|---|---|
| 1000 | $T^6$ | $CH_2$ | $L^{50}$ | Cl | m.p. 183–184° C. |
| 1001 | $T^{39}$ | $CH_2$ | $L^{27}$ | Cl | m.p. 218° C. |
| 1002 | $T^{46}$ | $CH_2$ | $L^{50}$ | ½ SO₄ | m.p. 139–141°C. |
| 1003 | $T^{39}$ | $CH_2$ | $L^{54}$ | Cl | m.p. 205° C. |
| 1004 | $T^{46}$ | $CH_2$ | $L^{50}$ | Me—C₆H₄—SO₂O | m.p. 172–173° C. |
| 1005 | $T^{46}$ | $CH_2$ | $L^{50}$ | CF₃COO | m.p. 42–44° C. |
| 1006 | $T^{46}$ | $CH_2$ | $L^{50}$ | Cl | m.p. 178–183° C. |
| 1007 | $T^{46}$ | $CH_2$ | $L^{50}$ | ½ OOC—COO | m.p. 165° C. |
| 1008 | $T^{46}$ | $CH_2$ | $L^{50}$ | ½ maleate | m.p. 95° C. |
| 1009 | $T^{46}$ | $CH_2$ | $L^{50}$ | camphorsulfonate | m.p. 157° C. |

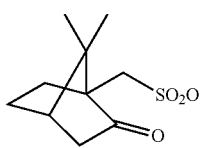

TABLE 2-continued

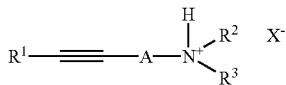

| Comp. No | R$^1$ | A | NR$^2$R$^3$ | X | Physico-chemical data |
|---|---|---|---|---|---|
| 1010 | T$^9$ | CH$_2$ | L$^{50}$ | Cl | m.p. 185–186° C. |
| 1011 | T$^{10}$ | CH$_2$ | L$^{50}$ | Cl | m.p. 213–214° C. |
| 1012 | T$^2$ | CH$_2$ | L$^{50}$ | Cl | m.p. 164–165° C. |
| 1013 | T$^{109}$ | CH$_2$ | L$^{50}$ | Cl | m.p. 138–139° C. |
| 1014 | T$^{110}$ | CH$_2$ | L$^{50}$ | Cl | m.p. 200–202° C. |
| 1015 | T$^{113}$ | CH$_2$ | L$^{50}$ | Cl | m.p. 162° C. |
| 1016 | T$^{114}$ | CH$_2$ | L$^{50}$ | Cl | m.p. 185° C. |
| 1017 | T$^{115}$ | CH$_2$ | L$^{50}$ | Cl | m.p. 139–140° C. |
| 1018 | T$^{39}$ | CH$_2$ | L$^{30}$ | Cl | m.p. 168–172° C. |
| 1019 | T$^{39}$ | CH$_2$ | L$^{77}$ | Cl | m.p. 230–232° C. |
| 1020 | T$^{125}$ | CH$_2$ | L$^{50}$ | Cl | m.p. 188° C. |
| 1021 | T$^{39}$ | CH$_2$ | L$^{79}$ | Cl | m.p. 213–215° C. |
| 1022 | T$^{127}$ | CH$_2$ | L$^{50}$ | Cl | m.p. 200–202° C. |
| 1023 | T$^{20}$ | CH$_2$ | L$^{50}$ | Cl | m.p. 233–234° C. |
| 1024 | T$^{39}$ | CH$_2$ | L$^{44}$ | Cl | m.p. 178–179° C. |
| 1025 | T$^{39}$ | CH$_2$ | L$^{81}$ | Cl | m.p. 195° C. |
| 1026 | T$^{39}$ | CH$_2$ | L$^{82}$ | Cl | m.p. 65–110° C. |
| 1027 | T$^{39}$ | CH$_2$ | L$^{83}$ | Cl | m.p. 50–79° C. |
| 1028 | T$^{39}$ | CH$_2$ | L$^{84}$ | Cl | m.p. 214–216° C. |
| 1029 | T$^{39}$ | CH$_2$ | L$^{85}$ | Cl | m.p. 220–221° C. |
| 1030 | T$^{39}$ | CH$_2$ | L$^{87}$ | Cl | m.p. 192–193° C. |
| 1031 | T$^{39}$ | CH$_2$ | L$^{13}$ | Cl | m.p. 210–212° C. |
| 1032 | T$^{133}$ | CH$_2$ | L$^{50}$ | Cl$_2$ | m.p. 270° C. |
| 1033 | T$^{39}$ | CH$_2$ | L$^{88}$ | Cl$_2$ | m.p. 282–283° C. |
| 1034 | T$^{39}$ | CH$_2$ | L$^{89}$ | Cl | m.p. 202° C. |
| 1035 | T$^{17}$ | CH$_2$ | L$^{50}$ | Cl | m.p. 225° C. |
| 1036 | T$^{46}$ | CH$_2$ | L$^{50}$ | Cl | m.p. 207–209° C. |
| 1037 | T$^{39}$ | CHMe | L$^{50}$ | Cl | m.p. 205–210° C. |
| 1038 | T$^{71}$ | CH$_2$ | L$^{50}$ | Cl | m.p. 201–204° C. |
| 1039 | T$^{39}$ | C(Me)$_2$ | L$^{50}$ | Cl | m.p. 208–210° C. |
| 1040 | T$^{46}$ | CH$_2$ | L$^{50}$ | C$_8$H$_{17}$COO | $^1$H-NMR(CDCl$_3$): δ = 0.85(t, 3H), 0.97 (d, 3H), 3.58(s, 2H), 7.39 (d, 1H), 7.56 (s, 1H), 7.61 (d, 1H) |
| 1041 | T$^{39}$ | CH$_2$ | L$^3$ | Cl | m.p. 206–208° C. |
| 1042 | T$^{33}$ | CH$_2$ | L$^{50}$ | Cl | m.p. 198–200° C. |
| 1043 | T$^{44}$ | CH$_2$ | L$^{50}$ | Cl | m.p. 222–224° C. |
| 1044 | T$^{39}$ | CH$_2$ | L$^{22}$ | Cl | m.p. 187–189° C. |
| 1045 | T$^{233}$ | CH$_2$ | L$^{50}$ | C$_8$H$_{17}$COO | $^1$H-NMR(CDCl$_3$): δ = 0.85(t, 3H), 0.97 (d, 3H), 3.60(s, 2H), 7.78(s, 1H), 7.81 (s, 1H) |
| 1046 | T$^{233}$ | CH$_2$ | L$^{50}$ | CF$_3$COO | $^1$H-NMR(CDCl$_3$): δ = 1.05(d, 3H), 4.20(s, 2H), 8.89 (s, 1H), 8.91(s,1H) |
| 1047 | T$^{233}$ | CH$_2$ | L$^{50}$ | Cl | m.p. 203–206° C. |
| 1048 | T$^{202}$ | CH$_2$ | L$^{50}$ | Cl | m.p. 172° C. |
| 1049 | T$^{236}$ | CH$_2$ | L$^{50}$ | Cl | m.p. 150° C. |
| 1050 | T$^{233}$ | CH$_2$ | L$^{91}$ | Cl | m.p. 151° C. |
| 1051 | T$^{39}$ | CH$_2$ | L$^{50}$ | CF$_3$COO | m.p. 188° C. |
| 1052 | T$^{39}$ | CH$_2$ | L$^{50}$ | Cl | m.p. 212° C. |
| 1053 | T$^{39}$ | CH$_2$ | L$^{50}$ | ½ SO$_4$ | m.p. 188° C. |
| 1054 | T$^{39}$ | CH$_2$ | L$^{50}$ | 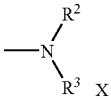 | m.p. 176° C. |
| 1055 | T$^{39}$ | CH$_2$ | L$^{50}$ | ½ OOC—COO | m.p. 186° C. |

TABLE 2-continued $$R^1 \!-\!\!\equiv\!\!-\!A\!-\!\overset{H}{\underset{R^3}{\overset{|}{N^+}}}\!\!\overset{R^2}{\underset{}{}} \quad X^-$$

$$-\overset{R^2}{\underset{R^3}{\overset{|}{N}}}$$

| Comp. No | $R^1$ | A | $R^3$ | X | Physico-chemical data |
|---|---|---|---|---|---|
| 1056 | $T^{39}$ | $CH_2$ | $L^{50}$ | ½ maleate | m.p. 128° C. |
| 1057 | $T^{203}$ | $CH_2$ | $L^{50}$ | Cl | m.p. 183° C. |
| 1058 | $T^{517}$ | $CH_2$ | $L^{50}$ | Cl | m.p. 192° C. |
| 1059 | $T^{46}$ | $CH_2$ | $L^{50}$ | $EtSO_2O$ | m.p. 132° C. |
| 1060 | $T^{233}$ | $CH_2$ | $L^{50}$ | $EtSO_2O$ | m.p. 104° C. |
| 1061 | $T^{169}$ | $CH_2$ | $L^{50}$ | Cl | m.p. 176° C. |
| 1062 | $T^{169}$ | $CH_2$ | $L^{50}$ | Me-C$_6$H$_4$-SO$_2$O | m.p. 161° C. |
| 1063 | $T^{39}$ | $CH_2$ | $L^{50}$ | $EtSO_2O$ | oil |
| 1064 | $T^{236}$ | $CH_2$ | $L^{50}$ | $EtSO_2O$ | viscous oil |
| 1065 | $T^{169}$ | $CH_2$ | $L^{50}$ | $CF_3COO$ | m.p. 78° C. |
| 1066 | $T^{169}$ | $CH_2$ | $L^{50}$ | ½ maleate | m.p. 100° C. |
| 1067 | $T^{169}$ | $CH_2$ | $L^{50}$ | $EtSO_2O$ | viscous oil |
| 1068 | $T^{518}$ | $CH_2$ | $L^{50}$ | Cl | foam |
| 1069 | $T^{184}$ | $CH_2$ | $L^{50}$ | Cl | m.p. 198° C. |
| 1070 | $T^{520}$ | $CH_2$ | $L^{50}$ | Cl | m.p. 168–170° C. |

B. FORMULATION EXAMPLES

Example A

A dust is obtained by mixing 10 parts by weight of active compound and 90 parts by weight of talc as inert material and comminuting the mixture in a hammer mill.

Example B

A wettable powder which is readily dispersible in water is obtained by mixing 25 parts by weight of active compound, 65 parts by weight of kaolin-containing quartz as inert material, 10 parts by weight of potassium lignosulfonate and 1 part by weight of sodium oleoylmethyltaurinate as wetter and dispersant and grinding the mixture in a pinned-disk mill.

Example C

A dispersion concentrate which is readily dispersible in water is prepared by mixing 40 parts by weight of active compound with 7 parts by weight of a sulfosuccinic monoester, 2 parts by weight of a sodium lignosulfonate and 51 parts by weight of water and grinding the mixture in a ball mill to a fineness of below 5 microns.

Example D

An emulsifiable concentrate can be prepared from 15 parts by weight of active compound, 75 parts by weight of cyclohexane as solvent and 10 parts by weight of ethoxylated nonylphenol (10 EO) as emulsifier.

Example E

Granules can be prepared from 2 to 15 parts by weight of active compound and an inert granule carrier material such as attapulgite, pumice granules and/or quartz sand. It is expedient to use a suspension of the wettable powder from Example B with a solids content of 30%, which is sprayed onto the surface of the attapulgite granules, and these are dried and mixed intimately. The wettable powder amounts to approximately 5% by weight and the inert carrier material to approximately 95% by weight of the finished granules.

C. BIOLOGICAL EXAMPLES

In the Examples A to M, P to Z and AA to AI below, compounds were considered to be active when, at a concentration of 500 ppm or less, they had an activity on the harmful organisms of 50% or more.

Example A

The leaves of 12 rice plants having a stem length of 8 cm were dipped for 5 seconds into an aqueous solution of the formulated compound to be examined. After the solution had run off, the rice plants treated in this manner were placed into a Petri dish and populated with about 20 larvae (L3 stage) of the rice leafhopper species *Nilaparvata lugens*. The Petri dish was closed and then stored in a climatized chamber (16 hours of light/day, 25° C., 40–60% relative atmospheric humidity). After 6 days of storage, the mortality among the leafhopper larvae was determined. The compounds of the following examples were active: Nos. 29, 32, 42, 43, 51, 70, 84, 1002, 1004, 1005, 1040, 180, 184, 193, 197, 203, 209, 1059, 264, 265, 1066.

Example B

A Petri dish whose bottom was covered with filter paper and which contained about 5 ml of insect diet was prepared. Pieces of filter paper with about 30, 24-hour-old eggs of the American tobacco budworm (*Heliothis virescens*) were dipped for about 5 seconds into an aqueous solution of the formulated compound to be examined and were subsequently placed in the Petri dish. A further 200 µl of the aqueous solution were spread over the insect diet. The Petri dish was closed and then stored at about 25° C. in a climatized chamber. After 6 days of storage, the effect of the preparation on the eggs and the larvae which might have hatched from these was determined (mortality). The compounds of the following examples were active: Nos. 14, 15, 17, 18, 29, 30, 32, 60, 70, 97, 100, 119, 124, 1000, 1002, 1004, 1005, 1011, 1038, 1040, 1042, 1044, 1045, 1046, 1047, 1036, 167, 171, 172, 173, 174, 175, 181, 176, 177, 178, 179, 180, 182, 183, 188, 189, 190, 191, 192, 193, 194, 195, 197, 201, 1048, 203, 204, 24, 207, 209, 210, 214, 215, 216, 217, 221, 222, 224, 225, 226, 229, 230, 152, 1051, 1052, 1054, 1055, 1056, 232, 234, 1057, 1059, 1060, 1061, 1062, 1063, 236, 239, 240, 241, 244, 245, 246, 247, 251, 252, 253, 254, 256, 263, 266, 1065, 1067, 270, 271, 272, 273, 283, 284, 285, 286, 289, 290, 291, 292, 295, 296, 300, 301, 302.

Example C

A Petri dish, half of whose bottom was covered with filter paper and which contained a germinated maize corn on a moist cotton pad, was prepared. About 50, 4-5-day-old eggs of the corn rootworm (*Diabrotica undecimpunctata*) were transferred onto the filter paper. Three drops of 200 µl of an aqueous solution of the formulated compound to be examined were pipetted onto the eggs, and the rest was pipetted onto the maize corn. The Petri dish was closed and stored at about 25° C. in a climatized chamber. After 6 days of storage, the effect of the compound on the eggs and the larvae which might have hatched from these was determined (mortality). The compounds of the following examples were active: Nos. 17, 18, 31, 32, 43, 58, 60, 70, 152, 1001, 1002, 1004, 1005, 1038, 1040, 1042, 1047, 1036, 185, 189, 190, 191, 193, 194, 196, 197, 201, 203, 1050, 204, 205, 298, 207, 209, 228, 152, 231, 1051, 1052, 1053, 1054, 1055, 1056, 234, 1057, 1058, 1059, 1060, 1061, 1062, 235, 1063, 1064, 1065, 1066, 1067, 1068, 1069, 267, 281, 282, 290, 291, 295, 297.

Example D

Apples were dipped into an aqueous solution of the formulated compound to be examined. The apples were then populated with 10 L1 larvae of the codling moth (*Carpocapsa pomonella*). After 14 days of storage at about 25° C., the effect of the compound on the larvae was determined (mortality). The compounds of the following examples were active: Nos. 14, 15, 17, 18, 70, 1007, 1008, 1009, 1036, 1038, 197.

Example E

Leaves of cotton plants were placed into a Petri dish, populated with 10 L2 larvae of the Egyptian cotton leafworm (*Spodoptera littoralis*) and sprayed with an aqueous solution of the formulated compound to be examined. After 4 days of storage at about 23° C., the effect of the compound on the larvae was determined (mortality). The compounds of the following examples were active: Nos. 18, 70, 1007, 1008, 1009, 1036 und 1038.

Example F

Germinated field bean seeds (*Vicia faba*) with radicles were transferred into brown glass bottles filled with tap water and subsequently populated with approximately 100 black bean aphids (*Aphis fabae*). Plants and aphids were then dipped for 5 seconds into an aqueous solution of the formulated compound to be examined. After the solution had run off, plants and animals were stored in a climatized chamber (16 hours of light/day, 25° C., 40–60% relative atmospheric humidity). After 3 and 6 days of storage, the effect of the compound on the aphids was determined (mortality). The compounds of the following examples were active: 30, 43, 228, 262, 291.

Example G

A Petri dish whose bottom was covered with filter paper and which contained about 5 ml of insect diet is prepared. Five L2 larvae of the Egyptian cotton leafworm (*Spodoptera littoralis*) were counted into a small beaker. 200 µl of an aqueous solution of the formulated preparation to be examined were pipetted into the beaker. The treated larvae were then poured into the Petri dish, and a further 200 µl of the aqueous solution were distributed over the insect diet. The Petri dish was closed and then stored at about 25° C. in a climatized chamber. After 6 days of storage, the effect of the compound on the larvae was determined (mortality). The compounds of the following examples were active: 29, 70, 60, 159, 1005, 1040, 1042, 1044, 1045, 1046, 1047.

Example H

In a glass vessel, an aqueous solution of the formulated compound to be examined was added to about 3000 freshly hatched active (mobile) larvae (2nd development stage) of the root gall nematode (*Meloidogyne incognita*) (final volume 20 ml). After 6 days of permanent exposure of the nematode larvae, the percentage of the individual larvae immobilized by the activity of the compound was determined in comparison to the untreated controls (contact activity). The compounds of the following examples were active: 39, 52, 159, 161, 162, 163, 164, 165, 1045, 1046, 1047, 179, 183, 187, 1048, 298, 206, 208, 227, 230, 1061, 237, 238, 245, 250, 255, 256, 260, 268, 269, 274, 275, 288, 290.

Example I

Ten L1 larvae of the codling moth (*Carpocapsa pomonella*) were placed into a Petri dish filled with insect diet. Insect diet and the larvae used were then sprayed with an aqueous solution of the formulated compound to be examined. The Petri dish was then closed with a lid. After 8 days of storage at about 23° C., the effect of the compound on the larvae was determined (mortality). The compounds of the following examples were active: 60, 70, 1002, 1005.

Example J

About 20 eggs of the codling moth (*Carpocapsa pomonella*) were placed into a Petri dish filled with insect diet. Insect diet and eggs were then sprayed with an aqueous solution of the formulated compound to be examined. The Petri dish was then closed with a lid. After 8 days of storage at about 23° C., the effect of the compound on the eggs and any larvae which may have hatched therefrom was determined (mortality). The compounds of the following examples were active: 70, 1036.

Example K

A white cabbage leaf was sprayed with an aqueous solution of the formulated compound to be examined. After the spray coating had dried, the treated leaf was populated with larvae of the diamondback moth (*Plutella maculipennis*). After 3 days of storage at about 23° C., the effect of the compound on the larvae was determined (mortality). The compounds of the following examples were active: 60, 70, 1002, 1004, 1005, 1036, 197.

Example L

Potato leaves were populated with larvae of the Colorado beetle (*Leptinotarsa decemlineata*). Leaves and larvae were then sprayed with an aqueous solution of the formulated compound to be examined. After 4 days of storage at about 25° C., the effect of the compound on the larvae was determined (mortality). The compounds of the following examples were active: 60, 70, 1002, 1004, 1005, 1036, 1047, 197.

Example M

The formulated compound was mixed with defibrinated cattle blood. 10 adult cat fleas (*Ctenocephalides felis*) were fed with this blood-preparation mixture. After 48 hours at about 38° C., the effect of the compound on the fleas was determined (mortality). The compounds of the following examples were active: 70, 1002, 1004, 1005, 1036, 60, 197, 1057.

Example N

Test 1

Disks of beet leaves (diameter 49 mm) were placed onto 20% agar in Petri dishes made of plastic (diameter 9 cm). Each dish was populated with 10 adults of *Phaedon cochleariae* which were cultivated on beets. The compound to be examined was prepared in an aqueous, 50% by volume strength acetone solution. The solution of the compound was then sprayed onto the infected leaf disks using a Potter tower, at an application rate of 660 liters per hectare. Each experiment was carried out with 4 repetitions. In the controls, the infected leaf disks were only sprayed with the 50% strength aqueous acetone solution, if at all.

After 48 h, the mortality was determined and, using Abbott's formula, compared to the mortality of the controls. The $LD_{90}$ concentration (dosage which leads to 90% mortality, here stated in % by weight) as then calculated. The compounds of Examples 14, 18, 29, 33, 152, 1001 and 1039 showed an $LD_{90}$ at a dosage of 0.05% or less.

Test 2

Instead of *Phaedon cochleariae*, 5 *Pieris brassicae* larvae of the 2nd development stage were used. The test was carried out analogously to the procedure described in Test 1. The compounds of Examples 14, 29, 33, 100, 152, 1005 and 1039 showed an $LD_{90}$ at a dosage of 0.006% or less.

Test 3

Instead of *Pieris brassicae*, 10 *Plutella xylostella* larvae of the 2nd development stage were used. The test was carried out analogously to the procedure described in Test 2. The compounds of Examples 4, 6, 7, 10, 12, 13, 14, 15, 16, 17, 18, 19, 20, 23, 24, 25, 26, 28, 29, 31, 32, 33, 34, 35, 152, 1000, 1001, 1005 and 1039 showed an $LD_{90}$ at a dosage of 0.05% or less.

Test 4

The compound to be examined was dissolved in pure acetone and mixed into soil having a moisture of about 10%. The solvent was evaporated, and in each case 5 g of treated soil were then filled into a tube, and 0.5 ml of water was added. 10 Gryllus bimaculatus nymphs (1st development stage) and a disk of green cabbage as a source of food were placed into each tube. Each experiment was carried out with 4 repetitions. The controls were untreated soil and soil which had been treated only with acetone. The ventilated tubes were cultivated at 25° C. for 48 h, after which the mortality was determined.

Taking into account the control mortality, the $LC_{90}$ was determined as ppm concentration in the soil, using Abbott's formula. The compounds of Examples 152 and 1039 showed an $LC_{90}$ at a concentration of 50 ppm or less.

Test 5

The compound to be examined was dissolved in pure acetone, and a small amount of this solution was applied to the surface of a milk-yeast-agar diet (5 ml) in a small sample glass (7 cm×2.5 cm). After 24 h, about 10 *Lucilia sericata* larvae of the 1st development stage were placed on the treated diet. Each experiment was carried out with 3 repetitions. The diet in the tubes of the control was treated only with an equivalent amount of acetone. The 'minimum effective dose' (MED) was defined as the lowest dosage at which the further development of the larvae is stopped, and as a consequence, there is no subsequent hatching of adult flies.

The compounds of Example 4 and 1039 showed an MED at 100 µg/glass or less.

Test 6

The compound to be examined was made up in an aqueous 50% by volume strength acetone solution. Two-week-old *Boophilus microplus* larvae which were sandwiched between 2 disks of filter paper were dipped for 4 minutes into the solution of the compound. Each experiment was carried out with two repetitions. The corresponding controls were only treated with the 50% strength aqueous acetone solution. The larvae were then placed onto new filter paper disks and stored at about 25° C. and 95% relative atmospheric humidity. The 'minimum effective concentration' (MEC) was defined as the lowest concentration, expressed in % by weight of the compound to be examined in the solution, at which 100% mortality occurred within 48 h. The compounds of Examples 2, 4, 6, 9, 20, 22, 25, 27, 28 and 32 had an MEC of 0.04% or less.

Test 7

The compound to be examined was made up in an aqueous, 50% by volume strength acetone solution. Female cattle ticks (*Boophilus microplus*) which had sucked themselves full and had fallen off in a natural manner from artifically infected calves were washed and dried. With constant stirring, they were then dipped for 1 minute into the solution of the compound. After the solution had run off, the females were transferred into small sample glasses (7 cm×2.5 cm) and stored in an incubator at 30° C. and 94% relative atmospheric humidity. Each experiment involved 2×10 female ticks. The control group was treated only with the 50% strength aqueous acetone solution. Mortality and deposition of eggs were analyzed six days after treatment. The 'minimum effective concentration' (MEC) was defined as the lowest concentration, expressed in % by weight of the compound to be examined in the solution, at which the ticks were no longer able to produce viable eggs. The compounds of Examples 20, 27 and 32 had an MEC of less than 0.2%.

Example O

Test 1

The compound to be examined was dissolved in pure acetone, and a standard cockroach bait mixture comprising mainly water, corn syrup and glycerol, and minor portions of poultry liver and starch with small amounts of hydroxymethylcellulose, propyl- and methyl-para-hydroxybenzoic acid and an attractant scent was added. After the acetone had evaporated, 0.1 g of the bait was placed into a box made of plastic, and 20 adult *Blattella germanica* (in each case 10 male and 10 female) were then added ('no choice' test). After 7 days, the effect was determined. Present in the bait in an amount of 0.5% by weight, the compounds of Examples 70 and 1036 caused a mortality of 45% and 100%, respectively. When present in the bait in an amount of 1.0% by weight, the compounds of Examples 70 and 1036 additionally had a repellent effect.

Test 2

The compound to be examined was dissolved in pure acetone, and a standard cockroach bait mixture comprising mainly water, corn syrup and glycerol, and minor portions of poultry liver and starch with small amounts of hydroxymethylcellulose, propyl- and methyl-para-hydroxybenzoic acid and an attractant scent was added. After evaporation of the acetone, 0.1 g of the bait prepared in this manner and 0.1 g of an identical bait without test compound were placed into a box made of plastic. 20 adult *Blattella germanica* (in each case 10 male and 10 female) were then placed into the box ('choice' test). After 7 days, the effect was determined. Present in the bait in an amount of 0.5% by weight, the compounds of Examples 70 and 1036 caused a mortality of 30% and 60%, respectively. When present in the bait in an amount of 1.0% by weight, the compounds of Examples 70 and 1036 had a repellent effect without mortality, since the baits with the test compounds were not fed on.

Test 3

The compound to be examined was dissolved in pure acetone, and small amounts thereof were pipetted into vessels containing in each case 100 ml of water. Mosquito larvae of the 2nd development stage of *Aedes aegypti*, *Anopheles arabiensis* and *Culex quinquefasciatus* were pipetted into each of the vessels. After 24 h, the effect was determined. At 100 ppm, the compounds of Examples 70 and 1036 caused a mortality of 100% among the larvae of *Aedes aegypti*, *Anopheles arabiensis* and *Culex quinquefasciatus*.

Test 4

In each case 50 mg of the compound to be examined were dissolved in pure acetone and pipetted onto an evaporation felt mat free of active compound (syn. 'Emanator Mat'; ®Bengal Mosquito Mats, Zobele Industrie Chimiche S.p.A., Via Fersina, Trento, Italy). After the acetone had evaporated, the evaporation felt mat prepared in this manner was placed into an electric heater (®Bengal Heater, Zobele Industrie Chimiche S.p.A., Via Fersina, Trento, Italy). On heating of the felt mat at 150° C., the compound to be examined was volatilized in a test chamber having a volume of 2 m$^3$. The activity of the compound was tested using in each case 100 female adult mosquitoes—*Aedes aegypti* and *Culex quinquefasciatus*—with 3 repetitions. Evaluation for immobility (syn. 'knockdown') was carried out at one-minute intervals and terminated after a total of 20 minutes. In 50% of the female *Aedes aegypti*, the compounds of Example 70 and 1036 caused a knockdown (syn. $KT_{50}$; 'knockdown time of 50% of individuals', i.e. the time after which 50% of the mosquitoes were immobilized) after 12 and 11.5 minutes, respectively. For *Culex quinquefasciatus*, the $KT_{50}$ was 8 and 9.25 minutes.

Test 5

In each case 50 mg of the compound to be examined were dissolved in pure acetone and pipetted onto an evaporation felt mat free of active compound (syn. 'Emanator Mat'; ®Bengal Mosquito Mats, Zobele Industrie Chimiche S.p.A., Via Fersina, Trento, Italy). After the acetone had evaporated, the evaporation felt mat prepared in this manner was used once for 20 minutes and then stored for 2 weeks. Subsequently, the prepared evaporation felt mat was examined once more. The test was carried out according to the procedure described in test 4. In the case of *Aedes aegypti*, the compounds of Example 70 and 1036 caused a $KT_{50}$ of 11 and 10.5 minutes, respectively. In the case of *Culex quinquefasciatus*, the $KT_{50}$ was 7.5 and 9 minutes, respectively.

Example P

A cabbage leaf was dipped for about 5 seconds into an aqueous solution of the formulated compound to be examined. After drying, the cabbage leaf treated in this manner was transferred into a container and populated with 10 larvae of the diamondback moth (*Plutella maculipennis*). The container was then closed with a lid. After 3 days of storage at about 23° C., the effect of the compound on the larvae was determined. The following examples were active: 1036, 70, 60, 209.

Example Q

Cut stems of bean plants (*Phaseolus vulgaris*) carrying one leaf were transferred into brown glass bottles filled with tap water and subsequently populated with approximately 100 spider mites (*Tetranychus urticae*). The plant leaf and the spider mites were then dipped for 5 seconds into an aqueous solution of the formulated compound to be examined. After the solution had run off, plants and animals were stored in a climatized chamber (16 hours of light/day, 25° C., 40–60% relative atmospheric humidity). After 6 days of storage, the mortality of the compound on all stages of the spider mites was determined. The following examples were active: 299, 305, 206, 268, 269, 287.

Example R

Germinated field bean seeds (*Vicia faba*) with radicles were transferred into brown glass bottles filled with tap water. Four milliliters of an aqueous solution of the formulated compound to be examined were pipetted into the brown glass bottle. The field bean was then heavily populated with approximately 100 black bean aphids (*Aphis fabae*). Plant and animals were then stored in a climatized chamber (16 hours of light/day, 25° C., 40–60% relative atmospheric humidity). After 3 and 6 days of storage, the root-systemic activity of the compound on the aphids was determined (mortality). The following examples were active: 184, 186, 305, 220, 265.

Example S

A Petri dish whose bottom was covered with filter paper and which contains about 5 ml of insect diet is prepared. Five L2 larvae of sugar beet army worm (*Spodoptera exigua*) were counted into a small beaker. 200 µl of an aqueous solution of the formulated compound to be examined were pipetted into the beaker. The treated larvae were then poured into the Petri dish and a further 200 µl of the aqueous solution were distributed over the insect diet. The Petri dish was closed and then stored at 25° C. in a climatized chamber. After 6 days of storage, the mortality among the larvae was determined. The following examples were active: 1036, 175, 184, 1051, 1054, 1055, 234, 1057, 1059, 1060, 1063, 243, 245, 251, 257, 259, 266, 1065, 1067, 290, 291.

Example T 10 larvae of the turnip moth (*Agrotis segetum*) were placed into a Petri dish filled with insect diet. Insect diet and the larvae employed were then sprayed with an aqueous solution of the formulated compound to be examined. The Petri dish was then closed with a lid. After 7 days of storage at about 23° C., the mortality among the larvae was determined. The following example was active: 70.

Example U

Rice seed was germinated on moist cotton in cultivation glasses. After the plants had grown to a stem length of approximately 8 cm, the leaves were sprayed to run-off point with an aqueous solution of the formulated compound to be examined. After the solution had run off, the treated rice plants were placed in cultivation containers and populated with in each case 10 larvae (L3 stage) of the rice leafhopper species *Nilaparvata lugens*. Plants and animals were stored in a climatized chamber (16 hours of light/day, 25° C., 40–60% relative atmospheric humidity). After 4 days of storage, the mortality among the larvae was determined. The following example was active: 70.

Example V

Insect diet (as freeze-dried cube) was dipped into an aqueous solution of the formulated compound to be examined and then placed into a Petri dish. 10 L2 larvae of the American tobacco budworm (*Heliothis virescens*) were then added. The Petri dish was then closed with a lid. After 4 days of storage at about 23° C., the mortality among the larvae was determined. The following examples were active: 1036, 60.

Example W 2.4 ml of an aqueous solution of the formulated compound to be examined were pipetted into a bottle filled with 21.6 ml of water. A 14-day-old cabbage plant was transferred into the bottle. After one week, the plant was populated with 5 larvae of the diamondback moth (*Plutella maculipennis*). Plants and animals were then stored in a climatized chamber (23° C., 40–60% relative atmospheric humidity). After 3 days of storage, the root-systemic activity of the compound on the larvae was determined (mortality). The following examples were active: 1036, 70, 60.

Example X

Insect diet (as freeze-dried cube) was dipped into an aqueous solution of the formulated compound to be examined and then placed into a Petri dish. 10 L2 larvae of the sugar beet armyworm (*Spodoptera exigua*) were then added. The Petri dish was then closed with a lid. After 4 days of storage at about 23° C., the mortality among the larvae was determined. The following examples were active: 1036, 60.

Example Y

Cotton plants were sprayed with an aqueous solution of the formulated compound to be examined. After drying, leaves were cut off, placed into a Petri dish and populated with 5 L2 larvae of the sugar beet armyworm (*Spodoptera exigua*). After 4 days of storage at about 23° C., the mortality among the larvae was determined. The following examples were active: 1036, 70, 60, 1047, 197.

Example Z

Cotton leaves were populated with 5 L2 larvae of the sugar beet armyworm (*Spodoptera exigua*) and then sprayed with an aqueous solution of the formulated compound to be examined. After 4 days of storage at about 23° C., the mortality among the larvae was determined. The following examples were active: 1036, 70, 60, 1047, 197.

Example AA

Insect diet was mixed with an aqueous solution of the formulated compound to be examined and populated with 10 L1 larvae of the codling moth (*Carpocapsa pomonella*). After 14 days of storage at about 23° C., the mortality among the larvae was determined. The following examples were active: 70, 197.

Example AB

Cotton leaves were placed into a Petri dish, populated with 5 L2 larvae of the American tobacco budworm (*Heliothis virescens*) and sprayed with an aqueous solution of the formulated compound to be examined. After 4 days of storage at about 25° C., the mortality among the larvae was determined. The following examples were active: 70, 1047, 197.

Example AC

An aqueous solution of the formulated compound to be examined was mixed with soil. After 0d, 21d and 42d, eggs of the southern corn rootworm (*Diabrotica undecimpunctata*) were placed together with 2 pre-swollen maize corns into a dish, covered with the treated soil and moisted with 10 ml of water. Soil and eggs were placed in a greenhouse (23° C., 60% relative atmosphere humidity). After 2 weeks of storage, the effect of the compound on the eggs and any larvae hatched therefrom was determined (mortality). The following examples were active: 70, 60, 197, 204.

Example AD

For oviposition, bush beans (*Phaseolus vulgaris*) were populated for 48 hours with adults of the white fly (*Trialeurodes vaporariorum*). After the larvae had hatched, the plants were sprayed to run-off point with an aqueous solution of the formulated compound to be examined. After 11 days, the larvicidal action was determined. The following examples were active: 1036, 70, 60, 1040, 197.

Example AE

An aqueous solution of the formulated compound to be examined was mixed with soil. ⅔ of the soil were filled into a pot and a pregerminated maize corn and about 30 larvae of the turnip moth (*Agrotis segetum*) were added and covered with the remaining soil. Soil and larvae were placed in a greenhouse (23° C., 60% relative atmospheric humidity). After 7 days of storage, the mortality among the larvae was determined. The following example was active: 70

Example AF

The formulated compound was pipetted onto filter paper. After the solvent had evaporated, 20–30 tick larvae (*Rhipicephalus sanguineus*) were placed onto the filter paper. After 24 hours at about 25° C., the effect of the compound on the ticks was determined (mortality). The following examples were active: 197, 1057.

Example AG

190 µl of culture solution and about 20 eggs of the yellow fever mosquito (*Aedes aegypti*) were placed into each well of a microtiter plate. After the larvae had hatched, 10 µl of an aqueous solution of the formulated compound to be examined were added with a pipette. After 3 days of storage at 25° C. and 60% relative atmospheric humidity, the larvicidal activity of the compound was determined. The following examples were active: 209, 211, 213, 215, 216, 218, 219, 234, 1057, 1059, 1060, 1061, 1062, 235, 1064, 242, 244, 245, 248, 249, 250, 251, 252, 254, 256, 258, 259, 261, 264, 265, 266, 1065, 1066, 1067, 1068, 1069, 267, 289, 290, 291, 292, 293, 294, 301, 303.

Example AH

Cotton leaves were placed into a Petri dish, sprayed with an aqueous solution of the formulated compound to be examined and, after drying, populated with 5 L2 larvae of the American tobacco budworm (*Heliothis virescens*). After 2, 3 and 4 days of storage at about 25° C., the antifeeding activity of the compound on the larvae was determined. The following examples were active: 1036, 70, 60.

Example AI

A potato plant was sprayed with an aqueous solution of the formulated compound to be examined and, together with an untreated plant, placed in a cage. The cage was populated with 100 larvae of the Colorado beetle (*Leptinotarsa decemlineata*). After 1 and 3 days of storage at about 25° C., the repellent effect of the compound on the larvae was determined. The following examples were active: 1036, 70, 60.

What is claimed is:

1. A method for controlling harmful arthropods and/or helminths, which comprises applying to these or to the plants or animals, areas or substrates infected by them an arthropodicidally or helminthicidally effective amount of a compound of the formula (I)

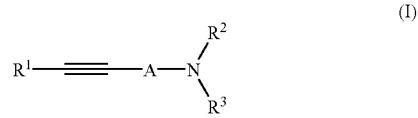

or an N-oxide or salt thereof, wherein:
a) $R^1$ is phenyl, unsubstituted or mono- or polysubstituted by identical or different radicals selected from the group consisting of halogen, $(C_1-C_4)$-alkyl, $(C_1-C_4)$-haloalkyl, nitro, cyano, $(C_1-C_4)$-alkoxy, $(C_1-C_4)$-haloalkoxy, and phenyl, wherein phenyl is unsubstituted or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and $(C_1-C_4)$-alkylthio, or two substituents together form a group —O—$(CH_2)_2$—O—;
b) A is a group $CR^4R^5$ wherein:
$R^4$ is hydrogen or methyl; and
$R^5$ is hydrogen or $(C_1-C_4)$-alkyl; and
c) $R^2$ and $R^3$ together with the nitrogen atom to which they are attached, form a piperidine radical which is unsubstituted or mono- or polysubstituted by identical or different substituents selected from the group consisting of $(C_1-C_4)$-alkyl, and $(C_1-C_4)$-haloalkyl.

2. A compound of the formula (I)

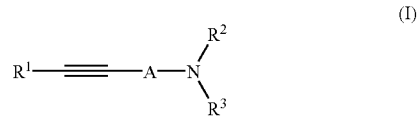

or its N-oxide or salt, wherein:
a) $R^1$ is phenyl which is polysubstituted by identical or different radicals selected from the group consisting of halogen, $(C_1-C_4)$-alkyl, $(C_1-C_4)$-haloalkyl, nitro, cyano, $(C_1-C_4)$-alkoxy, $(C_1-C_4)$-haloalkoxy, and phenyl wherein phenyl is unsubstituted or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and $(C_1-C_4)$-alkylthio, or two substituents together form a group —O—$(CH_2)_2$—O—;
b) A is a group $CR^4R^5$, wherein:
$R^4$ is hydrogen or methyl; and
$R^5$ is hydrogen or $(C_1-C_4)$-alkyl; and
c) $R^2$ and $R^3$ together with the nitrogen atom to which they are attached form a piperidine radical which is monoor polysubstituted by identical or different substituents selected from the group consisting of methyl, ethyl, n-propyl, isopropyl, n-butyl, isobutyl, 2-butyl and $(C_1-C_4)$-haloalkyl with the proviso that, when $R^2$ and $R^3$ together with the nitrogen atom to which they are attached form a piperidine radical which is substituted in the position by unsubstituted or substituted alkyl, then $R^1$ is not 3,5-bistrifluoromethylphenyl.

3. A process for preparing a compound of the formula (I) as claimed in claim 2, which comprises reacting a compound of the formula (II)

$R^1$—X (II)

wherein:

X is —O—SO$_2$)—CF$_3$ or halogen and $R^1$ is as defined in formula (I) as claimed in claim 2 in the presence of a palladium catalyst, a base and a copper(I) salt with a compound of the formula (III)

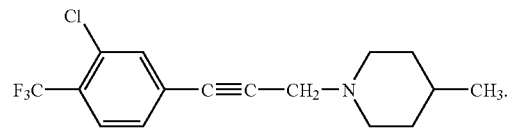

(III)

wherein A, $R^2$ and $R^3$ are as defined in formula (I) as claimed in claim 2.

4. A pesticidal composition, comprising at least one compound of the formula (I) as claimed in claim 2 and at least one formulation auxiliary.

5. A pesticidal composition for application as an insecticidal, acaricidal or nematicidal composition comprising an insecticidally, acaricidally or nematicidally effective amount of at least one compound of the formula (I) as claimed in claim 2 together with additives or auxiliaries customary for this application.

6. A pesticidal composition comprising an insecticidally, acaricidally or nematicidally effective amount of at least one compound of the formula (I) as claimed in claim 2 and at least one further active compound together with auxiliaries and additives customary for this application.

7. A pesticidal composition for application in the protection of wood or as a preservative in sealants, in paints, in cooling lubricants for metal working or in drilling and cutting oils, comprising an insecticidally, acaricidally or nematicidally effective amount of at least one compound of the formula (I) as claimed in claim 2 together with auxiliaries and additives customary for these applications.

8. A veterinary medicament comprising an insecticidally, acaricidally or nematicidally effective amount of a compound as claimed in claim 2 together with at least one additive or auxiliary customary for veterinary administration.

9. A seed, treated or coated with an insecticidally, acaricidally or nematicidally effective amount of a compound of the formula (I) as claimed in claim 2.

10. A seed, treated or coated with an insecticidally, acaricidally or nematicidally effective amount of a composition as claimed in claim 4.

11. A compound as claimed in claim 2, wherein the radicals substituted on phenyl are selected from the group consisting of F, Cl, CF$_3$, methyl, ethyl, isopropyl, n-propyl, nitro, cyano, —OCH$_3$, —OC$_2$H$_5$, and phenyl.

12. A compound as claimed in claim 2, wherein $R^4$ is hydrogen and $R^5$ is hydrogen or methyl.

13. A compound as claimed in claim 11, wherein $R^4$ is hydrogen and $R^5$ is hydrogen or methyl.

14. The compound as claimed in claim 13, having the formula

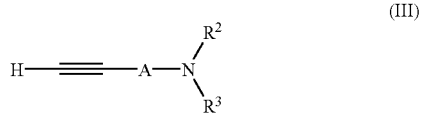

15. A method for controlling harmful arthropods and/or helminths, which comprises applying to these or to the plants or animals, areas or substrates infected by them an arthropodicidally or helminthicidally effective amount of a compound of the formula (I) as defined by claim 2.

16. A method for controlling harmful arthropods and/or helminths, which comprises applying to these or to the plants or animals, areas or substrates infected by them an arthropodicidally or helminthicidally effective amount of a compound of the formula (I) as defined by claim 11.

17. A method for controlling harmful arthropods and/or helminths, which comprises applying to these or to the plants or animals, areas or substrates infected by them an arthropodicidally or helminthicidally effective amount of a compound of the formula (I) as defined by claim 12.

18. A method for controlling harmful arthropods and/or helminths, which comprises applying to these or to the plants or animals, areas or substrates infected by them an arthropodicidally or helminthicidally effective amount of a compound of the formula (I) as defined by claim 13.

19. A method for controlling harmful arthropods and/or helminths, which comprises applying to these or to the plants or animals, areas or substrates infected by them an arthropodicidally or helminthicidally effective amount of a compound of the formula (I) as defined by claim 14.

20. A pesticidal composition comprising an insecticidally, acaricidally or nematicidally effective amount of at least one compound of the formula (I) as claimed in claim 11 and at least one formulation auxiliary therefor.

21. A pesticidal composition comprising an insecticidally, acaricidally or nematicidally effective amount of at least one compound of the formula (I) as claimed in claim 12 and at least one formulation auxiliary therefor.

22. A pesticidal composition comprising an insecticidally, acaricidally or nematicidally effective amount of at least one compound of the formula (I) as claimed in claim 13 and at least one formulation auxiliary therefor.

23. A pesticidal composition comprising an insecticidally, acaricidally or nematicidally effective amount of at least one compound of the formula (I) as claimed in claim 14 and at least one formulation auxiliary therefor.

24. A pesticidal composition for application in the protection of wood or as a preservative in sealants, in paints, in cooling lubricants for metal working or in drilling and cutting oils, comprising an insecticidally effective amount of at least one compound of the formula (I) as claimed in claim 11 together with auxiliaries and additives customary for these applications.

25. A pesticidal composition for application in the protection of wood or as a preservative in sealants, in paints, in cooling lubricants for metal working or in drilling and cutting oils, comprising an insecticidally effective amount of at least one compound of the formula (I) as claimed in claim 12 together with auxiliaries and additives customary for these applications.

26. A pesticidal composition for application in the protection of wood or as a preservative in sealants, in paints, in cooling lubricants for metal working or in drilling and cutting oils, comprising an insecticidally effective amount of at least one compound of the formula (I) as claimed in claim 13 together with auxiliaries and additives customary for these applications.

27. A pesticidal composition for application in the protection of wood or as a preservative in sealants, in paints, in cooling lubricants for metal working or in drilling and cutting oils, comprising an insecticidally effective amount of at least one compound of the formula (I) as claimed in claim 14 together with auxiliaries and additives customary for these applications.

28. A veterinary medicament comprising an insecticidally, acaricidally or nematicidally effective amount of a compound of the formula (I) as claimed in claim 11 together with at least one auxiliary customary for veterinary administration.

29. A veterinary medicament comprising an insecticidally, acaricidally or nematicidally effective amount of a compound of the formula (I) as claimed in claim 12 together with at least one auxiliary customary for veterinary administration.

30. A veterinary medicament comprising an insecticidally, acaricidally or nematicidally effective amount of a compound of the formula (I) as claimed in claim 13 together with at least one auxiliary customary for veterinary administration.

31. A veterinary medicament comprising an insecticidally, acaricidally or nematicidally effective amount of a compound of the formula (I) as claimed in claim 14 together with at least one auxiliary customary for veterinary administration.

32. A seed, treated or coated with an insecticidally, acaricidally or nematicidally effective amount of a compound of the formula (I) as claimed in claim 11.

33. A seed, treated or coated with an insecticidally, acaricidally or nematicidally effective amount of a compound of the formula (I) as claimed in claim 12.

34. A seed, treated or coated with an insecticidally, acaricidally or nematicidally effective amount of a compound of the formula (I) as claimed in claim 13.

35. A seed, treated or coated with an insecticidally, acaricidally or nematicidally effective amount of a compound of the formula (I) as claimed in claim 14.

36. A seed, treated or coated with an insecticidally, acaricidally or nematicidally effective amount of a composition as claimed in claim 20.

37. A seed, treated or coated with an insecticidally, acaricidally or nematicidally effective amount of a composition as claimed in claim 21.

38. A seed, treated or coated with an insecticidally, acaricidally or nematicidally effective amount of a composition as claimed in claim 22.

39. A seed, treated or coated with an insecticidally, acaricidally or nematicidally effective amount of a composition as claimed in claim 23.

* * * * *